(12) United States Patent
Damude et al.

(10) Patent No.: US 8,298,797 B2
(45) Date of Patent: Oct. 30, 2012

(54) Δ-9 ELONGASES AND THEIR USE IN MAKING POLYUNSATURATED FATTY ACIDS

(75) Inventors: Howard Glenn Damude, Hockessin, DE (US); Quinn Qun Zhu, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 213 days.

(21) Appl. No.: 12/825,523

(22) Filed: Jun. 29, 2010

(65) Prior Publication Data

US 2010/0267098 A1    Oct. 21, 2010

Related U.S. Application Data

(62) Division of application No. 12/102,879, filed on Apr. 15, 2008, now Pat. No. 7,794,701.

(60) Provisional application No. 60/911,925, filed on Apr. 16, 2007.

(51) Int. Cl.
| | |
|---|---|
| C12P 7/66 | (2006.01) |
| C12N 15/74 | (2006.01) |
| A01N 63/00 | (2006.01) |
| C07H 21/04 | (2006.01) |
| A61K 48/00 | (2006.01) |

(52) U.S. Cl. .... 435/134; 435/471; 424/93.2; 424/93.21; 536/23.2; 536/23.7

(58) Field of Classification Search .......... 424/93.2, 424/93.21; 435/134, 471; 536/23.2, 23.7
See application file for complete search history.

(56) References Cited

U.S. PATENT DOCUMENTS

| | | | |
|---|---|---|---|
| 7,125,672 B2 | 10/2006 | Picataggio et al. | |
| 7,238,482 B2 | 7/2007 | Picataggio et al. | |
| 7,335,476 B2 | 2/2008 | Picataggio et al. | |
| 2005/0287652 A1 | 12/2005 | Damude et al. | |
| 2006/0035351 A1 | 2/2006 | Zhu et al. | |
| 2006/0094092 A1 | 5/2006 | Damude et al. | |
| 2006/0110806 A1 | 5/2006 | Damude et al. | |
| 2006/0115881 A1 | 6/2006 | Damude et al. | |
| 2007/0117190 A1 | 5/2007 | Damude et al. | |
| 2007/0118929 A1 | 5/2007 | Damude et al. | |
| 2007/0207528 A1 | 9/2007 | Picataggio et al. | |
| 2008/0194685 A1 | 8/2008 | Damude et al. | |
| 2008/0254195 A1 | 10/2008 | Damude et al. | |

FOREIGN PATENT DOCUMENTS

| | | |
|---|---|---|
| WO | WO02077213 | 10/2002 |
| WO | WO2004057001 | 7/2004 |
| WO | WO2005012316 | 2/2005 |
| WO | WO2005083093 | 9/2005 |
| WO | WO2007061742 | 5/2007 |
| WO | WO2007061845 | 5/2007 |

OTHER PUBLICATIONS

GenBank Accession No. AAL37626.
The Following applications are commonly owned by DuPont and are reported herein: U.S. Appl. No. 12/244,950, filed Oct. 3, 2008 and U.S. Appl. No. 12/244,822, filed Oct. 3, 2008.
Sheveleva et al., "identification and Comparative Analysis of the chloroplast Alpha-Subunit Gene of DNA-Dependent RNA Polymerase from Seven Euglena Species", Nucleic Acids Research, vol. 30, No. 5, Mar. 1, 2002, pp. 1247-1254, XP002489662, ISSN: 0305-1048, p. 1247, col. 2, last paragraph—p. 1248, col. 1, line 3.
International Search Report and Written Opinion for PCT/US2008/060396 mailed Aug. 6, 2008.

*Primary Examiner* — Shin-lin Chen

(57) ABSTRACT

The present invention relates to Δ9 elongases, which have the ability to convert linoleic acid (LA; 18:2 ω-6) to eicosadienoic acid (EDA; 20:2 ω-6) and/or α-linolenic acid (ALA; 18:3 ω-3) to eicosatrienoic acid (ETrA; 20:3 ω-3). Isolated nucleic acid fragments and recombinant constructs comprising such fragments encoding Δ9 elongases along with a method of making long-chain polyunsaturated fatty acids (PUFAs) using these Δ9 elongases in oleaginous yeast are disclosed.

8 Claims, 6 Drawing Sheets

Δ-9 ELONGASES AND THEIR USE IN MAKING POLYUNSATURATED FATTY ACIDS

CROSS REFERENCE TO RELATED APPLICATIONS

This application is a division application of U.S. patent application Ser. No. 12/102,879 filed Apr. 15, 2008, granted as U.S. Pat. No. 7,794,701 on Sep. 14, 2010, which claims the benefit of U.S. Provisional Application No. 60/911,925, filed Apr. 16, 2007, now abandoned, the entire contents of which are herein incorporated by reference in their entirety.

FIELD OF THE INVENTION

This invention is in the field of biotechnology. More specifically, this invention pertains to the identification of polynucleotide sequences encoding Δ9 fatty acid elongases and the use of these elongases in making long-chain polyunsaturated fatty acids (PUFAs).

BACKGROUND OF THE INVENTION

Today, a variety of different hosts including plants, algae, fungi, stramenopiles and yeast are being investigated as means for commercial PUFA production. Genetic engineering has demonstrated that the natural abilities of some hosts (even those natively limited to linoleic acid (LA; 18:2 ω-6) and α-linolenic acid (ALA; 18:3 ω-3) fatty acid production) can be substantially altered to result in high-level production of various long-chain ω-3/ω-6 PUFAs. Whether this is the result of natural abilities or recombinant technology, production of arachidonic acid (ARA; 20:4 ω-6), eicosapentaenoic acid (EPA; 20:5 ω-3) and docosahexaenoic acid (DHA; 22:6 ω-3) may require expression of a Δ9 elongase.

Most Δ9 elongase enzymes identified so far have the ability to convert both LA to eicosadienoic acid (EDA; 20:2 ω-6) and ALA to eicosatrienoic acid (ETrA; 20:3 ω-3) (wherein dihomo-γ-linolenic acid (DGLA; 20:3 ω-6) and eicosatetraenoic acid (ETA; 20:4 ω-3) are subsequently synthesized from EDA and ETrA, respectively, following reaction with a Δ8 desaturase; ARA and EPA are subsequently synthesized from DGLA and ETA, respectively, following reaction with a Δ5 desaturase; and, DHA synthesis requires subsequent expression of an additional $C_{20/22}$ elongase and a Δ4 desaturase).

In spite of the need for new methods for the production of ARA, EPA and DHA, few Δ9 elongase enzymes have been identified. A Δ9 elongase from *Isochrysis galbana* is publicly available (described in GenBank Accession No. AAL37626, as well as PCT Publications No. WO 02/077213, No. WO 2005/083093, No. WO 2005/012316 and No. WO 2004/057001). PCT Publications No. WO 2007/061845 and No. WO 2007/061742 (Applicants' Assignee's co-pending applications), disclose Δ9 elongases from *Euglena gracilis* and *Eutreptiella* sp. CCMP389, as well as Δ9 elongase motifs.

Thus, there is need for the identification and isolation of additional genes encoding Δ9 elongases that will be suitable for heterologous expression in a variety of host organisms for use in the production of ω-3/ω-6 fatty acids.

Applicants have solved the stated problem by isolating genes encoding Δ9 fatty acid elongases from *Euglena anabaena*.

SUMMARY OF THE INVENTION

The present invention relates to new genetic constructs encoding polypeptides having Δ9 elongase activity, and their use in algae, bacteria, yeast, euglenoids, stramenopiles and fungi for the production of PUFAs. Accordingly the invention provides a microbial host cell comprising an isolated polynucleotide comprising:

(a) a nucleotide sequence encoding a polypeptide having Δ9 elongase activity, wherein the polypeptide has at least 80% amino acid identity, based on the Clustal V method of alignment, when compared to an amino acid sequence as set forth in SEQ ID NO:13 or SEQ ID NO:14;

(b) a nucleotide sequence encoding a polypeptide having 49 elongase activity, wherein the nucleotide sequence has at least 80% sequence identity, based on the BLASTN method of alignment, when compared to a nucleotide sequence as set forth in SEQ ID NO:11, SEQ ID NO:12 or SEQ ID NO:26;

(c) a nucleotide sequence encoding a polypeptide having Δ9 elongase activity, wherein the nucleotide sequence hybridizes under stringent conditions to a nucleotide sequence as set forth in SEQ ID NO:11, SEQ ID NO:12 or SEQ ID NO:26; or (d) a complement of the nucleotide sequence of (a), (b) or (c), wherein the complement and the nucleotide sequence consist of the same number of nucleotides and are 100% complementary.

In another embodiment the invention provides a method for the production of eicosadienoic acid comprising:
a) providing a microbial host cell comprising:
   (i) a recombinant nucleotide molecule encoding a Δ9 elongase polypeptide having at least 80% amino acid identity, based on the Clustal V method of alignment, when compared to an amino acid sequence as set forth in SEQ ID NO:13 or SEQ ID NO:14; and,
   (ii) a source of linoleic acid;
b) growing the microbial host cell of step (a) under conditions wherein the nucleic acid fragment encoding the Δ9 elongase polypeptide is expressed and the linoleic acid is converted to eicosadienoic acid; and,
c) optionally recovering the eicosadienoic acid of step (b).

In an additional embodiment the invention provides a method for the production of eicosatrienoic acid comprising:
a) providing a microbial host cell comprising:
   (i) a recombinant nucleotide molecule encoding a Δ9 elongase polypeptide having at least 80% amino acid identity, based on the Clustal V method of alignment, when compared to an amino acid sequence as set forth in SEQ ID NO:13 or SEQ ID NO:14; and,
   (ii) a source of α-linolenic acid;
b) growing the microbial host cell of step (a) under conditions wherein the nucleic acid fragment encoding the Δ9 elongase polypeptide is expressed and the α-linolenic acid is converted to eicosatrienoic acid; and,
c) optionally recovering the eicosatrienoic acid of step (b).

In another embodiment the invention provides an isolated nucleic acid molecule which encodes a Δ9 elongase as set forth in SEQ ID NO:26 wherein at least 98 codons are codon-optimized for expression in *Yarrowia* sp.

BRIEF DESCRIPTION OF THE DRAWINGS AND SEQUENCE LISTINGS

Figure 3:
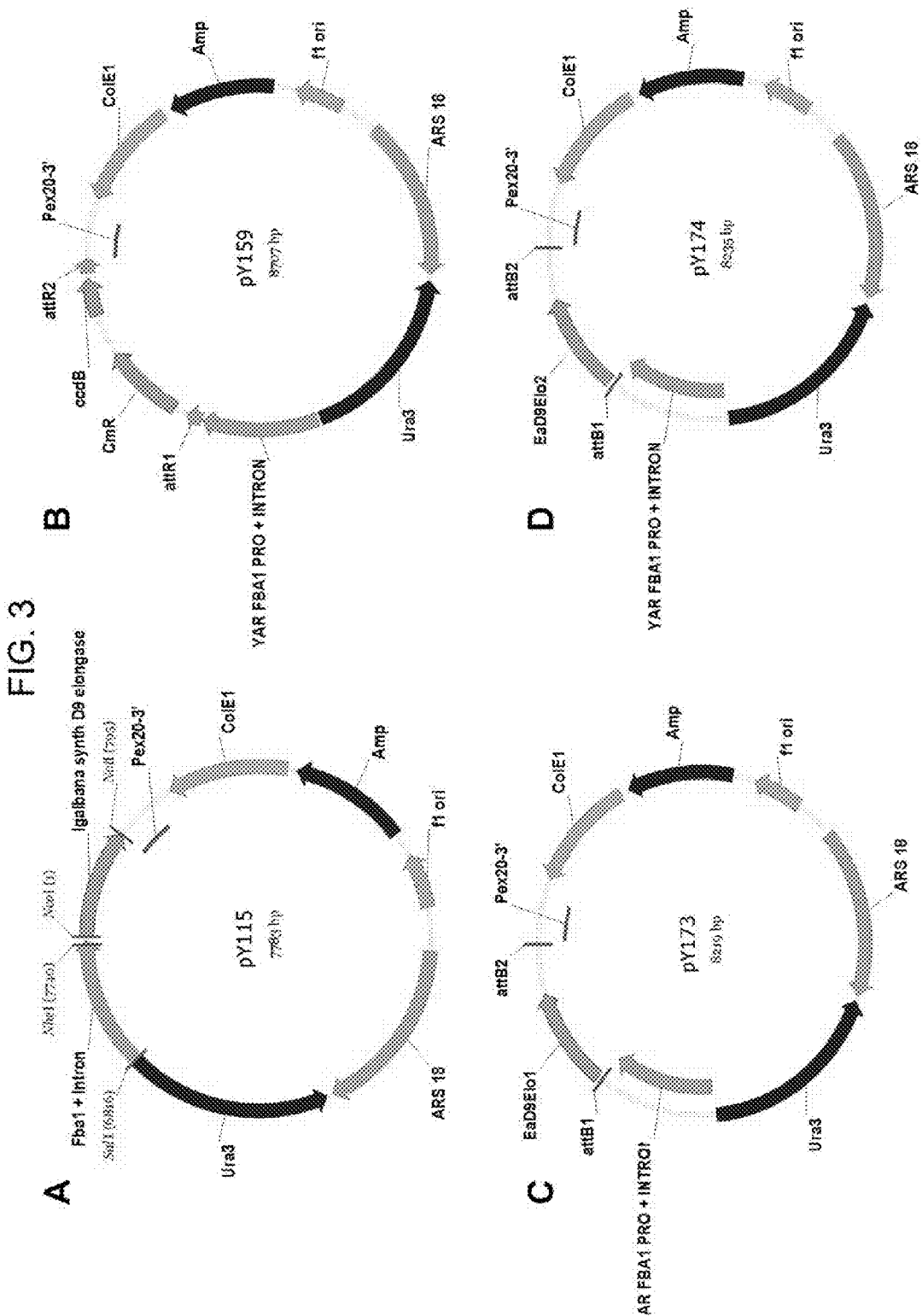

FIG. 3 provides plasmid maps for the following: (A) pY115 (SEQ ID NO:19); (B) pY159 (SEQ ID NO:23); (C) pY173 (SEQ ID NO:24); and, (D) pY174 (SEQ ID NO:25).

Figure 4A:
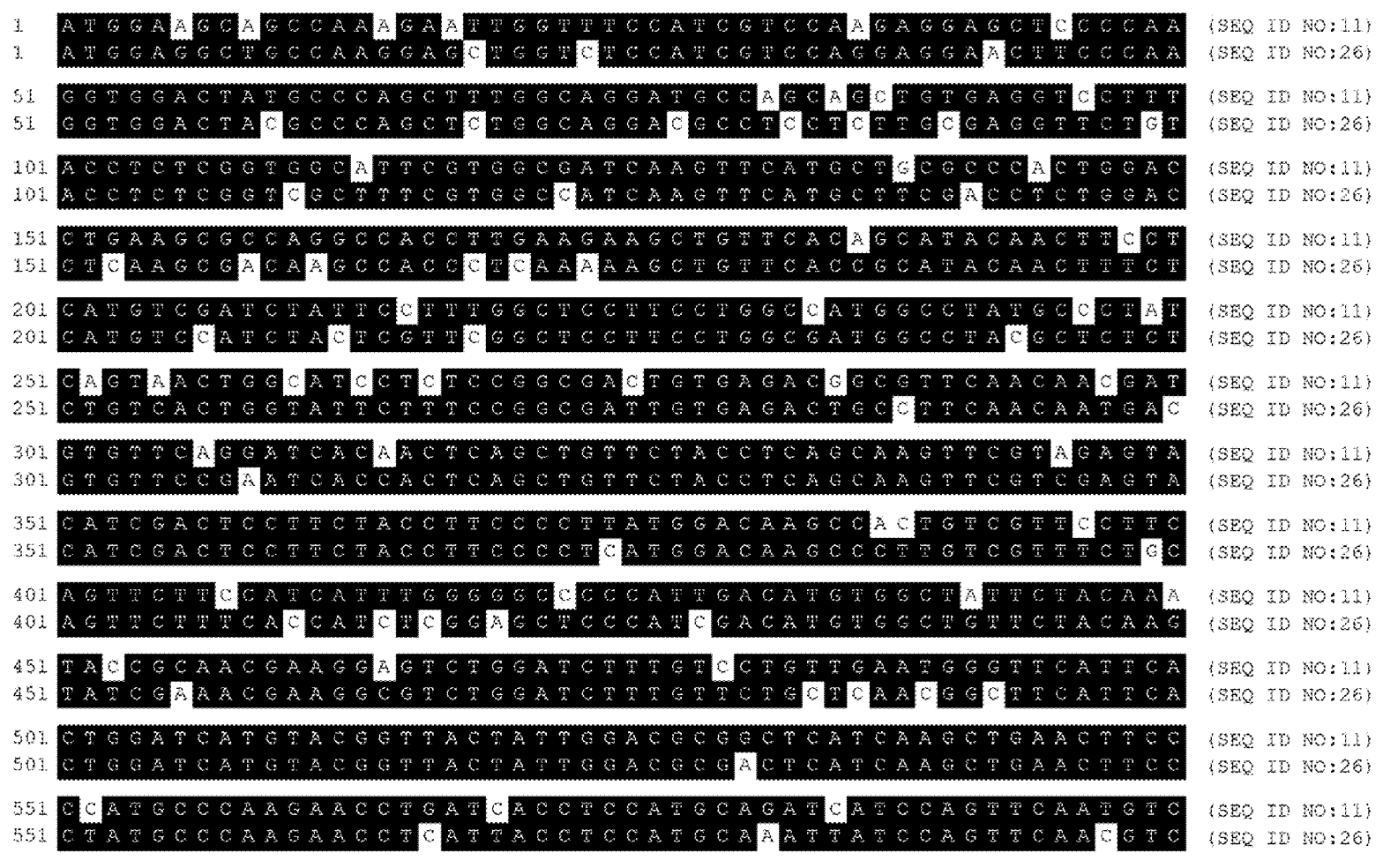
Figure 4B:
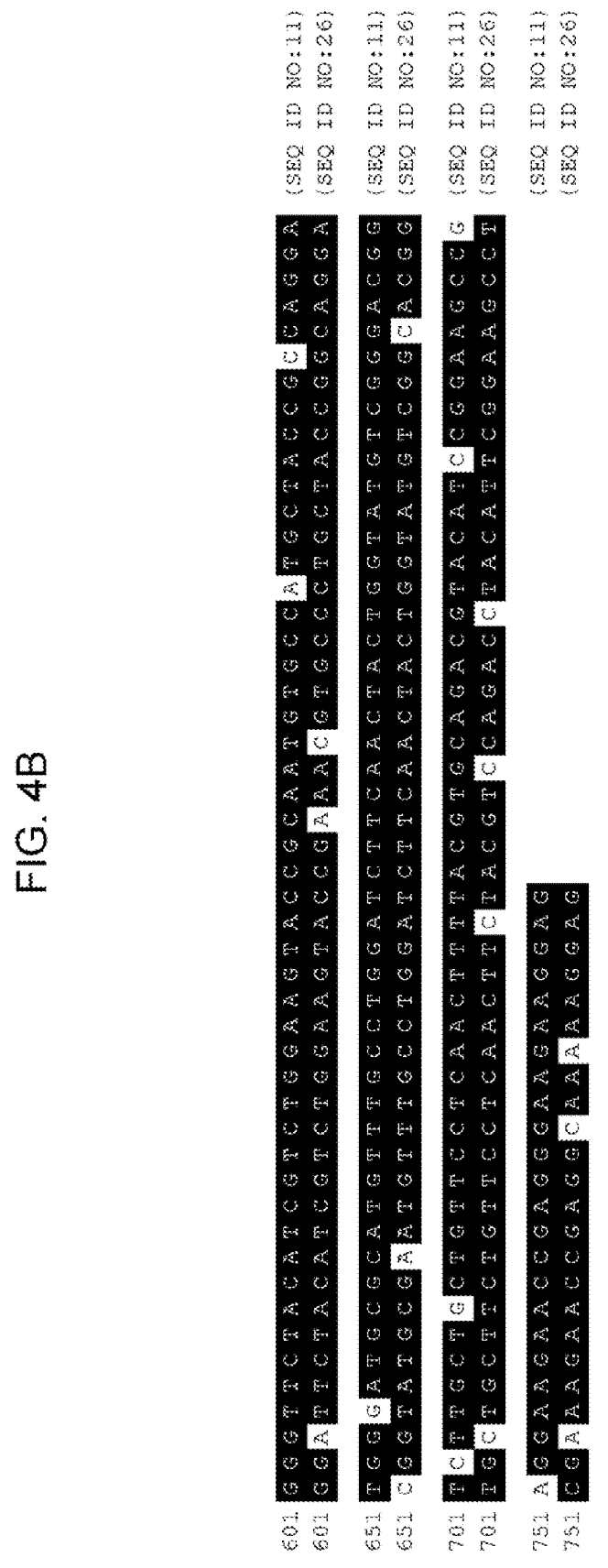

FIGS. 4A and 4B show a comparison of the nucleotide sequences of EaD9Elo (SEQ ID NO:11) and EaD9ES (SEQ ID NO:26).

Figure 5:
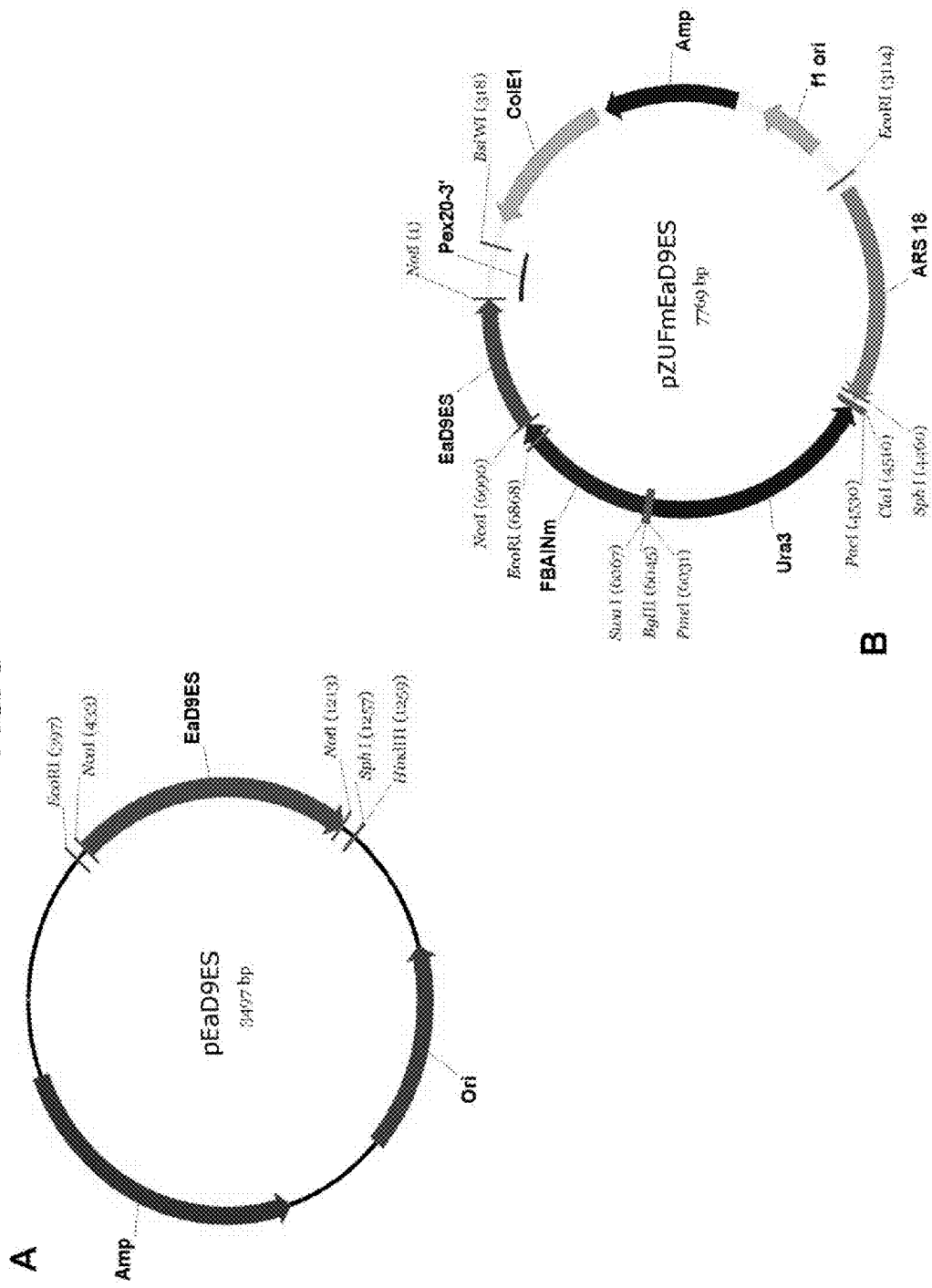

FIG. 5 provides plasmid maps for the following: (A) pEaD9ES (SEQ ID NO:28); and, (B) pZUFmEaD9eS (SEQ ID NO:29).

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-4, 9-19 and 22-29 are ORFs encoding genes or proteins (or portions thereof), or plasmids, as identified in Table 1.

TABLE 1

Summary Of Nucleic Acid And Protein SEQ ID Numbers

| Description and Abbreviation | Nucleic acid SEQ ID NO. | Protein SEQ ID NO. |
|---|---|---|
| *Euglena anabaena* Δ9 elongase cDNA sequence ("EaD9Elo1") | 1 (1129 bp) | — |
| *Euglena anabaena* Δ9 elongase cDNA sequence ("EaD9Elo2") | 2 (1145 bp) | — |
| *Euglena gracilis* Δ9 elongase coding sequence ("EgD9e") | 3 (774 bp) | 4 (258 AA) |
| Plasmid pLF121-1 | 9 (3668 bp) | — |
| Plasmid pLF121-2 | 10 (3684 bp) | — |
| *Euglena anabaena* Δ9 elongase coding sequence ("EaD8Des1 CDS" or "EaD9Elo1", respectively) | 11 (774 bp) | 13 (258 AA) |
| *Euglena anabaena* Δ9 elongase coding sequence ("EaD8Des2 CDS" or "EaD9Elo2", respectively) | 12 (774 bp) | 14 (258 AA) |
| Plasmid pKR906 | 15 (4311 bp) | — |
| *Isochrysis galbana* Δ9 elongase (IgD9e) | — | 16 (263 AA) |
| Plasmid pDMW263 | 17 (9472 bp) | — |
| Plasmid pDMW237 | 18 (7879 bp) | — |
| Plasmid pY115 | 19 (7783 bp) | — |
| Plasmid pY158 | 22 (6992 bp) | — |
| Plasmid pY159 | 23 (8707 bp) | — |
| Plasmid pY173 | 24 (8219 bp) | — |
| Plasmid pY174 | 25 (8235 bp) | — |
| Synthetic Δ9 elongase, derived from *Euglena anabaena*, codon-optimized for expression in *Yarrowia lipolytica* ("EaD9eS") | 26 (774 bp) | 27 (258 AA) |
| Plasmid pEaD9ES | 28 (3497 bp) | — |
| Plasmid pZUFmEaD9eS | 29 (7769 bp) | — |

SEQ ID NOs:5 and 6 correspond to oligonucleotides oEugEL1-1 and oEugEL1-2, respectively, used for amplification of the *Euglena gracilis* Δ9 elongase.

SEQ ID NOs:7 and 8 correspond to the M13F universal primer and primer M13-28Rev, respectively, used for end-sequencing of *Euglena anabaena* DNA inserts.

SEQ ID NOs:20 and 21 correspond to primers oYFBA1 and oYFBA1-6, respectively, used to amplify the FBAINm promoter from plasmid pY115.

DETAILED DESCRIPTION OF THE INVENTION

New *Euglena anabaena* Δ9 elongase enzymes and genes encoding the same that may be used for the manipulation of biochemical pathways for the production of healthful PUFAs are disclosed herein.

PUFAs, or derivatives thereof, are used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary).

DEFINITIONS

In the context of this disclosure, a number of terms and abbreviations are used. The following definitions are provided.

"Open reading frame" is abbreviated ORF.
"Polymerase chain reaction" is abbreviated PCR.
"American Type Culture Collection" is abbreviated ATCC.
"Polyunsaturated fatty acid(s)" is abbreviated PUFA(s).
"Triacylglycerols" are abbreviated TAGs.

The term "invention" or "present invention" as used herein is not meant to be limiting to any one specific embodiment of the invention but applies generally to any and all embodiments of the invention as described in the claims and specification.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in U.S. Pat. No. 7,238,482.

Fatty acids are described herein by a simple notation system of "X:Y", where X is the total number of carbon (C) atoms in the particular fatty acid and Y is the number of double bonds. The number following the fatty acid designation indicates the position of the double bond from the carboxyl end of the fatty acid with the "c" affix for the cis-configuration of the double bond (e.g., palmitic acid (16:0), stearic acid (18:0), oleic acid (18:1, 9c), petroselinic acid (18:1, 6c), LA (18:2, 9c,12c), GLA (18:3, 6c,9c,12c) and ALA (18:3, 9c,12c,15c)). Unless otherwise specified, 18:1, 18:2 and 18:3 refer to oleic, LA and ALA fatty acids, respectively. If not specifically written as otherwise, double bonds are assumed to be of the cis configuration. For instance, the double bonds in 18:2 (9,12) would be assumed to be in the cis configuration.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the remainder of the specification, and each compounds' chemical name.

TABLE 2

Nomenclature of Polyunsaturated Fatty Acids and Precursors

| Common Name | Abbreviation | Chemical Name | Shorthand Notation |
|---|---|---|---|
| Myristic | — | tetradecanoic | 14:0 |
| Palmitic | PA or Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linolenic | GLA | cis-6,9,12-octadecatrienoic | 18:3 ω-6 |
| Eicosadienoic | EDA | cis-11,14-eicosadienoic | 20:2 ω-6 |
| Dihomo-γ-linolenic | DGLA | cis-8,11,14-eicosatrienoic | 20:3 ω-6 |
| Sciadonic | SCI | cis-5,11,14-eicosatrienoic | 20:3b ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA or ERA | cis-11,14,17-eicosatrienoic | 20:3 ω-3 |
| Eicosa-tetraenoic | ETA | cis-8,11,14,17-eicosatetraenoic | 20:4 ω-3 |
| Juniperonic | JUP | cis-5,11,14,17-eicosatrienoic | 20:4b ω-3 |
| Eicosa-pentaenoic | EPA | cis-5,8,11,14,17-eicosapentaenoic | 20:5 ω-3 |
| Docosatrienoic | DRA | cis-10,13,16-docosatrienoic | 22:3 ω-6 |
| Docosa-tetraenoic | DTA | cis-7,10,13,16-docosatetraenoic | 22:4 ω-6 |
| Docosa-pentaenoic | DPAn-6 | cis-4,7,10,13,16-docosapentaenoic | 22:5 ω-6 |
| Docosa-pentaenoic | DPA | cis-7,10,13,16,19-docosapentaenoic | 22:5 ω-3 |

TABLE 2-continued

Nomenclature of Polyunsaturated Fatty Acids and Precursors

| Common Name | Abbreviation | Chemical Name | Shorthand Notation |
|---|---|---|---|
| Docosa-hexaenoic | DHA | cis-4,7,10,13,16,19-docosahexaenoic | 22:6 ω-3 |

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to ω-6 fatty acids such as LA, EDA, GLA, DGLA, ARA, DRA, DTA and DPAn-6 and ω-3 fatty acids such as ALA, STA, ETrA, ETA, EPA, DPA and DHA. This process is well described in the literature (e.g., see PCT Publication No. WO 2006/052870). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzyme" refers to any of the following enzymes (and genes which encode said enzymes) associated with the biosynthesis of a PUFA, including: a Δ9 elongase, a $C_{14/16}$ elongase, a $C_{16/18}$ elongase, a $C_{18/20}$ elongase, a $C_{20/22}$ elongase, a Δ4 desaturase, a Δ5 desaturase, a Δ6 desaturase, a Δ12 desaturase, a Δ15 desaturase, a Δ17 desaturase, a Δ9 desaturase and/or a Δ8 desaturase.

Figure 1:
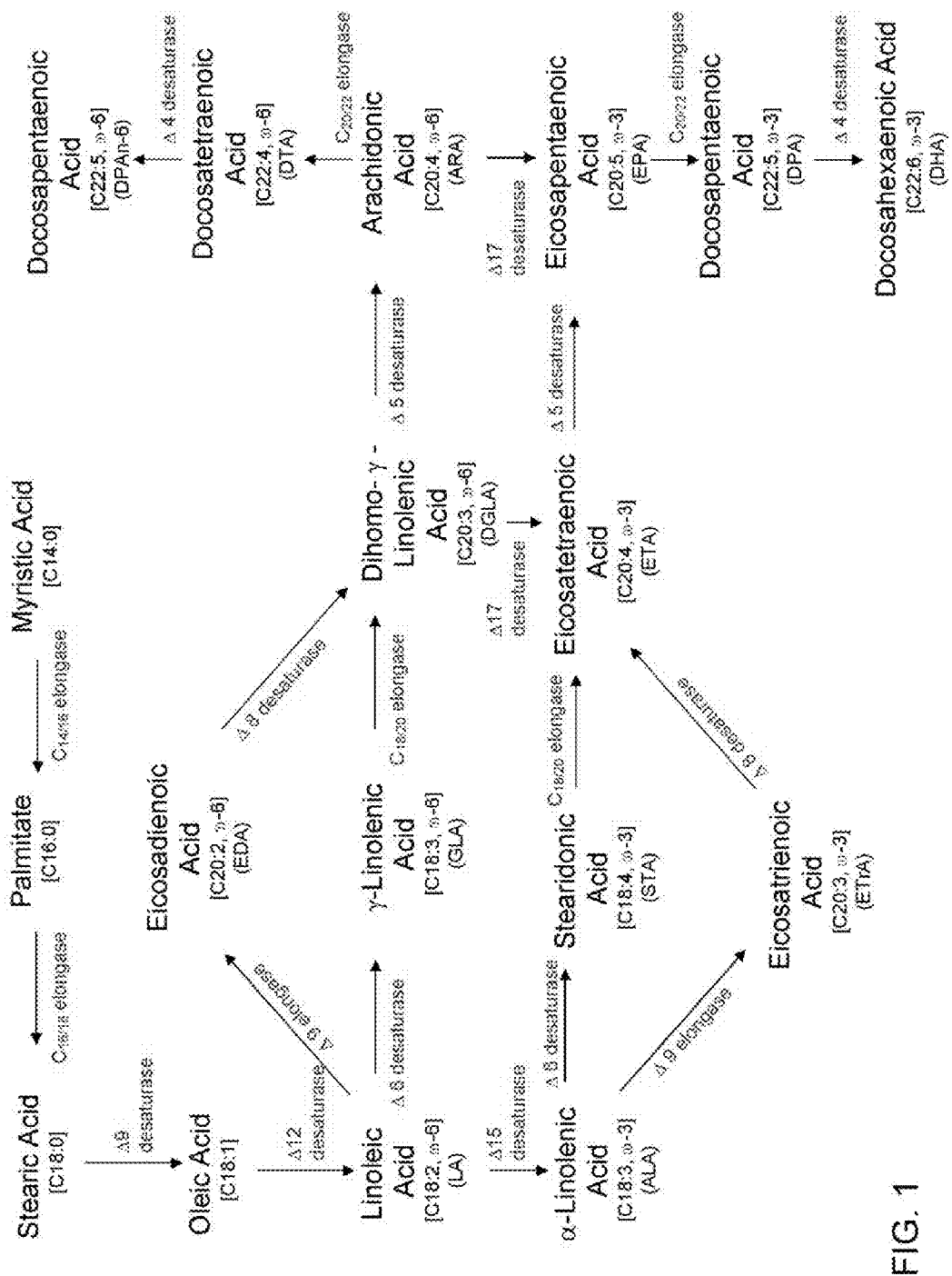
FIG. 1 is a representative ω-3 and ω-6 fatty acid biosynthetic pathway providing for the conversion of myristic acid through various intermediates to DHA.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIG. 1, providing for the conversion of myristic acid through various intermediates to DHA, which demonstrates how both ω-3 and ω-6 fatty acids may be produced from a common source. The pathway is naturally divided into two portions where one portion will generate ω-3 fatty acids and the other portion, ω-6 fatty acids.

The term "functional" as used herein in context with the ω-3/ω-6 fatty acid biosynthetic pathway means that some (or all) of the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the PUFA biosynthetic pathway enzyme genes are required, as a number of fatty acid products will only require the expression of a subset of the genes of this pathway.

The term "Δ6 desaturase/Δ6 elongase pathway" will refer to a PUFA biosynthetic pathway that minimally includes at least one Δ6 desaturase and at least one $C_{18/20}$ elongase (also referred to as a Δ6 elongase), thereby enabling biosynthesis of DGLA and/or ETA from LA and ALA, respectively, with GLA and/or STA as intermediate fatty acids. With expression of other desaturases and elongases, ARA, EPA, DPA and DHA may also be synthesized.

The term "Δ9 elongase/Δ8 desaturase pathway" will refer to a PUFA biosynthetic pathway that minimally includes at least one Δ9 elongase and at least one Δ8 desaturase, thereby enabling biosynthesis of DGLA and/or ETA from LA and ALA, respectively, with EDA and/or ETrA as intermediate fatty acids. With expression of other desaturases and elongases, ARA, EPA, DPA and DHA may also be synthesized.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the Δ9 elongase/Δ8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the Δ9 elongase/Δ8 desaturase pathway, sciadonic acid (SCI) and juniperonic acid (JUP) also can be produced by the action of a Δ5 desaturase on either EDA or ETrA, respectively. They are considered to be "by-product fatty acids" since neither can be further converted to EPA by the action of other metabolic pathway enzymes.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Desaturases of interest include, for example: (1) Δ8 desaturases that desaturate a fatty acid between the eighth and ninth carbon atom numbered from the carboxyl-terminal end of the molecule and that can, for example, catalyze the conversion of EDA to DGLA and/or ETrA to ETA; (2) Δ5 desaturases that catalyze the conversion of DGLA to ARA and/or ETA to EPA; (3) Δ6 desaturases that catalyze the conversion of LA to GLA and/or ALA to STA; (4) Δ4 desaturases that catalyze the conversion of DPA to DHA and/or DTA to DPAn-6; (5) Δ12 desaturases that catalyze the conversion of oleic acid to LA; (6) Δ15 desaturases that catalyze the conversion of LA to ALA and/or GLA to STA; (7) Δ17 desaturases that catalyze the conversion of ARA to EPA and/or DGLA to ETA; and, (8) Δ9 desaturases that catalyze the conversion of palmitic acid to palmitoleic acid (16:1) and/or stearic acid to oleic acid (18:1). In the art, Δ15 and Δ17 desaturases are also occasionally referred to as "omega-3 desaturases", "w-3 desaturases" and/ or "ω-3 desaturases", based on their ability to convert ω-6 fatty acids into their ω-3 counterparts (e.g., conversion of LA into ALA and ARA into EPA, respectively). In some embodiments, it may be desirable to empirically determine the specificity of a particular fatty acid desaturase by transforming a suitable host with the gene for the fatty acid desaturase and determining its effect on the fatty acid profile of the host.

For the purposes herein, an enzyme catalyzing the first condensation reaction (i.e., conversion of malonyl-CoA and long-chain acyl-CoA to -ketoacyl-CoA) will be referred to generically as an "elongase". In general, the substrate selectivity of elongases is somewhat broad but segregated by both chain length and the degree of unsaturation. Accordingly, elongases can have different specificities. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase (also known as a Δ6 elongase as the terms can be used interchangeably) will utilize a $C_{18}$ substrate (e.g., GLA, STA) and a $C_{20/22}$ elongase will utilize a $C_{20}$ substrate (e.g., ARA, EPA). In like manner, and of particular interest herein, a "Δ9 elongase" catalyzes the conversion of LA to EDA and/or ALA to ETrA. It is important to note that some elongases have broad specificity and thus a single enzyme may be capable of catalyzing several elongase reactions. Thus, for example, a Δ9 elongase may also act as a $C_{16/18}$ elongase, $C_{18/20}$ elongase and/or $C_{20/22}$ elongase and may have alternate, but not preferred, specificities for Δ5 and Δ6 fatty acids such as EPA and/or GLA, respectively. In preferred embodiments, it may be desirable to empirically determine the specificity of a fatty acid elongase by transforming a suitable host with the gene for the fatty acid elongase and determining its effect on the fatty acid profile of the host. Elongase systems generally comprise four enzymes that are responsible for elongation of a fatty acid carbon chain to produce a fatty acid that is two carbons longer than the fatty acid substrate that the elongase system acts upon. More specifically, the process of elongation occurs in association with fatty acid synthase, whereby CoA is the acyl carrier (Lassner et al., *Plant Cell*, 8:281-292 (1996)). In the first step, which has been found to be both substrate-specific and also rate-limiting, malonyl-CoA is condensed with a long-chain acyl-CoA to yield carbon dioxide ($CO_2$) and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongase systems are the conversion of GLA to DGLA, STA to ETA, LA to EDA, ALA to ETrA, ARA to DTA and EPA to DPA.

For the purposes herein, the term "EaD9Elo1" refers to a Δ9 elongase enzyme (SEQ ID NO:13) isolated from *Euglena anabaena*, encoded by SEQ ID NO:11 herein. The term "EaD9Elo2" refers to a Δ9 elongase enzyme (SEQ ID NO:14) isolated from *E. anabaena*, encoded by SEQ ID NO:12 herein. Likewise, the term "EaD9eS" refers to a synthetic Δ9 elongase derived from *E. anabaena* that is codon-optimized for expression in *Yarrowia lipolytica* (i.e., SEQ ID NOs:26 and 27).

The terms "conversion efficiency" and "percent substrate conversion" refer to the efficiency by which a particular enzyme (e.g., an elongase) can convert substrate to product. The conversion efficiency is measured according to the following formula: ([product]/[substrate+product])*100, where 'product' includes the immediate product and all products in the pathway derived from it.

The term "oleaginous" refers to those organisms that tend to store their energy source in the form of lipid (Weete, In: Fungal Lipid Biochemistry, $2^{nd}$ Ed., Plenum, 1980). Within oleaginous microorganisms the cellular oil or TAG content generally follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil.

The term "oleaginous yeast" refers to those microorganisms classified as yeasts that make oil. Examples of oleaginous yeast include, but are no means limited to, the following genera: *Yarrowia, Candida, Rhodotorula, Rhodosporidium, Cryptococcus, Trichosporon* and *Lipomyces*.

The term "Euglenophyceae" refers to a group of unicellular colorless or photosynthetic flagellates ("euglenoids") found living in freshwater, marine, soil, and parasitic environments. The class is characterized by solitary unicells, wherein most are free-swimming and have two flagella (one of which may be nonemergent) arising from an anterior invagination known as a reservoir. Photosynthetic euglenoids contain one to many chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: *Euglena, Eutreptiella* and *Tetruetreptia*.

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and refer to a polymer of RNA or DNA that is single- or double-stranded, optionally containing synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridlate, "T" for deosythymidylate, "R" for purines (A or G), "Y" for pyrimidiens (C or T), "K" for G or T, "H" for A or C or T, "I" for inosine, and "N" for any nucleotide.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family. PCT Publications No. WO 2007/061845 and No. WO 2007/061742 describe seven distinct motifs that are associated with Δ9 elongases.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the important factors being the ionic strength and temperature of the final wash solution. For DNA-DNA hybrids, the $T_m$ can be approximated from the equation of Meinkoth et al., *Anal. Biochem.*, 138:267-284 (1984): $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); and, low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120 or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS*, 5:151-153 (1989); Higgins, D. G. et al., *Comput. Appl. Biosci.*, 8:189-191 (1992)) and found in the MegAlign™ program of the LASERGENE bioinformatics computing suite (supra). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant euglenoid polypeptides as set forth in SEQ ID NO:13 and SEQ ID NO:14. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed at almost all stages of development, are commonly referred to as "constitutive promoters". It is further recognized that since in most cases the exact boundaries of regulatory sequences, especially at its 5' end, have not been completely defined, DNA fragments of some variation may have identical promoter activity.

A promoter sequence may consist of proximal and more distal upstream elements, the latter elements often referred to as enhancers and/or silencers. Accordingly, an "enhancer" is a DNA sequence that can stimulate promoter activity, and may be an innate element of the promoter or a heterologous element inserted to enhance the level or stage-specific activity of a promoter. A "silencer" is a DNA sequence that can repress promoter activity, and may be an innate element of the promoter or a heterologous element inserted to repress the level or stage-specific activity of a promoter.

"Translation leader sequence" refers to a polynucleotide sequence located between the transcription start site of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Mol. Biotechnol., 3:225-236 (1995)).

The terms "3' non-coding sequences", "transcription terminator" and "termination sequences" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in a sense or antisense orientation.

The term "recombinant" refers to an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA derived from the nucleic acid fragments of the invention. Expression may also refer to translation of mRNA into a protein (either precursor or mature).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: (1) a promoter sequence; (2) a coding sequence (i.e., ORF); and, (3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

A "recombinant DNA construct" (also referred to interchangeably herein as a "expression construct" and "construct") comprises an artificial combination of nucleic acid fragments, e.g., regulatory and coding sequences that are not found together in nature. For example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.*, 4:2411-2418 (1985); De Almeida et al., *Mol. Gen. Genetics,* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "introduced" means providing a nucleic acid (e.g., expression cassette) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct or expression cassette) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

As used herein, "transgenic" refers to a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression cassette. Transgenic is used herein to include any cell or cell line, the genotype of which has been altered by the presence of heterologous nucleic acids including those transgenics initially so altered as well as those created by mating from the initial transgenic with different mating types. The term "transgenic" as used herein does not encompass the alteration of the genome (chromosomal or extra-chromosomal) by naturally occurring events such as random cross-fertilization, non-recombinant viral infection, non-recombinant bacterial transformation, non-recombinant transposition, or spontaneous mutation.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987). Transformation methods are well known to those skilled in the art and are described infra. *An Overview: Microbial Biosynthesis Of Fatty Acids And Triacylglycerols*

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in U.S. Pat. No. 7,238, 482. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: (1) the esterification of one molecule of acyl-CoA to glycerol-3-phosphate via an acyltransferase to produce lysophosphatidic acid; (2) the esterification of a second molecule of acyl-CoA via an acyltransferase to yield 1,2-diacylglycerol phosphate (commonly identified as phosphatidic acid); (3) removal of a phosphate by phosphatidic acid phosphatase to yield 1,2-diacylglycerol (DAG); and, (4) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to $\omega$-3/$\omega$-6 fatty acids involves elongation of the carbon chain through the addition of carbon atoms and desaturation of the molecule through the addition of double bonds. This requires a series of special desaturation and elongation enzymes present in the endoplasmic reticulim membrane. However, as seen in FIG. 1 and as described below, there are often multiple alternate pathways for production of a specific $\omega$-3/$\omega$-6 fatty acid.

Specifically, all pathways require the initial conversion of oleic acid to LA, the first of the ω-6 fatty acids, by a Δ12 desaturase. Then, using the "Δ9 elongase/Δ8 desaturase pathway" and LA as substrate, long chain ω-6 fatty acids are formed as follows: (1) LA is converted to EDA by a Δ9 elongase; (2) EDA is converted to DGLA by a Δ8 desaturase; (3) DGLA is converted to ARA by a Δ5 desaturase; (4) ARA is converted to DTA by a $C_{20/22}$ elongase; and, (5) DTA is converted to DPAn-6 by a Δ4 desaturase. Alternatively, the "Δ9 elongase/Δ8 desaturase pathway" can use ALA as substrate to produce long chain ω-3 fatty acids as follows: (1) LA is converted to ALA, the first of the ω-3 fatty acids, by a Δ15 desaturase; (2) ALA is converted to ETrA by a Δ9 elongase; (3) ETrA is converted to ETA by a Δ8 desaturase; (4) ETA is converted to EPA by a Δ5 desaturase; (5) EPA is converted to DPA by a $C_{20/22}$ elongase; and, (6) DPA is converted to DHA by a Δ4 desaturase. Optionally, ω-6 fatty acids may be converted to ω-3 fatty acids; for example, ALA is produced from LA by Δ15 desaturase activity; ETA and EPA are produced from DGLA and ARA, respectively, by Δ17 desaturase activity.

Alternate pathways for the biosynthesis of ω-3/ω-6 fatty acids utilize a Δ6 desaturase and $C_{18/20}$ elongase (i.e., the "Δ6 desaturase/Δ6 elongase pathway"). More specifically, LA and ALA may be converted to GLA and STA, respectively, by a Δ6 desaturase; then, a $C_{18/20}$ elongase converts GLA to DGLA and/or STA to ETA. Downstream PUFAs are subsequently formed as described above.

It is contemplated that the particular functionalities required to be introduced into a specific host organism for production of ω-3/ω-6 fatty acids will depend on the host cell (and its native PUFA profile and/or desaturase/elongase profile), the availability of substrate, and the desired end product(s). For example, expression of the Δ9 elongase/Δ8 desaturase pathway may be preferred in some embodiments, as opposed to expression of the Δ6 desaturase/Δ6 elongase pathway, since PUFAs produced via the former pathway are devoid of GLA and/or STA.

One skilled in the art will be able to identify various candidate genes encoding each of the enzymes desired for ω-3/ω-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: (1) the substrate specificity of the polypeptide; (2) whether the polypeptide or a component thereof is a rate-limiting enzyme; (3) whether the desaturase or elongase is essential for synthesis of a desired PUFA; (4) co-factors required by the polypeptide; and/or, (5) whether the polypeptide was modified after its production (e.g., by a kinase or a prenyltransferase). The expressed polypeptide preferably has parameters compatible with the biochemical environment of its location in the host cell (see U.S. Pat. No. 7,238,482 for additional details).

In additional embodiments, it will also be useful to consider the conversion efficiency of each particular desaturase and/or elongase. More specifically, since each enzyme rarely functions with 100% efficiency to convert substrate to product, the final lipid profile of unpurified oils produced in a host cell will typically be a mixture of various PUFAs consisting of the desired ω-3/ω-6 fatty acid, as well as various upstream intermediary PUFAs. Thus, each enzyme's conversion efficiency is also a variable to consider, when optimizing biosynthesis of a desired fatty acid.

With each of the considerations above in mind, candidate genes having the appropriate desaturase and elongase activities (e.g., Δ6 desaturases, $C_{18/20}$ elongases, Δ5 desaturases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Sequence Identification of Novel Δ9 Elongases

In the present invention, nucleotide sequences encoding Δ9 elongases have been isolated from *Euglena anabaena*, as summarized below in Table 3.

TABLE 3

Summary Of *Euglena anabaena* Δ9 Elongases

| Abbreviation | Nucleotide SEQ ID NO | Amino Acid SEQ ID NO |
|---|---|---|
| EaD9Elo1 | 11 | 13 |
| EaD9Elo2 | 12 | 14 |
| EaD9eS | 26 | 27 |

*Note:
SEQ ID NO: 27 is identical in sequence to SEQ ID NO: 13

Thus, the present invention concerns an isolated polynucleotide comprising:

(a) a nucleotide sequence encoding a polypeptide having Δ9 elongase activity, wherein the polypeptide has at least 80% amino acid identity, based on the Clustal V method of alignment, when compared to an amino acid sequence as set forth in SEQ ID NO:13 or SEQ ID NO:14;

(b) a nucleotide sequence encoding a polypeptide having Δ9 elongase activity, wherein the nucleotide sequence has at least 80% sequence identity, based on the BLASTN method of alignment, when compared to a nucleotide sequence as set forth in SEQ ID NO:11, SEQ ID NO:12 or SEQ ID NO:26; or, (c) a complement of the nucleotide sequence of (a) or (b), wherein the complement and the nucleotide sequence consist of the same number of nucleotides and are 100% complementary.

In still another aspect, this invention concerns an isolated polynucleotide comprising a nucleotide sequence encoding a polypeptide having Δ9 elongase activity, wherein the nucleotide sequence has at least 90% sequence identity, based on the BLASTN method of alignment, when compared to a nucleotide sequence as set forth in SEQ ID NO:11, SEQ ID NO:12 or SEQ ID NO:26.

More preferred amino acid fragments that are at least about 80%-90% identical are particularly suitable and those sequences that are at least about 90%-95% identical are most preferred. Similarly, preferred Δ9 elongase encoding nucleic acid sequences corresponding to the instant ORFs are those encoding active proteins and which are at least about 80%-90% identical; those sequences that are at least about 90%-95% identical are most preferred.

In alternate embodiments, the instant EaD9Elo1 and/or EaD9Elo2 sequences can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., elongase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

In one embodiment of the invention herein, EaD9Elo1 (SEQ ID NO:11) was codon-optimized for expression in Yarrowia lipolytica. This was possible based on previous determination of the Y. lipolytica codon usage profile, identification of those codons that were preferred, and determination of the consensus sequence around the 'ATG' initiation codon (see U.S. Pat. No. 7,238,482 and U.S. Pat. No. 7,125,672). The resultant synthetic gene is referred to as EaD9ES (SEQ ID NO:26). The protein sequence encoded by the codon-optimized Δ9 elongase gene (i.e., SEQ ID NO:27) is identical to that of the wildtype protein sequence (i.e., SEQ ID NO:13). Similar techniques could be utilized to produce a synthetic Δ9 elongase derived from EaD9Elo2 (SEQ ID NO:12) for expression in Y. lipolytica.

One skilled in the art would be able to use the teachings herein to create various other codon-optimized Δ9 elongase proteins suitable for optimal expression in alternate hosts (i.e., other than Yarrowia lipolytica), based on the wildtype EaD9Elo1 and/or EaD9Elo2 sequences. Accordingly, the instant invention relates to any codon-optimized Δ9 elongase protein that is derived from the wildtype nucleotide sequences of EaD9Elo1 (SEQ ID NO:11) or EaD9Elo2 (SEQ ID NO:12). This includes, but is not limited to, the nucleotide sequence set forth in SEQ ID NO:26, which encodes a synthetic Δ9 elongase protein (i.e., EaD9eS) that was codon-optimized for expression in Yarrowia lipolytica. In alternate embodiments, it may be desirable to modify a portion of the codons encoding EaD9Elo1 and/or EaD9Elo2 to enhance expression of the gene in a host organism including, but not limited to, a plant or plant part, algae, bacteria, alternate yeast, euglenoid, stramenopiles or fungi.

Identification and Isolation of Homologs

Any of the instant elongase sequences (i.e., EaD9Elo1, EaD9Elo2, or EaD9eS) or portions thereof may be used to search for Δ9 elongase homologs in the same or other bacterial, algal, fungal, euglenoid or plant species using sequence analysis software. In general, such computer software matches similar sequences by assigning degrees of homology to various substitutions, deletions, and other modifications.

Alternatively, any of the instant elongase sequences or portions thereof may also be employed as hybridization reagents for the identification of Δ9 elongase homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the Δ9 elongase nucleic acid fragments described herein (or any homologs identified thereof) may be used to isolate genes encoding homologous proteins from the same or other bacterial, algal, fungal, euglenoid or plant species. Isolation of homologous genes using sequence-dependent protocols is well known in the art. Examples of sequence-dependent protocols include, but are not limited to: (1) methods of nucleic acid hybridization; (2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor et al., Proc. Acad. Sci. U.S.A., 82:1074 (1985); or strand displacement amplification (SDA), Walker et al., Proc. Natl. Acad. Sci. U.S.A., 89:392 (1992)]; and, (3) methods of library construction and screening by complementation.

For example, genes encoding similar proteins or polypeptides to the Δ9 elongases described herein could be isolated directly by using all or a portion of the instant nucleic acid fragments as DNA hybridization probes to screen libraries from e.g., any desired yeast or fungus using methodology well known to those skilled in the art (wherein those organisms producing EDA and/or ETrA would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, V A; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *Proc. Acad. Sci. U.S.A.*, 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *Proc. Acad. Sci. U.S.A.*, 86:5673 (1989); Loh et al., *Science*, 243:217 (1989)).

In other embodiments, any of the Δ9 elongase nucleic acid fragments described herein (or any homologs identified thereof) may be used for creation of new and/or improved fatty acid elongases. As is well known in the art, in vitro mutagenesis and selection, chemical mutagenesis, "gene shuffling" methods or other means can be employed to obtain mutations of naturally occurring elongase genes (wherein such mutations may include deletions, insertions and point mutations, or combinations thereof). This would permit production of a polypeptide having elongase activity, respectively, in vivo with more desirable physical and kinetic parameters for function in the host cell such as a longer half-life or a higher rate of production of a desired PUFA. Or, if desired, the regions of a polypeptide of interest (i.e., a Δ9 elongase) important for enzymatic activity can be determined through routine mutagenesis, expression of the resulting mutant polypeptides and determination of their activities. An overview of these techniques is described in U.S. Pat. No. 7,238,482. All such mutant proteins and nucleotide sequences encoding them that are derived from EaD9Elo1, EaD9Elo2 and EaD9eS are within the scope of the present invention.

Alternatively, improved fatty acids may be synthesized by domain swapping, wherein a functional domain from any of the Δ9 elongase nucleic acid fragments described herein are exchanged with a functional domain in an alternate elongase gene to thereby result in a novel protein. As used herein, "domain" or "functional domain" refer to nucleic acid sequence(s) that are capable of eliciting a biological response in microbes.

Methods for Production of Various Omega-3 and/or Omega-6 Fatty Acids

It is expected that introduction of chimeric genes encoding the Δ9 elongases described herein (i.e., EaD9Elo1, EaD9Elo2, EaD9eS or other mutant enzymes, codon-optimized enzymes or homologs thereof), under the control of the appropriate promoters will result in increased production of EDA and/or ETrA in the transformed host organism, respectively. As such, the present invention encompasses a method for the direct production of PUFAs comprising exposing a fatty acid substrate (i.e., LA and/or ALA) to the elongase enzymes described herein (e.g., EaD9Elo1, EaD9Elo2 or EaD9eS), such that the substrate is converted to the desired fatty acid product (i.e., EDA and/or ETrA, respectively).

More specifically, it is an object of the present invention to provide a method for the production of EDA in a microbial host cell (e.g., yeast, algae, bacteria, euglenoids, stramenopiles and fungi), wherein the microbial host cell comprises:
 (a) a recombinant nucleotide molecule encoding a Δ9 elongase polypeptide having at least 80% amino acid identity, based on the Clustal V method of alignment, when compared to a polypeptide having an amino acid sequence as set forth in SEQ ID NO:13 or SEQ ID NO:14; and,
 (b) a source of LA;
wherein the microbial host cell is grown under conditions such that the nucleic acid fragment encoding the Δ9 elongase is expressed and the LA is converted to EDA, and wherein the EDA is optionally recovered.

In alternate embodiments of the present invention, the Δ9 elongase may be used for the conversion of ALA to ETrA. Accordingly the invention provides a method for the production of ETrA, wherein the microbial host cell comprises:
 (a) a recombinant nucleotide molecule encoding a Δ9 elongase polypeptide having at least 80% amino acid identity, based on the Clustal V method of alignment, when compared to a polypeptide having an amino acid sequence as set forth in SEQ ID NO:13 or SEQ ID NO:14; and,
 (b) a source of ALA;
wherein the microbial host cell is grown under conditions such that the nucleic acid fragment encoding the Δ9 elongase is expressed and the ALA is converted to ETrA, and wherein the ETrA is optionally recovered.

Alternatively, each Δ9 elongase gene and its corresponding enzyme product described herein can be used indirectly for the production of various ω-6 and ω-3 PUFAs (see FIG. 1 and U.S. Pat. No. 7,238,482). Indirect production of ω-3/ω-6 PUFAs occurs wherein the fatty acid substrate is converted indirectly into the desired fatty acid product, via means of an intermediate step(s) or pathway intermediate(s). Thus, it is contemplated that the Δ9 elongases described herein (i.e., EaD9Elo1, EaD9Elo2, EaD9eS or other mutant enzymes, codon-optimized enzymes or homologs thereof) may be expressed in conjunction with additional genes encoding enzymes of the PUFA biosynthetic pathway (e.g., Δ6 desaturases, $C_{18/20}$ elongases, Δ17 desaturases, Δ8 desaturases, Δ15 desaturases, Δ9 desaturases, Δ12 desaturases, $C_{14/16}$ elongases, $C_{16/18}$ elongases, Δ9 elongases, Δ5 desaturases, Δ4 desaturases, $C_{20/22}$ elongases) to result in higher levels of production of longer-chain ω-3/ω-6 fatty acids (e.g., ARA, EPA, DTA, DPAn-6, DPA and/or DHA).

In preferred embodiments, the Δ9 elongases of the present invention will minimally be expressed in conjunction with a Δ8 desaturase (e.g., from *Euglena gracilis* [Wallis et al., *Arch. Biochem. and Biophys.*, 365(2):307-316 (May 1999); PCT Publication No. WO 2000/34439; U.S. Pat. No. 6,825,017; PCT Publication No. WO 2004/057001; PCT Publication No. WO 2006/012325; U.S. Pat. No. 7,256,033; U.S. patent application Ser. No. 11/635,258]; from *Acanthamoeba castellanii* [Sayanova et al., *FEBS Lett.*, 580:1946-1952 (2006)]; from *Pavlova salina* [PCT Publication No. WO 2005/103253]; from *Pavlova lutheri* [PCT Publication No. WO 2007/127381]; from *Tetruetreptia pomquetensis* CCMP1491 [U.S. patent application Ser. No. 11/876,115]; from *Eutreptiella* sp. CCMP389 [U.S. patent application Ser. No. 11/876,115]; from *Eutreptiella cf_gymnastica* CCMP1594 [U.S. patent application Ser. No. 11/876,115; and, from *Euglena anabaena* [described in co-pending U.S. patent application Ser. Nos. 12/099,799 and No. 12/099,811]). However, the particular genes included within a particular expression cassette will depend on the host cell (and its PUFA profile and/or desaturase/elongase profile), the availability of substrate and the desired end product(s).

In alternative embodiments, it may be useful to disrupt a host organism's native Δ9 elongase, based on the complete sequences described herein, the complement of those complete sequences, substantial portions of those sequences, codon-optimized elongases derived therefrom and those sequences that are substantially homologous thereto.

Microbial Expression Systems, Cassettes and Vectors

The Δ9 elongase genes and gene products described herein (i.e., EaD9Elo1, EaD9Elo2, EaD9eS or other mutant enzymes, codon-optimized enzymes or homologs thereof) may be expressed in heterologous microbial host cells, particularly in the cells of oleaginous yeasts (e.g., *Yarrowia lipolytica*).

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors (e.g., constructs, plasmids) and DNA expression cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector contains at least one expression cassette, a selectable marker and sequences allowing autonomous replication or chromosomal integration. Suitable expression cassettes comprise a region 5' of the gene that controls transcription (e.g., a promoter), the gene coding sequence, and a region 3' of the DNA fragment that controls transcriptional termination (i.e., a terminator). It is most preferred when both control regions are derived from genes from the transformed microbial host cell, although it is to be understood that such control regions need not be derived from the genes native to the specific species chosen as a production host.

Transcriptional control regions (also initiation control regions or promoters) which are useful to drive expression of the instant Δ9 elongase ORFs in the desired microbial host cell are numerous and familiar to those skilled in the art. Virtually any promoter (i.e., native, synthetic, or chimeric) capable of directing expression of these genes in the selected host cell is suitable for the present invention, although transcriptional and translational regions from the host species are particularly useful. Expression in a microbial host cell can be accomplished in an induced or constitutive fashion. Induced expression can be accomplished by inducing the activity of a regulatable promoter operably linked to the gene of interest, while constitutive expression can be achieved by the use of a constitutive promoter operably linked to the gene of interest. As an example, when the host cell is yeast, transcriptional and translational regions functional in yeast cells are provided, particularly from the host species (e.g., see Patent Publication No. US-2006-0115881-A1 for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Termination control regions may also be derived from various genes native to the preferred hosts. In alternate embodiments, the 3'-region can also be synthetic, as one of skill in the art can utilize available information to design and synthesize a 3'-region sequence that functions as a transcription terminator. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: the nature of the relevant transcriptional promoter and terminator sequences; the number of copies of the cloned gene (wherein additional copies may be cloned within a single expression construct and/or additional copies may be introduced into the host cell by increasing the plasmid copy number or by multiple integration of the cloned gene into the genome); whether the gene is plasmid-borne or integrated into the genome of the host cell; the final cellular location of the synthesized foreign protein; the efficiency of translation and correct folding of the protein in the host organism; the intrinsic stability of the mRNA and protein of the cloned gene within the host cell; and, the codon usage within the cloned gene, such that its frequency approaches the frequency of preferred codon usage of the host cell. Each of these types of modifications are encompassed in the present invention, as means to further optimize expression of the Δ9 elongase described herein.

Transformation of Microbial Host Cells

Once a DNA cassette that is suitable for expression in an appropriate microbial host cell has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene(s) of interest may be introduced into a microbial host cell by any standard technique. These techniques include transformation (e.g., lithium acetate transformation [*Methods in Enzymology*, 194:186-187 (1991)]), protoplast transformation, bolistic impact, electroporation, microinjection, or any other method that introduces the gene(s) of interest into the host cell.

For convenience, a host cell that has been manipulated by any method to take up a DNA sequence (e.g., an expression cassette) will be referred to as "transformed", "transformant" or "recombinant" herein. Thus, the term "transformed" and "recombinant" are used interchangeably herein. The transformed host will have at least one copy of the expression construct and may have two or more, depending upon whether the expression cassette is integrated into the genome or is present on an extrachromosomal element having multiple copy numbers.

The transformed host cell can be identified by various selection techniques, as described in U.S. Pat. No. 7,238,482, U.S. Pat. No. 7,259,255 and PCT Publication No. WO 2006/052870.

Following transformation, substrates suitable for the instant Δ9 elongase (and, optionally other PUFA enzymes that are co-expressed within the host cell) may be produced by the host either naturally or transgenically, or they may be provided exogenously.

Preferred Microbial Hosts for Recombinant Expression

Microbial host cells for expression of the instant genes and nucleic acid fragments may include hosts that grow on a variety of feedstocks, including simple or complex carbohydrates, fatty acids, organic acids, oils, glycerol and alcohols, and/or hydrocarbons over a wide range of temperature and pH values. Based on the needs of the Applicants' Assignee, the genes described in the instant invention have been expressed in an oleaginous yeast (and in particular *Yarrowia lipolytica*); however, it is contemplated that because transcription, translation and the protein biosynthetic apparatus are highly conserved, any bacteria, yeast, algae, euglenoid, stramenopiles and/or fungus will be a suitable microbial host for expression of the present nucleic acid fragments.

Preferred microbial hosts, however, are oleaginous organisms, such as oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis,* and *Yarrowia lipolytica* (formerly classified as *Candida lipolytica*). In alternate embodiments, oil biosynthesis may be genetically engineered such that the microbial host cell (e.g., a yeast) can produce more than 25% oil of the cellular dry weight, and thereby be considered oleaginous.

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)).

Historically, various strains of *Y. lipolytica* have been used for the manufacture and production of: isocitrate lyase; lipases; polyhydroxyalkanoates; citric acid; erythritol; 2-oxoglutaric acid; γ-decalactone; γ-dodecalatone; and pyruvic acid. Specific teachings applicable for transformation of oleaginous yeasts (i.e., *Yarrowia lipolytica*) include U.S. Pat. No. 4,880,741 and U.S. Pat. No. 5,071,764 and Chen, D. C. et al. (*Appl. Microbiol. Biotechnol.*, 48(2):232-235 (1997)). Specific teachings applicable for engineering ARA, EPA and DHA production in *Y. lipolytica* are provided in U.S. patent application Ser. No. 11/264,784, U.S. patent application Ser. No. 11/265,761, and U.S. patent application Ser. No. 11/264,737, respectively. The preferred method of expressing genes in this yeast is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene locus (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the Δ12 desaturase gene locus (U.S. Pat. No. 7,214,491), the Lip1 gene locus (GenBank Accession No. Z50020), the Lip2 gene locus (GenBank Accession No. AJ012632), the SCP2 gene locus (GenBank Accession No. AJ431362), and/or the Pex10 gene locus (GenBank Accession No. CAG81606)].

Preferred selection methods for use in *Yarrowia lipolytica* are resistance to kanamycin, hygromycin and the amino glycoside G418, as well as ability to grow on media lacking uracil, leucine, lysine, tryptophan or histidine. In alternate embodiments, 5-fluoroorotic acid (5-fluorouracil-6-carboxylic acid monohydrate; "5-FOA") is used for selection of yeast Ura⁻ mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura⁻ mutant yeast strains (Bartel, P. L. and Fields, S., Yeast 2-Hybrid System, Oxford University: New York, v. 7, pp 109-147, 1997; see also PCT Publication No. WO 2006/052870 for 5-FOA use in *Yarrowia*).

An alternate preferred selection method for use in *Yarrowia* relies on a dominant, non-antibiotic marker for *Yarrowia lipolytica* based on sulfonylurea (chlorimuron ethyl; E. I. duPont de Nemours & Co., Inc., Wilmington, Del.) resistance. More specifically, the marker gene is a native acetohydroxyacid synthase (AHAS or acetolactate synthase; E.C. 4.1.3.18) that has a single amino acid change (W497L) that confers sulfonyl urea herbicide resistance (PCT Publication No. WO 2006/052870). AHAS is the first common enzyme in the pathway for the biosynthesis of branched-chain amino acids (i.e., valine, leucine, isoleucine) and it is the target of the sulfonylurea and imidazolinone herbicides.

Other preferred microbial hosts include oleaginous bacteria, algae, euglenoids, stramenopiles and other fungi; and, within this broad group of microbial hosts, of particular interest are microorganisms that synthesize ω-3/ω-6 fatty acids (or those that can be genetically engineered for this purpose [e.g., other yeast such as *Saccharomyces cerevisiae*]). Thus, for example, transformation of *Mortierella alpina* (which is commercially used for production of ARA) with any of the present Δ9 elongase genes under the control of inducible or regulated promoters could yield a transformant organism capable of synthesizing increased quantities of EDA; this could be converted to increased quantities of DGLA if a Δ8 desaturase gene was co-expressed. The method of transformation of *M. alpina* is described by Mackenzie et al. (*Appl. Environ. Microbiol.*, 66:4655 (2000)). Similarly, methods for transformation of Thraustochytriales microorganisms (e.g., *Thraustochytrium, Schizochytrium*) are disclosed in U.S. Pat. No. 7,001,772.

Irrespective of the host selected for expression of the Δ9 elongases described herein, it may be necessary to screen multiple transformants to obtain a strain displaying the desired expression level and pattern. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618(1-2):133-145 (1993)), Western and/or Elisa analyses of protein expression, phenotypic analysis or GC analysis of the PUFA products.

Based on the teachings described above, in one embodiment this invention is drawn to a method of producing either EDA or ETrA, respectively, comprising:
(a) providing an oleaginous yeast (e.g., *Yarrowia lipolytica*) comprising:
   (i) a first recombinant nucleotide molecule encoding a Δ9 elongase polypeptide, operably linked to at least one regulatory sequence; and,
   (ii) a source of elongase substrate consisting of LA and/or ALA, respectively; and,
(b) growing the yeast of step (a) in the presence of a suitable fermentable carbon source wherein the gene encoding the Δ9 elongase polypeptide is expressed and LA is converted to EDA and/or ALA is converted to ETrA, respectively; and,
(c) optionally recovering the EDA and/or ETrA, respectively, of step (b).

Substrate feeding may be required.

The nucleotide sequence of the gene encoding a Δ9 elongase may be selected from the group consisting of SEQ ID NO:11 and SEQ ID NO:12. In alternate embodiments, the nucleotide sequence of the gene encoding a Δ9 elongase polypeptide is set forth in SEQ ID NO:26 (wherein at least 98 codons have been optimized for expression in *Yarrowia* relative to SEQ ID NO:11).

Since naturally produced PUFAs in oleaginous yeast are limited to 18:2 fatty acids (i.e., LA), and less commonly, 18:3 fatty acids (i.e., ALA), the oleaginous yeast will be genetically engineered to express multiple enzymes necessary for long-chain PUFA biosynthesis (thereby enabling production of e.g., ARA, EPA, DPA and DHA), in addition to the Δ9 elongases described herein.

Specifically, in one embodiment this invention concerns an oleaginous yeast comprising:
(a) a first recombinant DNA construct comprising an isolated polynucleotide encoding a Δ9 elongase polypeptide, operably linked to at least one regulatory sequence; and,
(b) at least one additional recombinant DNA construct comprising an isolated polynucleotide, operably linked to at least one regulatory sequence, encoding a polypeptide selected from the group consisting of: a Δ4 desaturase, a Δ5 desaturase, Δ6 desaturase, a Δ9 desaturase, a Δ12 desaturase, a Δ15 desaturase, a Δ17 desaturase, a Δ8 desaturase, a $C_{14/16}$ elongase, a $C_{16/18}$ elongase, a $C_{18/20}$ elongase and a $C_{20/22}$ elongase.

In particularly preferred embodiments, the at least one additional recombinant DNA construct encodes a polypeptide having Δ8 desaturase activity.

Metabolic Engineering of Omega-3 and/or Omega-6 Fatty Acid Biosynthesis in Microbes Knowledge of the sequences of the present Δ9 elongases will be useful for manipulating ω-3 and/or ω-6 fatty acid biosynthesis in various host cells. Methods for manipulating biochemical pathways are well known to those skilled in the art; and, it is expected that numerous manipulations will be possible to maximize ω-3 and/or ω-6 fatty acid biosynthesis in oleaginous yeasts, and particularly, in *Yarrowia lipolytica*. This manipulation may require metabolic engineering directly within the PUFA biosynthetic pathway or additional manipulation of pathways that contribute carbon to the PUFA biosynthetic pathway. Methods useful for up-regulating desirable biochemical pathways and down-regulating undesirable biochemical pathways are well known to those skilled in the art.

For example, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in U.S. Patent Publication No. 2006-0094092-A1, U.S. Patent Publication No. 2006-0115881-A1 and U.S. Patent Publication No. 2006-0110806-A1, respectively, as are desirable manipulations in the TAG biosynthetic pathway and the TAG degradation pathway (and associated techniques thereof).

Within the context of the present invention, it may be useful to modulate the expression of the fatty acid biosynthetic pathway by any one of the strategies described above. For example, the present invention provides methods whereby genes encoding key enzymes in the Δ9 elongase/Δ8 desaturase biosynthetic pathway are introduced into oleaginous yeasts for the production of ω-3 and/or ω-6 fatty acids. It will be particularly useful to express the present the Δ9 elongase genes in oleaginous yeasts that do not naturally possess ω-3 and/or ω-6 fatty acid biosynthetic pathways and coordinate the expression of these genes, to maximize production of preferred PUFA products using various means for metabolic engineering of the host organism.

Microbial Fermentation Processes for PUFA Production

The transformed microbial host cell is grown under conditions that optimize expression of chimeric desaturase and elongase genes and produce the greatest and most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Microorganisms of interest, such as oleaginous yeast (e.g., *Yarrowia lipolytica*) are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in U.S. Pat. No. 7,238,482. Although it is contemplated that the source of carbon utilized in the present invention may encompass a wide variety of carbon-containing sources, preferred carbon sources are sugars (e.g., glucose), glycerol, and/or fatty acids.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in U.S. Pat. No. 7,238,482, as are various suitable fermentation process designs (i.e., batch, fed-batch and continuous) and considerations during growth.

Purification and Processing of PUFA Oils

PUFAs may be found in the host microorganisms as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology*, 12(5/6):463-491 (1992)). A brief review of downstream processing is also available by A. Singh and O. Ward (*Adv. Appl. Microbiol.*, 45:271-312 (1997)).

In general, means for the purification of PUFAs may include extraction (e.g., U.S. Pat. No. 6,797,303 and U.S. Pat. No. 5,648,564) with organic solvents, sonication, supercritical fluid extraction (e.g., using carbon dioxide), saponification and physical means such as presses, or combinations thereof. One is referred to the teachings of U.S. Pat. No. 7,238,482 for additional details.

PUFA-Containing Oils for use in Foodstuffs, Health Food Products, Pharmaceuticals and Animal Feeds The market place currently supports a large variety of food and feed products, incorporating ω-3 and/or ω-6 fatty acids (particularly e.g., ALA, GLA, ARA, EPA, DPA and DHA). It is contemplated that the microbial biomass comprising long-chain PUFAs, partially purified microbial biomass comprising PUFAs, purified microbial oil comprising PUFAs, and/or purified PUFAs will function in food and feed products to impart the health benefits of current formulations. More specifically, oils of the invention containing ω-3 and/or ω-6 fatty acids will be suitable for use in a variety of food and feed products including, but not limited to: food analogs, meat products, cereal products, baked foods, snack foods and dairy products (see Patent Publication No. US-2006-0094092 for details).

Additionally, the present compositions may be used in formulations to impart health benefit in medical foods including medical nutritionals, dietary supplements, infant formula as well as pharmaceutical products. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

General Methods

Standard recombinant DNA and molecular cloning techniques used in the Examples are well known in the art and are described by: 1.) Sambrook, J., Fritsch, E. F. and Maniatis, T.

*Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" or "hr" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Nomenclature for Expression Cassettes:

The structure of an expression cassette will be represented by a simple notation system of "X::Y::Z", wherein X describes the promoter fragment, Y describes the gene fragment, and Z describes the terminator fragment, which are all operably linked to one another.

Transformation and Cultivation of *Yarrowia lipolytica*:

*Yarrowia lipolytica* strains with ATCC Accession Nos. #20362, #76982 and #90812 were purchased from the American Type Culture Collection (Rockville, Md.). *Yarrowia lipolytica* strains were typically grown at 28-30° C. in several media, according to the recipes shown below. Agar plates were prepared as required by addition of 20 g/L agar to each liquid media, according to standard methodology.

YPD Agar Medium (Per Liter):

10 g of yeast extract [Difco], 20 g of Bacto peptone [Difco]; and 20 g of glucose.

Basic Minimal Media (MM) (Per Liter):

20 g glucose; 1.7 g yeast nitrogen base without amino acids; 1.0 g proline; and pH 6.1 (not adjusted).

Minimal Media+5-Fluoroorotic Acid (MM+5-FOA) (Per Liter):

20 g glucose, 6.7 g Yeast Nitrogen base, 75 mg uracil, 75 mg uridine and appropriate amount of FOA (Zymo Research Corp., Orange, Calif.), based on FOA activity testing against a range of concentrations from 100 mg/L to 1000 mg/L (since variation occurs within each batch received from the supplier).

Transformation of *Yarrowia lipolytica* was performed according to the method of Chen, D. C. et al. (*Appl. Microbiol. Biotechnol.*, 48(2):232-235 (1997)), unless otherwise noted. Briefly, *Yarrowia* was streaked onto a YPD plate and grown at 30° C. for approximately 18 h. Several large loopfuls of cells were scraped from the plate and resuspended in 1 mL of transformation buffer, comprising: 2.25 mL of 50% PEG, average MW 3350; 0.125 mL of 2 M lithium acetate, pH 6.0; 0.125 mL of 2 M DTT; and (optionally) 50 μg sheared salmon sperm DNA. Then, approximately 500 ng of linear DNA (preferably comprising at least one chimeric gene) (or 100 ng circular plasmid) was incubated in 100 μL of resuspended cells, and maintained at 39° C. for 1 h with vortex mixing at 15 min intervals. The cells were plated onto selection media plates and maintained at 30° C. for 2 to 3 days.

Fatty Acid Analysis of *Yarrowia lipolytica*:

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters were prepared by transesterification of the lipid extract with sodium methoxide (Roughan, G. and Nishida I., *Arch Biochem Biophys.*, 276(1):38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μL of 1%) was added to the sample, and then the sample was vortexed and rocked for 20 min. After adding 3 drops of 1 M NaCl and 400 μL hexane, the sample was vortexed and spun. The upper layer was removed and analyzed by GC as described above.

Example 1

Synthesis of a cDNA Library from *Euglena anabaena* UTEX 373

The present Example describes the synthesis of a cDNA library from *Euglena anabaena* UTEX 373. This work included the preparation of RNA, synthesis of cDNA, and generation of a cDNA library.

Growth of *Euglena anabaena* UTEX 373 and Preparation of RNA

Figure 2:
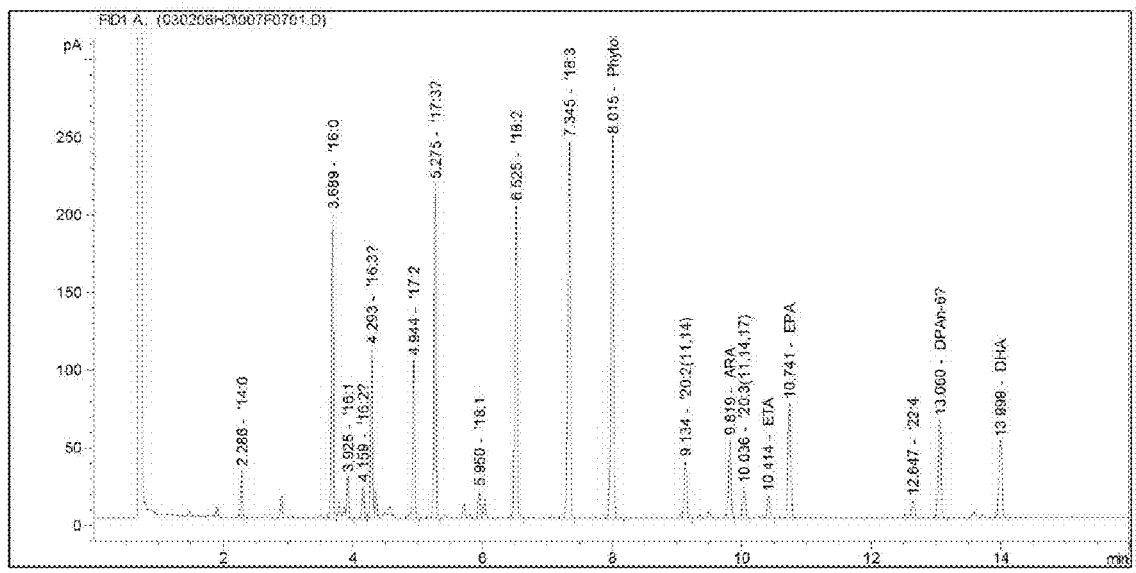
FIG. 2 shows a chromatogram of the lipid profile of an *Euglena anabaena* cell extract as described in the Examples.

*Euglena anabaena* UTEX 373 was obtained from Dr. Richard Triemer's lab at Michigan State University (East Lansing, Mich.). Approximately 2 mL of culture was removed for lipid analysis and centrifuged at 1,800×g for 5 min. The pellet was washed once with water and re-centrifuged. The resulting pellet was dried for 5 min under vacuum, resuspended in 100 μL of trimethylsulfonium hydroxide (TMSH) and incubated at room temperature for 15 min with shaking. After incubation, 0.5 mL of hexane was added and the vials were further incubated for 15 min at room temperature with shaking. Fatty acid methyl esters (5 μL injected from hexane layer) were separated and quantified using a Hewlett-Packard 6890 Gas Chromatograph fitted with an Omegawax 320 fused silica capillary column (Supelco Inc., Catalog No. 24152). The oven temperature was programmed to hold at 170° C. for 1.0 min, increase to 240° C. at 5° C./min and then hold for an additional 1.0 min. Carrier gas was supplied by a Whatman hydrogen generator. Retention times were compared to those for methyl esters of standards commercially available (Nu-Chek Prep, Inc. Catalog No. U-99-A) and the resulting chromatogram is shown in FIG. 2. The presence of EDA, ETrA, EPA and DHA in the fatty acid profile, with the absence of GLA and STA, suggested that *Euglena anabaena* uses the Δ9 elongase/Δ8 desaturase pathway for long-chain (LC) PUFA biosynthesis and would be a good source for LC-PUFA biosynthetic genes such as, but not limited to, Δ9 elongases.

The remaining 5 mL of an actively growing culture was transferred into 25 mL of AF-6 Medium (Watanabe & Hiroki, NIES-Collection List of Strains, 5th ed., National Institute for Environmental Studies, Tsukuba, 127 pp (2004)) in a 125 mL glass flask. *Euglena anabaena* cultures were grown at 22° C. with a 16 h light, 8 h dark cycle for 2 weeks with very gentle agitation.

After 2 weeks, the culture (25 mL) was transferred to 100 mL of AF-6 medium in a 500 mL glass bottle and the culture was grown for 1 month as described above. After this time, two 50 mL aliquots were transferred into two separate 500 mL glass bottles containing 250 mL of AF-6 medium and the cultures were grown for two months as described above (giving a total of ~600 mL of culture). Next, the cultures were pelleted by centrifugation at 1,800×g for 10 min, washed once with water and re-centrifuged. Total RNA was extracted from one of the resulting pellets using the RNA STAT-60™ reagent (TEL-TEST, Inc., Friendswood, Tex.) and following the manufacturer's protocol provided (use 5 mL of reagent, dissolved RNA in 0.5 mL of water). In this way, 340 μg of total RNA (680 μg/mL) was obtained from the pellet. The remaining pellet was frozen in liquid nitrogen and stored at −80° C. The mRNA was isolated from all 340 μg of total RNA using the mRNA Purification Kit (Amersham Biosciences, Piscataway, N.J.) following the manufacturer's protocol provided. In this way, 9.0 μg of mRNA was obtained.

Preparation of *Euglena anabaena* cDNA and Generation of cDNA Library eug1c

A cDNA library was generated using the Cloneminer™ cDNA Library Construction Kit (Catalog No. 18249-029, Invitrogen Corporation, Carlsbad, Calif.) and following the manufacturer's protocol provided (Version B, 25-0608). Using the non-radiolabeling method, cDNA was synthesized from 5.12 μg of mRNA (described above) using the Biotin-attB2-Oligo(dT) primer. After synthesis of the first and second strand, the attB1 adapter was added, ligated and the cDNA was size fractionated using column chromatography. DNA from fractions were concentrated, recombined into pDONR™222 and transformed into *E. coli* ElectroMAX™ DH10B™ T1 Phage-Resistant cells (Invitrogen Corporation). The *Euglena anabaena* library was named eug1c.

The cDNA library eug1c was plated onto LB+Kanamycin plates (approx. 100,000 colonies), the colonies were scraped off and DNA was isolated using the QIAprep® Spin Miniprep Kit (Qiagen Inc., Valencia, Calif.) following the manufacturer's protocol. In this way, a plasmid DNA sub-library from eug1c was obtained.

Example 2

Isolation of Full-Length Δ9 Elongases from *Euglena anabaena* UTEX 373

The present Example describes the identification of cDNAs (SEQ ID NOs:1 and 2) encoding Δ9 elongases from *Euglena anabaena* UTEX 373. This work included the generation of a probe derived from the *Euglena gracilis* Δ9 elongase (EgD9e; SEQ ID NO:3) and the hybridization of the probe to the cDNA library eug1c in order to identify Δ9 elongase homologs from *Euglena anabaena* UTEX 373.

*Euglena gracilis* Δ9 Elongase (EgD9e)

A clone from the *Euglena* cDNA library (eeg1c), called eeg1c.pk001.n5f, containing the *Euglena gracilis* Δ9 elongase (EgD9e; SEQ ID NO:3; which is described in U.S. application Ser. No. 11/601,563 was used as template to amplify EgD9e with oligonucleotide primers oEugEL1-1 (SEQ ID NO:5) and oEugEL1-2 (SEQ ID NO:6) using the VentR® DNA Polymerase (Catalog No. M0254S, New England Biolabs Inc., Beverly, Mass.) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR906 (SEQ ID NO:15).

Colony Lifts

Approximately 17,000 clones of *Euglena anabaena* cDNA library eug1c were plated onto three large square (24 cm×24 cm) petri plates (Corning, Corning, N.Y.) each containing LB+50 μg/mL kanamycin agar media. Cells were grown overnight at 37° C. and plates were then cooled to room temperature.

Biodyne B 0.45 μm membrane (Catalog No. 60207, Pall Corporation, Pensacola, Fla.) was trimmed to approximately 22 cm×22 cm and the membrane was carefully layed on top of the agar to avoid air bubbles. After incubation for 2 min at room temperature, the membrane was marked for orientation, lifted off with tweezers and placed colony-side up on filter paper soaked with 0.5 M sodium hydroxide and 1.5 M sodium chloride. After denaturation for 4 min, the sodium hydroxide was neutralized by placing the membrane on filter paper soaked with 0.5 M Tris-HCL (pH 7.5) and 1.5 M sodium chloride for 4 min. This step was repeated and the membrane was rinsed briefly in 2×SSC buffer (20×SSC is 3 M sodium chloride, 0.3 M sodium citrate; pH 7.0) and air dried on filter paper.

Hybridization

Membranes were pre-hybridized at 65° C. in 200 mL hybridization solution for 2 hr. Hybridization solution contained 6×SSPE (20×SSPE is 3 M sodium chloride, 0.2 M sodium phosphate, 20 mM EDTA; pH 7.4), 5×Denhardt's reagent (100×Denhardt's reagent is 2%(w/v) Ficoll, 2% (w/v) polyvinylpyrrolidone, 2% (w/v) acetylated bovine serum albumin), 0.5% sodium dodecyl sulfate (SDS), 100 μg/mL sheared salmon sperm DNA and 5% dextran sulfate.

A DNA probe was made using an agarose gel purified NcoI/NotI DNA fragment, containing the *Euglena gracilis* Δ9 elongase gene, from pKR906 (SEQ ID NO:15) labeled with $P^{32}$ dCTP using the RadPrime DNA Labeling System (Catalog No. 18428-011, Invitrogen, Carlsbad, Calif.) following the manufacturer's instructions. Unincorporated $P^{32}$ dCTP was separated using a NICK column (Catalog No. 17-0855-02, Amersham Biosciences, Piscataway, N.J.) following the manufacturer's instructions. The probe was denatured for 5 min at 100° C., placed on ice for 3 min and half was added to the hybridization solution.

The membrane was hybridized with the probe overnight at 65° C. with gentle shaking and then washed the following day twice with 2×SSC containing 0.5% SDS (5 min each) and twice with 0.2×SSC containing 0.1% SDS (15 min each). After washing, hyperfilm (Catalog No. RPN30K, Amersham Biosciences, Piscataway, N.J.) was exposed to the membrane overnight at −80° C.

Based on alignment of plates with the exposed hyperfilm, positive colonies were picked using the blunt end of a Pasteur pipette into 1 mL of water and vortexed. Several dilutions were made and plated onto small round Petri dishes (82 mm) containing LB media plus 50 μg/mL kanamycin to obtain around 100 well isolated colonies on a single plate. Lifts were done as described above except NytranN membrane circles (Catalog No. 10416116, Schleicher & Schuell, Keene, N.H.) were used and hybridization was carried out in 100 mL using the remaining radiolabeled probe. In this way, positive clones were confirmed.

Individual positive clones were grown at 37° C. in LB+50 μg/mL kanamycin liquid media and plasmid was purified using the QIAprep® Spin Miniprep Kit (Qiagen Inc.) following the manufacturer's protocol.

DNA inserts were end-sequenced in 384-well plates, using vector-primed M13F universal primer (SEQ ID NO:7), M13rev-28 primer (SEQ ID NO:8) and the poly(A) tail-primed WobbleT oligonucleotides, with the ABI BigDye version 3 Prism sequencing kit. For the sequencing reaction, 100-200 ng of template and 6.4 pmol of primer were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3700 automated sequencers. The WobbleT primer is an equimolar mix of 21 mer poly(T)A, poly(T)C, and poly(T)G, used to sequence the 3' end of cDNA clones.

Sequences were aligned and compared using Sequencher™ (Version 4.2, Gene Codes Corporation, Ann Arbor, Mich.) and in this way, the clones could be categorized into one of two distinct groups based on insert sequence (designated as EaD9Elo1 and EaD9Elo2). Representative clones containing the cDNA for each class of sequence were chosen for further study and sequences for each representative plasmid (i.e., pLF121-1 and pLF121-2) are shown in SEQ ID NO:9 and SEQ ID NO:10, respectively. The sequence shown by a string of NNNN's represents a region of the polyA tail which was not sequenced. The coding sequences for EaD9Elo1 and EaD9Elo2 are shown in SEQ ID NO:11 and SEQ ID NO:12, respectively. The corresponding amino acid sequences for EaD9Elo1 and EaD9Elo2 are shown in SEQ ID NO:13 and SEQ ID NO:14, respectively.

Example 3

Primary Sequence Analysis of the Δ9 Elongase Sequences of *Euglena anabaena* UTEX 373 (EaD9Elo1 and EaD9Elo2) and Comparison to Other Published Δ9 Elongase Sequences The amino acid sequences for EaD9Elo1 (SEQ ID NO:13) and EaD9Elo2 (SEQ ID NO:14) were compared using the Clustal V method (Higgins, D. G. and Sharp, P. M., *Comput. Appl. Biosci.*, 5:151-153 (1989); Higgins et al., *Comput. Appl. Biosci.*, 8:189-191 (1992)) using the MegAlign™ v6.1 program of the LASERGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10).

Compared to EaD9Elo1 (SEQ ID NO:13), EaD9Elo2 (SEQ ID NO:14) has 1 amino acid substitution (i.e., R254Q; based on numbering for EaD9Elo1). The nucleotide sequences of EaD9Elo1 (SEQ ID NO:11) and EaD9Elo2 (SEQ ID NO:12) differ by six base pairs over the full 774 bp lengths.

The amino acid sequences for EaD9Elo1 (SEQ ID NO:13) and EaD9Elo2 (SEQ ID NO:14) were evaluated by BLASTP (Basic Local Alignment Search Tool; Altschul et al., *J. Mol. Biol.*, 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases) using default parameters with the filter turned off. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Both sequences yielded a pLog value of 38.70 (P value of 2e-39) versus the *Isochrysis galbana* long chain polyunsaturated fatty acid elongation enzyme (IgD9e; SEQ ID NO:16) (NCBI Accession No. AAL37626(GI 17226123), locus AAL37626, CDS AF390174; Qi et al., *FEBS Lett.*, 510:159-165 (2002)) when compared to the "nr" database. BLAST scores and probabilities indicate that the instant nucleic acid fragments encode entire *Euglena anabaena* Δ9 fatty acid elongases.

The amino acid sequences for EaD9Elo1 (SEQ ID NO:13) and EaD9Elo2 (SEQ ID NO:14) were compared to IgD9e (SEQ ID NO:16) and the *Euglena gracilis* Δ9 elongase amino acid sequence (EgD9e; SEQ ID NO:4; PCT Publication No. WO 2007/061845) using BlastP, Clustal V and the Jotun Hein methods of sequence comparison. The % identity against IgD9e and EgD9e using each method is shown in Table 4 and Table 5, respectively.

Sequence percent identity calculations were performed by the BlastP and Clustal V methods, as described above. Sequence percent identity calculations performed by the Jotun Hein method (Hein, J. J., *Meth. Enz*, 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2).

TABLE 4

| Sequence Comparison Of EaD9Elo1 (SEQ ID NO: 13) And Ead9elo2 (SEQ ID NO: 14) To IgD9e (SEQ ID NO: 16) | | | |
|---|---|---|---|
| Desaturase | % Identity to IgD9e by BLASTP | % Identity to IgD9e by the Jotun Hein Method | % Identity to IgD9e by the Clustal V Method |
| EaD9Elo1 | 37% | 40.4% | 32.9% |
| EaD9Elo2 | 37% | 41.2% | 32.9% |

TABLE 5

Sequence Comparison Of EaD9Elo1 (SEQ ID NO: 13) And
EaD9Elo2 (SEQ ID NO: 14) To EgD9e (SEQ ID NO: 4)

| Desaturase | % Identity to EgD9e by BLASTP | % Identity to EgD9e by the Jotun Hein Method | % Identity to EgD9e by the Clustal V Method |
|---|---|---|---|
| EaD9Elo1 | 77% | 77.2% | 77.1% |
| EaD9Elo2 | 77% | 77.2% | 77.1% |

Example 4

Functional Analysis of the *Euglena anabaena* UTEX 373 Δ9 Elongases in *Yarrowia lipolytica*

The present Example describes functional analysis of EaD9Elo1 (SEQ ID NO:13) and EaD9Elo2 (SEQ ID NO:14) in *Yarrowia lipolytica*. This work included the following steps: (1) Construction of Gateway®-compatible *Yarrowia* expression vector pY159; (2) transfer of EaD9Elo1 and EaD9Elo2 into pY159 to produce pY173 and pY174; and, (3) comparison of lipid profiles within transformant organisms comprising pY173 and pY174.

Construction of Gateway®-Compatible *Yarrowia* Expression Vector pY159

Plasmid pY5-30 (which was previously described in U.S. Pat. No. 7,259,255), is a shuttle plasmid that can replicate both in *E. coli* and *Yarrowia lipolytica*. Plasmid pY5-30 contains the following: a *Yarrowia* autonomous replication sequence (ARS18); a ColE1 plasmid origin of replication; an ampicillin-resistance gene (Amp$^R$), for selection in *E. coli*; a *Yarrowia* LEU2 gene, for selection in *Yarrowia*; and a chimeric TEF::GUS::XPR gene. Plasmid pDMW263 (SEQ ID NO:17) was created from pY5-30, by replacing the TEF promoter with the *Yarrowia lipolytica* FBAINm promoter (U.S. Pat. No. 7,202,356) using techniques well known to one skilled in the art. Briefly, this promoter refers to a modified promoter which is located in the 5' upstream untranslated region in front of the 'ATG' translation initiation codon of the fructose-bisphosphate aldolase enzyme (E.C. 4.1.2.13) encoded by the fba1 gene and that is necessary for expression, plus a portion of 5' coding region that has an intron, wherein FBAINm has a 52 bp deletion between the ATG translation initiation codon and the intron of the FBAIN promoter (thereby including only 22 amino acids of the N-terminus) and a new translation consensus motif after the intron. Table 6 summarizes the components of pDMW263 (SEQ ID NO:17).

TABLE 6

Components Of Plasmid pDMW263 (SEQ ID NO: 17)

| RE Sites and Nucleotides Within SEQ ID NO: 17 | Description of Fragment and Chimeric Gene Components |
|---|---|
| 4992-4296 SalI/SacII (8505-2014) | ARS18 sequence (GenBank Accession No. A17608) FBAINm::GUS::XPR, comprising: FBAINm: *Yarrowia lipolytica* FBAINm promoter (U.S. Pat. No. 7,202,356); GUS: *E. coli* gene encoding β-glucuronidase (Jefferson, R. A. Nature, 14: 342: 837-838 (1989); |

TABLE 6-continued

Components Of Plasmid pDMW263 (SEQ ID NO: 17)

| RE Sites and Nucleotides Within SEQ ID NO: 17 | Description of Fragment and Chimeric Gene Components |
|---|---|
| | XPR: ~100 bp of the 3' region of the *Yarrowia* Xpr gene (GenBank Accession No. M17741) |
| 6303-8505 | *Yarrowia* Leu2 gene (GenBank Accession No. AF260230) |

The NcoI/SalI DNA fragment from pDMW263 (SEQ ID NO:17), containing the *Yarrowia lipolytica* FBAINm promoter, was cloned into the NcoI/SalI DNA fragment of pDMW237 (SEQ ID NO:18), previously described in PCT Publication No. WO 2006/012325 (the contents of which are hereby incorporated by reference), containing a synthetic Δ9 elongase gene derived from *Isochrysis galbana* and codon-optimized for expression in *Yarrowia lipolytica* (IgD9eS), to produce pY115 (SEQ ID NO:19; FIG. 3A). In FIG. 3A, the modified FBAINm promoter is labeled as FBA1+Intron, while it is labeled as YAR FBA1 PRO+Intron in FIGS. 3B, 3C and 3D.

The FBAINm promoter was amplified from plasmid pY115 (SEQ ID NO:19), using PCR with oligonucleotide primers oYFBA1 (SEQ ID NO:20) and oYFBA1-6 (SEQ ID NO:21). Primer oYFBA1 (SEQ ID NO:20) was designed to introduce a BglII site at the 5' end of the promoter and primer oYFBA1-6 (SEQ ID NO:21) was designed to introduce a NotI site at the 3' end of the promoter while removing the NcoI site and thus, the ATG start codon. The resulting PCR fragment was digested with BglII and NotI and cloned into the BglII/NotI fragment of pY115, containing the vector backbone, to form pY158 (SEQ ID NO:22).

Plasmid pY158 (SEQ ID NO:22) was digested with NotI and the resulting DNA ends were filled. After filling to form blunt ends, the DNA fragments were treated with calf intestinal alkaline phosphatase and separated using agarose gel electrophoresis. The 6992 bp fragment containing the *Yarrowia lipolytica* FBAINm promoter was excised from the agarose gel and purified using the QIAquick® Gel Extraction Kit (Qiagen Inc., Valencia, Calif.) following the manufacturer's protocol. The purified 6992 bp fragment was ligated with cassette rfA using the Gateway Vector Conversion System (Catalog No. 11823-029, Invitrogen Corporation) following the manufacturer's protocol to form *Yarrowia lipolytica* Gateway® destination vector pY159 (SEQ ID NO:23; FIG. 3B).

Construction of *Yarrowia* Expression Vectors pY173 and pY174

Using the Gateway® LR Clonase™ II enzyme mix (Catalog No. 11791-020, Invitrogen Corporation) and following the manufacturer's protocol, the cDNA inserts from pLF121-1 (SEQ ID NO:9; Example 2) and pLF121-2 (SEQ ID NO:10; Example 2) were transferred to pY159 (SEQ ID NO:23) to form pY173 (SEQ ID NO:24; FIG. 3C) and pY174 (SEQ ID NO:25; FIG. 3D), respectively.

Functional Analysis of EaD9Elo1 And EaD9Elo2 in
*Yarrowia lipolytica* Strain Y2224

Strain Y2224 was isolated in the following manner: *Yarrowia lipolytica* ATCC #20362 cells from a YPD agar plate (1% yeast extract, 2% bactopeptone, 2% glucose, 2% agar) were streaked onto a MM plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Strain Y2224 was transformed with pY173 (SEQ ID NO:24; FIG. 3C) and pY174 (SEQ ID NO:25; FIG. 3D) as described in the General Methods.

Single colonies of transformant *Yarrowia lipolytica* containing pY173 and pY174 were grown in 3 mL MM lacking uracil at 30° C. for 16 h after which cells were centrifuged at 250 rpm to pellet. Cells were washed once with water, pelleted by centrifugation and air dried. Pellets were transesterified (Roughan, G. and Nishida, I., *Arch. Biochem. Biophys.,* 276(1):38-46 (1990)) with 500 µL of 1% sodium methoxide for 30 min at 50° C. after which 500 µL of 1 M sodium chloride and 100 µL of heptane were added. After thorough mixing and centrifugation, fatty acid methyl esters (FAMEs) were analyzed by GC. FAMEs (5 µL injected from hexane layer) were separated and quantified using a Hewlett-Packard 6890 Gas Chromatograph fitted with an Omegawax 320 fused silica capillary column (Catalog No. 24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.).

The fatty acid profiles for *Yarrowia lipolytica* expressing pY173 and pY174 are shown in Table 7. Fatty acids are identified as 16:0, 16:1, 18:0, 18:1 (oleic acid), LA, 20:0, 20:1(11), EDA, 22:0, 24:0 and 24:1. Percent Δ9 elongation (Δ9% Elong) was calculated by dividing the weight % (wt %) for EDA by the sum of the wt % for EDA and LA and multiplying by 100 to express as a %. Average is indicated by Ave.

Example 5

Synthesis of a Codon-Optimized Δ9 Elongase Gene
for *Yarrowia lipolytica* (EaD9ES)

The codon usage of the Δ9 elongase gene (EaD9Elo1) of *Euglena anabaena* was optimized for expression in *Yarrowia lipolytica*, in a manner similar to that described in PCT Publication No. WO 2004/101753 and U.S. Pat. No. 7,125,672. Specifically, a codon-optimized Δ9 elongase gene (designated "EaD9ES"; SEQ ID NO:26) was designed based on the coding sequence of EaD9Elo1 (SEQ ID NO:11), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene,* 265(1-2):11-23 (2001)). In addition to modification of the translation initiation site, 106 bp of the 774 bp coding region were modified (13.7%) and 98 codons were optimized (38.0%). The GC content (52.1%) was about the same between the wild type gene (i.e., EaD9Elo1) and the synthetic gene (i.e., EaD9ES). A NcoI site and NotI sites were incorporated around the translation initiation codon and after the stop codon of EaD9ES (SEQ ID NO:26), respectively. FIGS. 4A and 4B show a comparison of the nucleotide sequences of EaD9Elo1 (SEQ ID NO:11) and EaD9ES (SEQ ID NO:26). The protein sequence encoded by the codon-optimized gene (i.e., SEQ ID NO:27) is identical to that of the wildtype protein sequence (i.e., SEQ ID NO:13). The designed EaD9ES gene was synthesized by GenScript Corporation (Piscataway, N.J.) and cloned into pUC57 (GenBank Accession No. Y14837) to generate pEaD9ES (SEQ ID NO:28; FIG. 5A).

Example 6

Construction and Functional Analysis of *Yarrowia lipolytica* Expression Vector pZUFmEaD9ES,
Comprising a Synthetic Δ9 Elongase Gene (Derived from *Euglena anabaena*), Codon-Optimized for
Expression in *Yarrowia lipolytica* (EaD9ES)

The present Example describes the functional expression of *Yarrowia lipolytica* vector pZUFmEaD9ES, comprising a

TABLE 7

Fatty Acid Composition (Wt %) For *Yarrowia lipolytica*
Expressing pY173 (EaD9Elo1) And pY174 (EaD9Elo2)

| Event | 16:0 | 16:1 | 18:0 | 18:1 | LA | 20:0 | 20:1 (11) | EDA | 22:0 | 24:0 | 24:1 | Δ9 % Elong | Ave. Δ9 % Elong |
|---|---|---|---|---|---|---|---|---|---|---|---|---|---|
| PY173-1 | 16.7 | 14.5 | 4.1 | 46.5 | 12.5 | 0.2 | 0.2 | 3.6 | 0.2 | 1.4 | 0.1 | 22.2 | 22.7 |
| pY173-2 | 16.6 | 14.2 | 4.1 | 46.8 | 12.4 | 0.2 | 0.2 | 3.7 | 0.2 | 1.5 | 0.1 | 22.7 | |
| pY173-3 | 16.5 | 14.0 | 4.2 | 47.1 | 12.3 | 0.2 | 0.2 | 3.7 | 0.2 | 1.5 | 0.2 | 23.2 | |
| pY174-1 | 16.9 | 14.3 | 4.2 | 46.8 | 12.5 | 0.2 | 0.2 | 3.2 | 0.2 | 1.4 | 0.1 | 20.5 | 21.1 |
| pY174-2 | 17.0 | 14.1 | 4.3 | 47.4 | 11.8 | 0.2 | 0.2 | 3.3 | 0.2 | 1.4 | 0.1 | 21.6 | |
| pY174-3 | 17.0 | 14.2 | 4.3 | 47.2 | 11.9 | 0.2 | 0.2 | 3.2 | 0.2 | 1.4 | 0.2 | 21.2 | | chimeric FBAINm::EaD9ES::Pex20 gene, wherein EaD9ES is a synthetic Δ9 elongase derived from *Euglena anabaena* and codon-optimized for expression in *Yarrowia*. The plasmid pZUFmEaD9ES (FIG. 5B) contained the following components:

TABLE 8

Components Of Plasmid pZUFmEaD9ES (SEQ ID NO: 29)

| RE Sites And Nucleotides Within SEQ ID NO: 29 | Description Of Fragment And Chimeric Gene Components |
|---|---|
| Swa I/BsiW I (6067-318) | FBAINm::EaD9ES::Pex20, comprising:<br>FBAINm: *Yarrowia lipolytica* FBAIN promoter (U.S. Pat. No. 7,202,356)<br>EaD9ES: codon-optimized Δ9 elongase (SEQ ID NO: 26), derived from *Euglena anabaena*<br>Pex20: Pex20 terminator sequence of *Yarrowia* Pex20 gene (GenBank Accession No. AF054613) |
| 1354-474 | ColE1 plasmid origin of replication |
| 2284-1424 | Ampicillin-resistance gene (AmpR) for selection in *E. coli* |
| 3183-4487 | *Yarrowia* autonomous replication sequence (ARS18; GenBank Accession No. A17608) |
| 6031-4530 | *Yarrowia* Ura 3 gene (GenBank Accession No. AJ306421) |

Functional Analysis of *Yarrowia lipolytica* Transformants Comprising pZUFmEaD9ES Plasmid pZUFmEaD9ES was transformed into strain Y2224 (the FOA resistant mutant from an autonomous mutation of the Ura3 gene of wildtype *Yarrowia* strain ATCC #20362), as described in the General Methods. The transformants were selected on MM plates. After 2 days growth at 30° C., transformants were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 2.2% C20:2 (EDA) and 15.3% C18:2 (LA) of total lipids produced in all 5 transformants, wherein the conversion efficiency of C18:2 to C20:2 in these 5 strains was determined to be about 13%. Thus, this experimental data demonstrated that the synthetic *Euglena anabaena* Δ9 elongase codon-optimized for expression in *Yarrowia lipolytica* (i.e., EaD9ES, as set forth in SEQ ID NOs:26 and 27) actively elongates LA to EDA.

What is claimed is:

1. A method for the production of at least one polyunsaturated fatty acid selected from the group consisting of eicosadienoic acid and eicosatrienoic acid comprising:
   a) providing a transformed microbial host cell comprising:
      (i) a recombinant nucleotide molecule encoding a polypeptide having delta-9 elongase activity, wherein the polypeptide has at least 90% amino acid identity, based on the Clustal V method of alignment, when compared to the amino acid sequence as set forth in SEQ ID NO:13 or SEQ ID NO:14; and
      (ii) a source of a substrate polyunsaturated fatty acid selected from the group consisting of linoleic acid and alpha-linolenic acid;
   b) growing the transformed microbial host cell of step (a) under conditions wherein linoleic acid is converted to eicosadienoic acid and alpha-linolenic acid is converted to eicosatrienoic acid; and
   c) optionally recovering the eicosadienoic acid and/or eicosatrienoic acid of step (b).

2. The method of claim 1, wherein the transformed microbial host cell is a *Yarrowia*, said polypeptide has the full-length amino acid sequence set forth in SEQ ID No. 27, and the recombinant nucleotide molecule comprises at least 98 codons which are optimized for expression in *Yarrowia*.

3. The method according to claim 1, wherein:
   a) the recombinant nucleotide molecule has the full-length nucleic acid sequence selected from the group consisting of SEQ ID NO:11, SEQ ID NO:12 and SEQ ID NO:26; and
   b) the host cell is *Yarrowia lipolytica*.

4. The method according to claim 1 wherein the transformed microbial host cell is selected from the group consisting of yeast, algae, bacteria, euglenoids, stramenopiles and fungi.

5. The method according to claim 4 wherein the transformed microbial host cell is a fungus of the genus *Mortierella*.

6. The method according to claim 4 wherein the transformed microbial host cell is a stramenopile selected from the group consisting of: *Thraustochytrium* and *Schizochytrium*.

7. The method according to claim 4 wherein the transformed microbial host cell is an oleaginous yeast.

8. The method according to claim 7 wherein the transformed microbial host cell is an oleaginous yeast selected from the group consisting of: *Yarrowia, Candida, Rhodotorula, Rhodosporidium, Cryptococcus, Trichosporon* and *Lipomyces*.

* * * * *

SEQUENCE LISTING

<160> NUMBER OF SEQ ID NOS: 29

<210> SEQ ID NO 1
<211> LENGTH: 1129
<212> TYPE: DNA
<213> ORGANISM: Euglena anabaena

<400> SEQUENCE: 1

```
tttttttcgg tctaaaatgg aagcagccaa agaattggtt tccatcgtcc aagaggagct      60
ccccaaggtg gactatgccc agctttggca ggatgccagc agctgtgagg tcctttacct     120
ctcggtggca ttcgtggcga tcaagttcat gctgcgccca ctggacctga agcgccaggc     180
caccttgaag aagctgttca cagcatacaa cttcctcatg tcgatctatt cctttggctc     240
cttcctggcc atggcctatg ccctatcagt aactggcatc ctctccggcg actgtgagac     300
ggcgttcaac aacgatgtgt tcaggatcac aactcagctg ttctacctca gcaagttcgt     360
agagtacatc gactccttct accttcccct tatggacaag ccactgtcgt tccttcagtt     420
cttccatcat ttgggggccc ccattgacat gtggctattc tacaaatacc gcaacgaagg     480
agtctggatc tttgtcctgt tgaatgggtt cattcactgg atcatgtacg gttactattg     540
gacgcggctc atcaagctga acttccccat gcccaagaac ctgatcacct ccatgcagat     600
catccagttc aatgtcgggt tctacatcgt ctggaagtac cgcaatgtgc catgctaccg     660
ccaggatggg atgcgcatgt ttgcctggat cttcaactac tggtatgtcg ggacggtctt     720
gctgctgttc ctcaactttt acgtgcagac gtacatccgg aagccgagga agaaccgagg     780
gaagaaggag taggccacat ggcgcctgcg ctggaggaaa cggtacgctc ggatggtgca     840
ctgcacttgc actccgccgt ttctagcctc ccctcgctct aaccactgcg gcatgcctgc     900
ttgaggcgtg acgttgcctc gtatgataca gtttacaccc ttcccacagc ccacggagct     960
ggtgactgtt tccagcgtct gcagatcatt gatctggtgc aatgtgcaca gaccaagccc    1020
```

```
ctctaacgtc ttgcggtgta ccgctcgaca ctcactgcaa gagacagatg gctgagcatg    1080
ttatagcccc ttacattcta cccttcgtcc caacctgacc gtcacattc                1129

<210> SEQ ID NO 2
<211> LENGTH: 1145
<212> TYPE: DNA
<213> ORGANISM: Euglena anabaena

<400> SEQUENCE: 2 atttttttc ggtctaaaat ggaagcagcc aaagaattgg tttccatcgt ccaagaggag      60
ctccccaagg tggactatgc ccagctttgg caggacgcca gcagctgtga ggtcctttac    120
ctctcggtgg cattcgtggc gatcaagttc atgctgcgcc cactggacct gaagcgccag    180
gccaccttga agaagctgtt cacagcatac aacttcctca tgtcgatcta ttcctttggc    240
tccttcctgg ccatggccta tgccctatca gtaactggca tcctctccgg cgactgtgag    300
acagcgttca caacgatgt gttcaggatc acaactcagc tgttctacct cagcaagttc    360
gtagagtaca tcgactcctt ctaccttccc cttatggaca gccactgtc gttccttcag    420 ttcttccatc atttgggggc tcccattgac atgtggctat tctacaaata ccgcaacgaa    480
ggagtctgga tctttgtcct gttgaatggg ttcattcact ggatcatgta cggttactac    540
tggacgcggc tcatcaagct gaacttcccc atgcccaaga acctgatcac ctccatgcag    600
atcatccagt tcaatgtcgg gttctacatc gtctggaagt accgcaatgt gccatgctac    660
cgccaggatg ggatgcgcat gtttgcctgg atcttcaact actggtacgt cgggacggtc    720
ttgctgctgt tcctcaactt ttacgtgcag acgtacatcc ggaagccgag gaagaaccaa    780
gggaagaagg agtaggccac atggcgcctg cgctggagga acggtacgc tcggatggtg    840 cactgcactt gcactccgcc gcttctagcc tcccctcgct ctaacctctg cgacatgcct    900
gcttgaggcg tgacgttgcc tcgtgcgata cagtttacac ccttcccatg cccacggag    960 caggtgactg tctccagcgt ctgcaattct gatcattggt ctggtgcaat gtgcgcagac   1020
caagcccctc taacgtcttg cggtgtaccg ctcgacactc actgcacgag acagatggct   1080
gagcatgtta tagcccctga cattctaccc ttcgtcctta cctgaccgtc acattcatgc   1140
ttacc                                                              1145

<210> SEQ ID NO 3
<211> LENGTH: 774
<212> TYPE: DNA
<213> ORGANISM: Euglena gracilis
<220> FEATURE:
<221> NAME/KEY: CDS
<222> LOCATION: (1)..(774)
<223> OTHER INFORMATION: delta-9 elongase
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES IN SEQ ID NO: (1)..(774)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: US 2007-0117190-A1
<311> PATENT FILING DATE: 2006-11-16
<312> PUBLICATION DATE: 2007-05-24
<313> RELEVANT RESIDUES IN SEQ ID NO: (1)..(774)

<400> SEQUENCE: 3 atg gag gtg gtg aat gaa ata gtc tca att ggg cag gaa gtt tta ccc      48
```

```
Met Glu Val Val Asn Glu Ile Val Ser Ile Gly Gln Glu Val Leu Pro
1               5                  10                  15 aaa gtt gat tat gcc caa ctc tgg agt gat gcc agt cac tgt gag gtg      96
Lys Val Asp Tyr Ala Gln Leu Trp Ser Asp Ala Ser His Cys Glu Val
            20                  25                  30 ctt tac ttg tcc atc gca ttt gtc atc ttg aag ttc act ctt ggc ccc     144
Leu Tyr Leu Ser Ile Ala Phe Val Ile Leu Lys Phe Thr Leu Gly Pro
        35                  40                  45 ctt ggt cca aaa ggt cag tct cgt atg aag ttt gtt ttc acc aat tac     192
Leu Gly Pro Lys Gly Gln Ser Arg Met Lys Phe Val Phe Thr Asn Tyr
    50                  55                  60 aac ctt ctc atg tcc att tat tcg ttg gga tca ttc ctc tca atg gca     240
Asn Leu Leu Met Ser Ile Tyr Ser Leu Gly Ser Phe Leu Ser Met Ala
65                  70                  75                  80 tat gcc atg tac acc atc ggt gtt atg tct gac aac tgc gag aag gct     288
Tyr Ala Met Tyr Thr Ile Gly Val Met Ser Asp Asn Cys Glu Lys Ala
                85                  90                  95 ttt gac aac aac gtc ttc agg atc acc acg cag ttg ttc tat ttg agc     336
Phe Asp Asn Asn Val Phe Arg Ile Thr Thr Gln Leu Phe Tyr Leu Ser
            100                 105                 110 aag ttc ctg gag tat att gac tcc ttc tat ttg cca ctg atg ggc aag     384
Lys Phe Leu Glu Tyr Ile Asp Ser Phe Tyr Leu Pro Leu Met Gly Lys
        115                 120                 125 cct ctg acc tgg ttg caa ttc ttc cat cat ttg ggg gca ccg atg gat     432
Pro Leu Thr Trp Leu Gln Phe Phe His His Leu Gly Ala Pro Met Asp
    130                 135                 140 atg tgg ctg ttc tat aat tac cga aat gaa gct gtt tgg att ttt gtg     480
Met Trp Leu Phe Tyr Asn Tyr Arg Asn Glu Ala Val Trp Ile Phe Val
145                 150                 155                 160 ctg ttg aat ggt ttc atc cac tgg atc atg tac ggt tat tat tgg acc     528
Leu Leu Asn Gly Phe Ile His Trp Ile Met Tyr Gly Tyr Tyr Trp Thr
                165                 170                 175 aga ttg atc aag ctg aag ttc ccc atg cca aaa tcc ctg att aca tca     576
Arg Leu Ile Lys Leu Lys Phe Pro Met Pro Lys Ser Leu Ile Thr Ser
            180                 185                 190 atg cag atc att caa ttc aat gtt ggt ttc tac att gtc tgg aag tac     624
Met Gln Ile Ile Gln Phe Asn Val Gly Phe Tyr Ile Val Trp Lys Tyr
        195                 200                 205 agg aac att ccc tgt tat cgc caa gat ggg atg agg atg ttt ggc tgg     672
Arg Asn Ile Pro Cys Tyr Arg Gln Asp Gly Met Arg Met Phe Gly Trp
    210                 215                 220 ttc ttc aat tac ttt tat gtt ggc aca gtc ttg tgt ttg ttc ttg aat     720
Phe Phe Asn Tyr Phe Tyr Val Gly Thr Val Leu Cys Leu Phe Leu Asn
225                 230                 235                 240 ttc tat gtg caa acg tat atc gtc agg aag cac aag gga gcc aaa aag     768
Phe Tyr Val Gln Thr Tyr Ile Val Arg Lys His Lys Gly Ala Lys Lys
                245                 250                 255 att cag                                                              774
Ile Gln <210> SEQ ID NO 4
<211> LENGTH: 258
<212> TYPE: PRT
<213> ORGANISM: Euglena gracilis

<400> SEQUENCE: 4

Met Glu Val Val Asn Glu Ile Val Ser Ile Gly Gln Glu Val Leu Pro
1               5                  10                  15

Lys Val Asp Tyr Ala Gln Leu Trp Ser Asp Ala Ser His Cys Glu Val
            20                  25                  30
```

```
Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
 50                  55                  60

Asn Leu Leu Met Ser Ile Tyr Ser Leu Gly Ser Phe Leu Ser Met Ala
 65                  70                  75                  80

Tyr Ala Met Tyr Thr Ile Gly Val Met Ser Asp Asn Cys Glu Lys Ala
                 85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln

<210> SEQ ID NO 5
<211> LENGTH: 30
<212> TYPE: DNA
<213> ORGANISM: Artificial Sequence
<220> FEATURE:
<223> OTHER INFORMATION: sense oligonucleotide oEugEL1-1

<400> SEQUENCE: 5
agcggccgca ccatggaggt ggtgaatgaa                                    30

<210> SEQ ID NO 6
<211> LENGTH: 30
<212> TYPE: DNA
<213> ORGANISM: Artificial Sequence
<220> FEATURE:
<223> OTHER INFORMATION: sense oligonucleotide oEugEL1-2

<400> SEQUENCE: 6
tgcggccgct cactgaatct ttttggctcc                                    30

<210> SEQ ID NO 7
<211> LENGTH: 18
<212> TYPE: DNA
<213> ORGANISM: Artificial Sequence
<220> FEATURE:
<223> OTHER INFORMATION: M13F universal primer

<400> SEQUENCE: 7
tgtaaaacga cggccagt                                                 18
```

<210> SEQ ID NO 8
<211> LENGTH: 22
<212> TYPE: DNA
<213> ORGANISM: Artificial Sequence
<220> FEATURE:
<223> OTHER INFORMATION: primer M13-28Rev

<400> SEQUENCE: 8
gtaatacgac tcactatagg gc                                              22

<210> SEQ ID NO 9
<211> LENGTH: 3668
<212> TYPE: DNA
<213> ORGANISM: Artificial Sequence
<220> FEATURE:
<223> OTHER INFORMATION: plasmid pLF121-1
<220> FEATURE:
<221> NAME/KEY: misc_feature
<222> LOCATION: (3616)..(3655)
<223> OTHER INFORMATION: n is a, c, g, or t

<400> SEQUENCE: 9

```
gtacaaagtt ggcattataa gaaagcattg cttatcaatt tgttgcaacg aacaggtcac      60
tatcagtcaa aataaaatca ttatttgcca tccagctgat atccctata gtgagtcgta     120 ttacatggtc atagctgttt cctggcagct ctggcccgtg tctcaaaatc tctgatgtta    180
cattgcacaa gataaaaata tatcatcatg ttagaaaaac tcatcgagca tcaaatgaaa    240
ctgcaattta ttcatatcag gattatcaat accatatttt tgaaaaagcc gtttctgtaa    300
tgaaggagaa aactcaccga ggcagttcca taggatggca agatcctggt atcggtctgc    360
gattccgact cgtccaacat caatacaacc tattaatttc ccctcgtcaa aaataaggtt    420
atcaagtgag aaatcaccat gagtgacgac tgaatccggt gagaatggca aaagcttatg    480
catttctttc cagacttgtt caacaggcca gccattacgc tcgtcatcaa aatcactcgc    540
atcaaccaaa ccgttattca ttcgtgattg cgcctgagcg agacgaaata cgcgatcgct    600
gttaaaagga caattacaaa caggaatcga atgcaaccgg cgcaggaaca ctgccagcgc    660
atcaacaata ttttcacctg aatcaggata ttcttctaat acctggaatg ctgttttccc    720
ggggatcgca gtggtgagta accatgcatc atcaggagta cggataaaat gcttgatggt    780
cggaagaggc ataaattccg tcagccagtt tagtctgacc atctcatctg taacatcatt    840
ggcaacgcta cctttgccat gtttcagaaa caactctggc gcatcgggct tcccatacaa    900
tcgatagatt gtcgcacctg attgcccgac attatcgcga gcccatttat acccatataa    960
atcagcatcc atgttggaat ttaatcgcgg cctcgagcaa gacgtttccc gttgaatatg   1020
gctcatagat cttttctcca tcactgatag ggagtggtaa aataactcca tcaatgatag   1080
agtgtcaaca acatgaccaa aatcccttaa cgtgagttac gcgtattaat tgcgttgcgc   1140
tcactgcccg ctttccagtc gggaaacctg tcgtgccagc tgcattaatg aatcggccaa   1200
cgcgcgggga gaggcggttt gcgtattggg cgctcttccg cttcctcgct cactgactcg   1260
ctgcgctcgg tcgttcggct gcggcgagcg gtatcagctc actcaaaggc ggtaatacgg   1320
ttatccacag aatcagggga taacgcagga agaacatgt gagcaaaagg ccagcaaaag   1380
gccaggaacc gtaaaaaggc cgcgttgctg cgttttttcc ataggctccg ccccctgac   1440 gagcatcaca aaaatcgacg ctcaagtcag aggtggcgaa acccgacagg actataaaga   1500
taccaggcgt ttccccctgg aagctccctc gtgcgctctc ctgttccgac cctgccgctt   1560
accggatacc tgtccgcctt tctcccttcg ggaagcgtgg cgctttctca atgctcacgc   1620
```

```
tgtaggtatc tcagttcggt gtaggtcgtt cgctccaagc tgggctgtgt gcacgaaccc   1680
cccgttcagc ccgaccgctg cgccttatcc ggtaactatc gtcttgagtc caacccggta   1740
agacacgact tatcgccact ggcagcagcc actggtaaca ggattagcag agcgaggtat   1800
gtaggcggtg ctacagagtt cttgaagtgg tggcctaact acggtacac tagaagaaca   1860
gtatttggta tctgcgctct gctgaagcca gttaccttcg gaaaagagt tggtagctct   1920
tgatccggca acaaaccac cgctggtagc ggtggttttt ttgtttgcaa gcagcagatt   1980
acgcgcagaa aaaaggatc tcaagaagat cctttgatct tttctacggg gtctgacgct   2040
cagggaacga cgcgtaccgc tagccaggaa gagtttgtag aaacgcaaaa aggccatccg   2100
tcaggatggc cttctgctta gtttgatgcc tggcagttta tggcgggcgt cctgcccgcc   2160
accctccggg ccgttgcttc acaacgttca aatccgctcc cggcggattt gtcctactca   2220
ggagagcgtt caccgacaaa caacagataa acgaaaggc ccagtcttcc gactgagcct   2280
ttcgttttat ttgatgcctg gcagttccct actctcgcgt taacgctagc atggatgttt   2340
tcccagtcac gacgttgtaa acgacggcc agtcttaagc tcgggcccca ataatgatt   2400
ttattttgac tgatagtgac ctgttcgttg caacaaattg atgagcaatg ctttttttata   2460
atgccaactt tgtacaaaaa agttggtttt tttcggtcta aaatggaagc agccaaagaa   2520
ttggttttcca tcgtccaaga ggagctcccc aaggtggact atgcccagct ttggcaggat   2580
gccagcagct gtgaggtcct ttacctctcg gtggcattcg tggcgatcaa gttcatgctg   2640
cgcccactgg acctgaagcg ccaggccacc ttgaagaagc tgttcacagc atacaacttc   2700
ctcatgtcga tctattcctt tggctccttc ctggccatgg cctatgccct atcagtaact   2760
ggcatcctct ccggcgactg tgagacgcg ttcaacaacg atgtgttcag gatcacaact   2820
cagctgttct acctcagcaa gttcgtagag tacatcgact ccttctacct tccccttatg   2880
gacaagccac tgtcgttcct tcagttcttc catcatttgg gggcccccat tgacatgtgg   2940
ctattctaca aataccgcaa cgaaggagtc tggatctttg tcctgttgaa tgggttcatt   3000
cactggatca tgtacggtta ctattggacg cggctcatca agctgaactt ccccatgccc   3060
aagaacctga tcacctccat gcagatcatc cagttcaatg tcgggttcta catcgtctgg   3120
aagtaccgca atgtgccatg ctaccgccag gatgggatgc gcatgtttgc ctggatcttc   3180
aactactggt atgtcgggac ggtcttgctg ctgttcctca acttttacgt gcagacgtac   3240
atccggaagc cgaggaagaa ccgagggaag aaggagtagg ccacatggcg cctgcgctgg   3300
aggaaacggt acgctcggat ggtgcactgc acttgcactc cgccgtttct agcctcccct   3360
cgctctaacc actgcggcat gcctgcttga ggcgtgacgt tgcctcgtat gatacagttt   3420
acacccttcc cacagcccac ggagctggtg actgttccca gcgtctgcag atcattgatc   3480
tggtgcaatg tgcacagacc aagcccctct aacgtcttgc ggtgtaccgc tcgacactca   3540
ctgcaagaga cagatggctg agcatgttat agccccttac attctaccct tcgtcccaac   3600
ctgaccgtca cattcnnnnn nnnnnnnnnn nnnnnnnnnn nnnnnnnnnn nnnnnaccca   3660
actttctt                                                           3668
```

<210> SEQ ID NO 10  
<211> LENGTH: 3684  
<212> TYPE: DNA  
<213> ORGANISM: Artificial Sequence  
<220> FEATURE:  
<223> OTHER INFORMATION: plasmid pLF121-2  
<220> FEATURE:  
<221> NAME/KEY: misc_feature  
<222> LOCATION: (3632)..(3671)

<223> OTHER INFORMATION: n is a, c, g, or t

<400> SEQUENCE: 10

| | | | | | |
|---|---|---|---|---|---|
| gtacaaagtt | ggcattataa | gaaagcattg | cttatcaatt | tgttgcaacg | aacaggtcac | 60 |
| tatcagtcaa | aataaaatca | ttatttgcca | tccagctgat | atccctata | gtgagtcgta | 120 |
| ttacatggtc | atagctgttt | cctggcagct | ctggcccgtg | tctcaaaatc | tctgatgtta | 180 |
| cattgcacaa | gataaaaata | tatcatcatg | ttagaaaaac | tcatcgagca | tcaaatgaaa | 240 |
| ctgcaattta | ttcatatcag | gattatcaat | accatatttt | tgaaaaagcc | gtttctgtaa | 300 |
| tgaaggagaa | aactcaccga | ggcagttcca | taggatggca | agatcctggt | atcggtctgc | 360 |
| gattccgact | cgtccaacat | caatacaacc | tattaatttc | ccctcgtcaa | aaataaggtt | 420 |
| atcaagtgag | aaatcaccat | gagtgacgac | tgaatccggt | gagaatggca | aaagcttatg | 480 |
| catttctttc | cagacttgtt | caacaggcca | gccattacgc | tcgtcatcaa | aatcactcgc | 540 |
| atcaaccaaa | ccgttattca | ttcgtgattg | cgcctgagcg | agacgaaata | cgcgatcgct | 600 |
| gttaaaagga | caattacaaa | caggaatcga | atgcaaccgg | cgcaggaaca | ctgccagcgc | 660 |
| atcaacaata | ttttcacctg | aatcaggata | ttcttctaat | acctggaatg | ctgttttccc | 720 |
| ggggatcgca | gtggtgagta | accatgcatc | atcaggagta | cggataaaat | gcttgatggt | 780 |
| cggaagaggc | ataaattccg | tcagccagtt | tagtctgacc | atctcatctg | taacatcatt | 840 |
| ggcaacgcta | cctttgccat | gtttcagaaa | caactctggc | gcatcgggct | tcccatacaa | 900 |
| tcgatagatt | gtcgcacctg | attgcccgac | attatcgcga | gcccatttat | acccatataa | 960 |
| atcagcatcc | atgttggaat | ttaatcgcgg | cctcgagcaa | gacgtttccc | gttgaatatg | 1020 |
| gctcatagat | cttttctcca | tcactgatag | ggagtggtaa | aataactcca | tcaatgatag | 1080 |
| agtgtcaaca | acatgaccaa | aatcccttaa | cgtgagttac | gcgtattaat | tgcgttgcgc | 1140 |
| tcactgcccg | ctttccagtc | gggaaacctg | tcgtgccagc | tgcattaatg | aatcggccaa | 1200 |
| cgcgcgggga | gaggcggttt | gcgtattggg | cgctcttccg | cttcctcgct | cactgactcg | 1260 |
| ctgcgctcgg | tcgttcggct | gcggcgagcg | gtatcagctc | actcaaaggc | ggtaatacgg | 1320 |
| ttatccacag | aatcagggga | taacgcagga | aagaacatgt | gagcaaaagg | ccagcaaaag | 1380 |
| gccaggaacc | gtaaaaaggc | cgcgttgctg | gcgtttttcc | ataggctccg | cccccctgac | 1440 |
| gagcatcaca | aaaatcgacg | ctcaagtcag | aggtggcgaa | acccgacagg | actataaaga | 1500 |
| taccaggcgt | ttccccctgg | aagctccctc | gtgcgctctc | ctgttccgac | cctgccgctt | 1560 |
| accggatacc | tgtccgcctt | tctcccttcg | ggaagcgtgg | cgctttctca | atgctcacgc | 1620 |
| tgtaggtatc | tcagttcggt | gtaggtcgtt | cgctccaagc | tgggctgtgt | gcacgaaccc | 1680 |
| cccgttcagc | ccgaccgctg | cgccttatcc | ggtaactatc | gtcttgagtc | caacccggta | 1740 |
| agacacgact | tatcgccact | ggcagcagcc | actggtaaca | ggattagcag | agcgaggtat | 1800 |
| gtaggcggtg | ctacagagtt | cttgaagtgg | tggcctaact | acggttacac | tagaagaaca | 1860 |
| gtatttggta | tctgcgctct | gctgaagcca | gttaccttcg | gaaaaagagt | tggtagctct | 1920 |
| tgatccggca | aacaaaccac | cgctggtagc | ggtggttttt | ttgtttgcaa | gcagcagatt | 1980 |
| acgcgcagaa | aaaaaggatc | tcaagaagat | cctttgatct | tttctacggg | gtctgacgct | 2040 |
| cagggaacga | cgcgtaccgc | tagccaggaa | gagtttgtag | aaacgcaaaa | aggccatccg | 2100 |
| tcaggatggc | cttctgctta | gtttgatgcc | tggcagttta | tggcgggcgt | cctgcccgcc | 2160 |
| accctccggg | ccgttgcttc | acaacgttca | aatccgctcc | cggcggattt | gtcctactca | 2220 |
| ggagagcgtt | caccgacaaa | caacagataa | aacgaaaggc | ccagtcttcc | gactgagcct | 2280 |

```
ttcgttttat tgatgcctg gcagttccct actctcgcgt taacgctagc atggatgttt    2340
tcccagtcac gacgttgtaa aacgacggcc agtcttaagc tcgggcccca ataatgatt    2400 ttattttgac tgatagtgac ctgttcgttg caacaaattg atgagcaatg ctttttata    2460 atgccaactt tgtacaaaaa agttggattt tttttcggtc taaaatggaa gcagccaaag   2520
aattggtttc catcgtccaa gaggagctcc ccaaggtgga ctatgcccag ctttggcagg   2580
acgccagcag ctgtgaggtc ctttacctct cggtggcatt cgtggcgatc aagttcatgc   2640
tgcgcccact ggacctgaag cgccaggcca ccttgaagaa gctgttcaca gcatacaact   2700
tcctcatgtc gatctattcc tttggctcct tcctggccat ggcctatgcc ctatcagtaa   2760
ctggcatcct ctccggcgac tgtgagacag cgttcaacaa cgatgtgttc aggatcacaa   2820
ctcagctgtt ctacctcagc aagttcgtag agtacatcga ctccttctac cttcccctta   2880
tggacaagcc actgtcgttc cttcagttct ccatcatttt gggggctccc attgacatgt   2940
ggctattcta caaataccgc aacgaaggag tctggatctt tgtcctgttg aatgggttca   3000
ttcactggat catgtacggt tactactgga cgcggctcat caagctgaac ttccccatgc   3060
ccaagaacct gatcacctcc atgcagatca tccagttcaa tgtcgggttc tacatcgtct   3120
ggaagtaccg caatgtgcca tgctaccgcc aggatgggat gcgcatgttt gcctggatct   3180
tcaactactg gtacgtcggg acggtcttgc tgctgttcct caacttttac gtgcagacgt   3240
acatccggaa gccgaggaag aaccaaggga agaaggagta ggccacatgg cgcctgcgct   3300
ggaggaaacg gtacgctcgg atggtgcact gcacttgcac tccgccgctt ctagcctccc   3360
ctcgctctaa cctctgcgac atgcctgctt gaggcgtgac gttgcctcgt gcgatacagt   3420
ttacacccTT cccatggccc acggagcagg tgactgtctc cagcgtctgc aattctgatc   3480
attggtctgg tgcaatgtgc gcagaccaag cccctctaac gtcttgcggt gtaccgctcg   3540
acactcactg cacgagacag atggctgagc atgttatagc ccctgacatt ctacccttcg   3600
tccttacctg accgtcacat tcatgcttac cnnnnnnnnn nnnnnnnnnn nnnnnnnnnn   3660
nnnnnnnnnn nacccaactt tctt                                         3684
```

<210> SEQ ID NO 11
<211> LENGTH: 774
<212> TYPE: DNA
<213> ORGANISM: Euglena anabaena

<400> SEQUENCE: 11

```
atggaagcag ccaaagaatt ggtttccatc gtccaagagg agctccccaa ggtggactat     60
gcccagcttt ggcaggatgc cagcagctgt gaggtccttt acctctcggt ggcattcgtg    120
gcgatcaagt tcatgctgcg cccactggac ctgaagcgcc aggccacctt gaagaagctg    180
ttcacagcat acaacttcct catgtcgatc tattcctttg gctccttcct ggccatggcc    240
tatgccctat cagtaactgg catcctctcc ggcgactgtg agacggcgtt caacaacgat    300
gtgttcagga tcacaactca gctgttctac ctcagcaagt tcgtagagta catcgactcc    360
ttctaccttc cccttatgga caagccactg tcgttcctc agttcttcca tcatttgggg    420
gcccccattg acatgtggct attctacaaa taccgcaacg aaggagtctg gatctttgtc    480
ctgttgaatg ggttcattca ctggatcatg tacggttact attggacgcg gctcatcaag    540
ctgaacttcc ccatgcccaa gaacctgatc acctccatgc agatcatcca gttcaatgtc    600
gggttctaca tcgtctggaa gtaccgcaat gtgccatgct accgccagga tgggatgcgc    660
atgtttgcct ggatcttcaa ctactggtat gtcgggacgg tcttgctgct gttcctcaac    720
```

```
ttttacgtgc agacgtacat ccggaagccg aggaagaacc gagggaagaa ggag        774
```

<210> SEQ ID NO 12
<211> LENGTH: 774
<212> TYPE: DNA
<213> ORGANISM: Euglena anabaena

<400> SEQUENCE: 12

```
atggaagcag ccaaagaatt ggtttccatc gtccaagagg agctccccaa ggtggactat    60
gcccagcttt ggcaggacgc cagcagctgt gaggtccttt acctctcggt ggcattcgtg   120
gcgatcaagt tcatgctgcg cccactggac ctgaagcgcc aggccacctt gaagaagctg   180
ttcacagcat acaacttcct catgtcgatc tattcctttg gctccttcct ggccatggcc   240
tatgccctat cagtaactgg catcctctcc ggcgactgtg agacagcgtt caacaacgat   300
gtgttcagga tcacaactca gctgttctac ctcagcaagt tcgtagagta catcgactcc   360
ttctaccttc cccttatgga caagccactg tcgttccttc agttcttcca tcatttgggg   420
gctcccattg acatgtggct attctacaaa taccgcaacg aaggagtctg gatctttgtc   480
ctgttgaatg ggttcattca ctggatcatg tacggttact actggacgcg gctcatcaag   540
ctgaacttcc ccatgcccaa gaacctgatc acctccatgc agatcatcca gttcaatgtc   600
gggttctaca tcgtctggaa gtaccgcaat gtgccatgct accgccagga tgggatgcgc   660
atgtttgcct ggatcttcaa ctactggtac gtcgggacgg tcttgctgct gttcctcaac   720
ttttacgtgc agacgtacat ccggaagccg aggaagaacc aagggaagaa ggag         774
```

<210> SEQ ID NO 13
<211> LENGTH: 258
<212> TYPE: PRT
<213> ORGANISM: Euglena anabaena

<400> SEQUENCE: 13

```
Met Glu Ala Ala Lys Glu Leu Val Ser Ile Val Gln Glu Glu Leu Pro
1               5                   10                  15

Lys Val Asp Tyr Ala Gln Leu Trp Gln Asp Ala Ser Ser Cys Glu Val
            20                  25                  30

Leu Tyr Leu Ser Val Ala Phe Val Ala Ile Lys Phe Met Leu Arg Pro
        35                  40                  45

Leu Asp Leu Lys Arg Gln Ala Thr Leu Lys Lys Leu Phe Thr Ala Tyr
    50                  55                  60

Asn Phe Leu Met Ser Ile Tyr Ser Phe Gly Ser Phe Leu Ala Met Ala
65                  70                  75                  80

Tyr Ala Leu Ser Val Thr Gly Ile Leu Ser Gly Asp Cys Glu Thr Ala
                85                  90                  95

Phe Asn Asn Asp Val Phe Arg Ile Thr Thr Gln Leu Phe Tyr Leu Ser
            100                 105                 110

Lys Phe Val Glu Tyr Ile Asp Ser Phe Tyr Leu Pro Leu Met Asp Lys
        115                 120                 125

Pro Leu Ser Phe Leu Gln Phe Phe His His Leu Gly Ala Pro Ile Asp
    130                 135                 140

Met Trp Leu Phe Tyr Lys Tyr Arg Asn Glu Gly Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Asn Phe Pro Met Pro Lys Asn Leu Ile Thr Ser
            180                 185                 190
```

```
Met Gln Ile Ile Gln Phe Asn Val Gly Phe Tyr Ile Val Trp Lys Tyr
            195                 200                 205

Arg Asn Val Pro Cys Tyr Arg Gln Asp Gly Met Arg Met Phe Ala Trp
210                 215                 220

Ile Phe Asn Tyr Trp Tyr Val Gly Thr Val Leu Leu Leu Phe Leu Asn
225                 230                 235                 240

Phe Tyr Val Gln Thr Tyr Ile Arg Lys Pro Arg Lys Asn Arg Gly Lys
            245                 250                 255

Lys Glu

<210> SEQ ID NO 14
<211> LENGTH: 258
<212> TYPE: PRT
<213> ORGANISM: Euglena anabaena

<400> SEQUENCE: 14

Met Glu Ala Ala Lys Glu Leu Val Ser Ile Val Gln Glu Glu Leu Pro
1               5                   10                  15

Lys Val Asp Tyr Ala Gln Leu Trp Gln Asp Ala Ser Ser Cys Glu Val
            20                  25                  30

Leu Tyr Leu Ser Val Ala Phe Val Ala Ile Lys Phe Met Leu Arg Pro
        35                  40                  45

Leu Asp Leu Lys Arg Gln Ala Thr Leu Lys Lys Leu Phe Thr Ala Tyr
    50                  55                  60

Asn Phe Leu Met Ser Ile Tyr Ser Phe Gly Ser Phe Leu Ala Met Ala
65                  70                  75                  80

Tyr Ala Leu Ser Val Thr Gly Ile Leu Ser Gly Asp Cys Glu Thr Ala
                85                  90                  95

Phe Asn Asn Asp Val Phe Arg Ile Thr Thr Gln Leu Phe Tyr Leu Ser
            100                 105                 110

Lys Phe Val Glu Tyr Ile Asp Ser Phe Tyr Leu Pro Leu Met Asp Lys
        115                 120                 125

Pro Leu Ser Phe Leu Gln Phe Phe His His Leu Gly Ala Pro Ile Asp
    130                 135                 140

Met Trp Leu Phe Tyr Lys Tyr Arg Asn Glu Gly Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Asn Phe Pro Met Pro Lys Asn Leu Ile Thr Ser
            180                 185                 190

Met Gln Ile Ile Gln Phe Asn Val Gly Phe Tyr Ile Val Trp Lys Tyr
        195                 200                 205

Arg Asn Val Pro Cys Tyr Arg Gln Asp Gly Met Arg Met Phe Ala Trp
    210                 215                 220

Ile Phe Asn Tyr Trp Tyr Val Gly Thr Val Leu Leu Leu Phe Leu Asn
225                 230                 235                 240

Phe Tyr Val Gln Thr Tyr Ile Arg Lys Pro Arg Lys Asn Gln Gly Lys
                245                 250                 255

Lys Glu

<210> SEQ ID NO 15
<211> LENGTH: 4311
<212> TYPE: DNA
<213> ORGANISM: Artificial Sequence
<220> FEATURE:
<223> OTHER INFORMATION: plasmid pKR906
```

<400> SEQUENCE: 15

```
agcggccgca ccatggaggt ggtgaatgaa atagtctcaa ttgggcagga agttttaccc      60
aaagttgatt atgcccaact ctggagtgat gccagtcact gtgaggtgct ttacttgtcc     120
atcgcatttg tcatcttgaa gttcactctt ggccccttg gtccaaaagg tcagtctcgt      180
atgaagtttg ttttcaccaa ttacaacctt ctcatgtcca tttattcgtt gggatcattc     240
ctctcaatgg catatgccat gtacaccatc ggtgttatgt ctgacaactg cgagaaggct     300
tttgacaaca acgtcttcag gatcaccacg cagttgttct atttgagcaa gttcctggag     360
tatattgact ccttctattt gccactgatg ggcaagcctc tgacctggtt gcaattcttc     420
catcatttgg gggcaccgat ggatatgtgg ctgttctata attaccgaaa tgaagctgtt     480
tggatttttg tgctgttgaa tggtttcatc cactggatca tgtacggtta ttattggacc     540
agattgatca agctgaagtt ccccatgcca aaatccctga ttacatcaat gcagatcatt     600
caattcaatg ttggtttcta cattgtctgg aagtacagga acattccctg ttatcgccaa     660
gatgggatga ggatgtttgg ctggttcttc aattactttt atgttggcac agtcttgtgt     720
ttgttcttga atttctatgt gcaaacgtat atcgtcagga agcacaaggg agccaaaaag     780
attcagtgag cggccgcacc tgaattccag cacactggcg gccgttacta gtggatccga     840
gctcggtacc aagcttgatg catagcttga gtattctaac gcgtcaccta aatagcttgg     900
cgtaatcatg gtcatagctg tttcctgtgt gaaattgtta tccgctcaca attccacaca     960
acatacgagc cggaagcata aagtgtaaag cctggggtgc ctaatgagtg agctaactca    1020
cattaattgc gttgcgctca ctgcccgctt tccagtcggg aaacctgtcg tgccagctgc    1080
attaatgaat cggccaacgc gcggggagag gcggtttgcg tattgggcgc tcttccgctt    1140
cctcgctcac tgactcgctg cgctcggtcg ttcggctgcg gcgagcggta tcagctcact    1200
caaaggcggt aatacggtta tccacagaat caggggataa cgcaggaaag aacatgtgag    1260
caaaaggcca gcaaaagccc aggaaccgta aaaaggccgc gttgctggcg tttttccata    1320
ggctccgccc ccctgacgag catcacaaaa atcgacgctc aagtcagagg tggcgaaacc    1380
cgacaggact ataaagatac caggcgtttc ccctggaag ctccctcgtg cgctctcctg     1440
ttccgaccct gccgcttacc ggatacctgt ccgcctttct cccttcggga agcgtggcgc    1500
tttctcatag ctcacgctgt aggtatctca gttcggtgta ggtcgttcgc tccaagctgg    1560
gctgtgtgca cgaaccccc gttcagcccg accgctgcgc cttatccggt aactatcgtc      1620
ttgagtccaa cccggtaaga cacgacttat cgccactggc agcagccact ggtaacagga    1680
ttagcagagc gaggtatgta ggcggtgcta cagagttctt gaagtggtgg cctaactacg    1740
gctacactag aaggacagta tttggtatct gcgctctgct gaagccagtt accttcggaa    1800
aaagagttgg tagctcttga tccggcaaac aaaccaccgc tggtagcggt ggtttttttg    1860
tttgcaagca gcagattacg cgcagaaaaa aaggatctca agaagatcct ttgatctttt    1920
ctacggggtc tgacgctcag tggaacgaaa actcacgtta agggattttg gtcatgagat    1980
tatcaaaaag gatcttcacc tagatccttt taaattaaaa atgaagtttt agcacgtgtc    2040
agtcctgctc ctcggccacg aagtgcacgc agttgccggc cgggtcgcgc agggcgaact    2100
cccgccccca cggctgctcg ccgatctcgg tcatggccgg cccggaggcg tcccggaagt    2160
tcgtggacac gacctccgac cactcggcgt acagctcgtc caggccgcgc acccacaccc    2220
aggccagggt gttgtccggc accacctggt cctggaccgc gctgatgaac agggtcacgt    2280
cgtcccggac cacaccggcg aagtcgtcct ccacgaagtc ccgggagaac ccgagccggt    2340
```

-continued

```
cggtccagaa ctcgaccgct ccggcgacgt cgcgcgcggt gagcaccgga acggcactgg      2400
tcaacttggc catggtggcc ctcctcacgt gctattattg aagcatttat cagggttatt      2460
gtctcatgag cggatacata tttgaatgta tttagaaaaa taaacaaata ggggttccgc      2520
gcacatttcc ccgaaaagtg ccacctgtat gcggtgtgaa ataccgcaca gatgcgtaag      2580
gagaaaatac cgcatcagga aattgtaagc gttaataatt cagaagaact cgtcaagaag      2640
gcgatagaag gcgatgcgct gcgaatcggg agcggcgata ccgtaaagca cgaggaagcg      2700
gtcagcccat tcgccgccaa gctcttcagc aatatcacgg gtagccaacg ctatgtcctg      2760
atagcggtcc gccacaccca gccggccaca gtcgatgaat ccagaaaagc ggccattttc      2820
caccatgata ttcggcaagc aggcatcgcc atgggtcacg acgagatcct cgccgtcggg      2880
catgctcgcc ttgagcctgg cgaacagttc ggctggcgcg agcccctgat gctcttcgtc      2940
cagatcatcc tgatcgacaa gaccggcttc catccgagta cgtgctcgct cgatgcgatg      3000
tttcgcttgg tggtcgaatg ggcaggtagc cggatcaagc gtatgcagcc gccgcattgc      3060
atcagccatg atggatactt tctcggcagg agcaaggtga gatgacagga gatcctgccc      3120
cggcacttcg cccaatagca gccagtccct tcccgcttca gtgacaacgt cgagcacagc      3180
tgcgcaagga acgcccgtcg tggccagcca cgatagccgc gctgcctcgt cttgcagttc      3240
attcagggca ccgacaggt cggtcttgac aaaaagaacc gggcgcccct cgctgacag      3300 ccggaacacg gcggcatcag agcagccgat tgtctgttgt gcccagtcat agccgaatag      3360
cctctccacc caagcggccg gagaacctgc gtgcaatcca tcttgttcaa tcatgcgaaa      3420
cgatcctcat cctgtctctt gatcagagct tgatccctg cgccatcaga tccttggcgg      3480
cgagaaagcc atccagttta cttgcaggg cttcccaacc ttaccagagg cgcccagc       3540 tggcaattcc ggttcgcttg ctgtccataa aaccgcccag tctagctatc gccatgtaag      3600
cccactgcaa gctacctgct ttctcttgc gcttgcgttt tcccttgtcc agatagccca      3660
gtagctgaca ttcatccggg gtcagcaccg tttctgcgga ctggctttct acgtgaaaag      3720
gatctaggtg aagatccttt ttgataatct catgcctgac atttatattc cccagaacat      3780
caggttaatg gcgttttga tgtcattttc gcggtggctg agatcagcca cttcttcccc      3840
gataacggag accggcacac tggccatatc ggtggtcatc atgcgccagc tttcatcccc      3900
gatatgcacc accgggtaaa gttcacggga gactttatct gacagcagac gtgcactggc      3960 caggggatc accatccgtc gccccggcgt gtcaataata tcactctgta catccacaaa       4020
cagacgataa cggctctctc tttttataggt gtaaaccta aactgccgta cgtataggct      4080
gcgcaactgt tgggaagggc gatcggtgcg ggcctcttcg ctattacgcc agctggcgaa      4140 aggggggatgt gctgcaaggc gattaagttg gtaacgcca gggttttccc agtcacgacg      4200
ttgtaaaacg acggccagtg aattgtaata cgactcacta tagggcgaat tgggccctct      4260
agatgcatgc tcgagcggcc gccagtgtga tggatatctg cagaattcag g              4311
```

<210> SEQ ID NO 16
<211> LENGTH: 263
<212> TYPE: PRT
<213> ORGANISM: Isochrysis galbana

<400> SEQUENCE: 16

```
Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30
```

```
Leu Leu Arg Asn Ser Gly Leu Val Asp Glu Lys Lys Gly Ala Tyr Arg
         35                  40                  45

Thr Ser Met Ile Trp Tyr Asn Val Leu Leu Ala Leu Phe Ser Ala Leu
 50                  55                  60

Ser Phe Tyr Val Thr Ala Thr Ala Leu Gly Trp Asp Tyr Gly Thr Gly
 65                  70                  75                  80

Ala Trp Leu Arg Arg Gln Thr Gly Asp Thr Pro Gln Pro Leu Phe Gln
                 85                  90                  95

Cys Pro Ser Pro Val Trp Asp Ser Lys Leu Phe Thr Trp Thr Ala Lys
                100                 105                 110

Ala Phe Tyr Tyr Ser Lys Tyr Val Glu Tyr Leu Asp Thr Ala Trp Leu
            115                 120                 125

Val Leu Lys Gly Lys Arg Val Ser Phe Leu Gln Ala Phe His His Phe
        130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260

<210> SEQ ID NO 17
<211> LENGTH: 9472
<212> TYPE: DNA
<213> ORGANISM: Artificial Sequence
<220> FEATURE:
<223> OTHER INFORMATION: plasmid pDMW263

<400> SEQUENCE: 17
catggcatgg atggtacgtc ctgtagaaac cccaacccgt gaaatcaaaa aactcgacgg      60
cctgtgggca ttcagtctgg atcgcgaaaa ctgtggaatt gatcagcgtt ggtgggaaag     120
cgcgttacaa gaaagccggg caattgctgt gccaggcagt tttaacgatc agttcgccga     180
tgcagatatt cgtaattatg cgggcaacgt ctggtatcag cgcgaagtct ttataccgaa     240
aggttgggca ggccagcgta tcgtgctgcg tttcgatgcg gtcactcatt acggcaaagt     300
gtgggtcaat aatcaggaag tgatggagca tcagggcggc tatacgccat tgaagccga     360 tgtcacgccg tatgttattg ccgggaaaag tgtacgtatc accgtttgtg tgaacaacga     420
actgaactgg cagactatcc cgccgggaat ggtgattacc gacgaaaacg caagaaaaa     480 gcagtcttac ttccatgatt tctttaacta tgccgggatc catcgcagcg taatgctcta     540
cacccacgcc aacacctggg tggacgatat caccgtggtg acgcatgtcg cgcaagactg     600
taaccacgcg tctgttgact ggcaggtggt ggccaatggt gatgtcagcg ttgaactgcg     660
tgatgcggat caacaggtgg ttgcaactgg acaaggcact agcgggactt tgcaagtggt     720
gaatccgcac ctctggcaac cgggtgaagg ttatctctat gaactgtgcg tcacagccaa     780
```

```
aagccagaca gagtgtgata tctacccgct tcgcgtcggc atccggtcag tggcagtgaa    840
gggcgaacag ttcctgatta accacaaacc gttctacttt actggctttg gtcgtcatga    900
agatgcggac ttacgtggca aaggattcga taacgtgctg atggtgcacg accacgcatt    960
aatggactgg attggggcca actcctaccg tacctcgcat tacccttacg ctgaagagat   1020
gctcgactgg gcagatgaac atggcatcgt ggtgattgat gaaactgctg ctgtcggctt   1080
taacctctct ttaggcattg gtttcgaagc gggcaacaag ccgaaagaac tgtacagcga   1140
agaggcagtc aacggggaaa ctcagcaagc gcacttacag gcgattaaag agctgatagc   1200
gcgtgacaaa aaccacccaa gcgtggtgat gtggagtatt gccaacgaac cggatacccg   1260
tccgcaagtg cacgggaata tttcgccact ggcggaagca acgcgtaaac tcgacccgac   1320
gcgtccgatc acctgcgtca atgtaatgtt ctgcgacgct cacaccgata ccatcagcga   1380
tctctttgat gtgctgtgcc tgaaccgtta ttacggatgg tatgtccaaa gcggcgattt   1440
ggaaacggca gagaaggtac tggaaaaaga acttctggcc tggcaggaga aactgcatca   1500
gccgattatc atcaccgaat acggcgtgga tacgttagcc gggctgcact caatgtacac   1560
cgacatgtgg agtgaagagt atcagtgtgc atggctggat atgtatcacc gcgtctttga   1620
tcgcgtcagc gccgtcgtcg gtgaacaggt atggaatttc gccgattttg cgacctcgca   1680
aggcatattg cgcgttggcg gtaacaagaa agggatcttc actcgcgacc gcaaaccgaa   1740
gtcggcggct tttctgctgc aaaaacgctg gactggcatg aacttcggtg aaaaaccgca   1800
gcagggaggc aaacaatgat taattaacta gagcggccgc caccgcggcc cgagattccg   1860
gcctcttcgg ccgccaagcg acccgggtgg acgtctagag gtacctagca attaacagat   1920
agtttgccgg tgataattct cttaacctcc cacactcctt tgacataacg atttatgtaa   1980
cgaaactgaa atttgaccag atattgtgtc cgcggtggag ctccagcttt tgttcccttt   2040
agtgagggtt aatttcgagc ttggcgtaat catggtcata gctgtttcct gtgtgaaatt   2100
gttatccgct cacaattcca cacaacatac gagccggaag cataaagtgt aaagcctggg   2160
gtgcctaatg agtgagctaa ctcacattaa ttgcgttgcg ctcactgccc gctttccagt   2220
cgggaaacct gtcgtgccag ctgcattaat gaatcggcca acgcgcgggg agaggcggtt   2280
tgcgtattgg gcgctcttcc gcttcctcgc tcactgactc gctgcgctcg gtcgttcggc   2340
tgcggcgagc ggtatcagct cactcaaagg cggtaatacg gttatccaca gaatcagggg   2400
ataacgcagg aaagaacatg tgagcaaaag gccagcaaaa ggccaggaac cgtaaaaagg   2460
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
gaagctccct cgtgcgctct cctgttccga ccctgccgct taccggatac ctgtccgcct   2640
ttctcccttc gggaagcgtg gcgctttctc atagctcacg ctgtaggtat ctcagttcgg   2700
tgtaggtcgt tcgctccaag ctgggctgtg tgcacgaacc ccccgttcag cccgaccgct   2760
gcgccttatc cggtaactat cgtcttgagt ccaacccggt aagacacgac ttatcgccac   2820
tggcagcagc cactggtaac aggattagca gagcgaggta tgtaggcggt gctacagagt   2880
tcttgaagtg gtggcctaac tacggctaca ctagaaggac agtatttggt atctgcgctc   2940
tgctgaagcc agttaccttc ggaaaaagag ttggtagctc ttgatccggc aaacaaacca   3000
ccgctggtag cggtggtttt tttgtttgca agcagcagat tacgcgcaga aaaaaaggat   3060
ctcaagaaga tccttttgatc ttttctacgg ggtctgacgc tcagtggaac gaaaactcac   3120
gttaagggat tttggtcatg agattatcaa aaaggatctt cacctagatc cttttaaatt   3180
```

```
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaaccagc    3420
cagccggaag ggccgagcgc agaagtggtc ctgcaactt t atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg cgacacgga    4080 aatgttgaat actcatactc ttcctttttc aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
attagggtga tggttcacgt agtgggccat cgccctgata cggttttt cgcccttga    4500 cgttggagtc cacgttcttt aatagtggac tcttgttcca aactggaaca cactcaacc    4560 ctatctcggt ctattctttt gatttataag gattttgcc gatttcggcc tattggttaa    4620
aaaatgagct gatttaacaa aaatttaacg cgaattttaa caaaatatta cgcttacaa    4680 tttccattcg ccattcaggc tgcgcaactg ttgggaaggg cgatcggtgc gggcctcttc    4740
gctattacgc cagctggcga aaggggggatg tgctgcaagg cgattaagtt gggtaacgcc    4800
agggttttcc cagtcacgac gttgtaaaac gacggccagt gaattgtaat acgactcact    4860
atagggcgaa ttgggtaccg gccccccct cgaggtcgat ggtgtcgata agcttgatat    4920
cgaattcatg tcacacaaac cgatcttcgc ctcaaggaaa cctaattcta catccgagag    4980
actgccgaga tccagtctac actgattaat tttcgggcca ataatttaaa aaaatcgtgt    5040
tatataatat tatatgtatt atatatatac atcatgatga tactgacagt catgtcccat    5100
tgctaaatag acagactcca tctgccgcct ccaactgatg ttctcaatat ttaaggggtc    5160
atctcgcatt gtttaataat aaacagactc catctaccgc ctccaaatga tgttctcaaa    5220
atatattgta tgaacttatt tttattactt agtattatta gacaacttac ttgctttatg    5280
aaaaacactt cctatttagg aaacaattta taatggcagt tcgttcattt aacaatttat    5340
gtagaataaa tgttataaat gcgtatggga atcttaaat atggatagca taatgatat    5400 ctgcattgcc taattcgaaa tcaacagcaa cgaaaaaaat ccttgtaca acataaatag    5460 tcatcgagaa atatcaacta tcaaagaaca gctattcaca cgttactatt gagattatta    5520
ttggacgaga atcacacact caactgtctt tctctcttct agaaatacag gtacaagtat    5580
```

```
gtactattct cattgttcat acttctagtc atttcatccc acatattcct tggatttctc    5640
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat ccttttgttt attacatggg    5820
ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacattttt gcttttacaa    6060
gtacaagtac atcgtacaac tatgtactac tgttgatgca tccacaacag tttgttttgt    6120 tttttttgt tttttttttt tctaatgatt cattaccgct atgtatacct acttgtactt     6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa     6600
ctaaggtatt gaaatcccac aatattccca aagtccaccc ctttccaaat tgtcatgcct    6660
acaactcata taccaagcac taacctacca aacaccacta aaaccccaca aaatatatct    6720
taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg cccttttat agagtcttat     7020 acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatggggt tgaccttctg cttgccgaga    7320 tcggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctggggaat    7560 tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
```

```
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga gtcgccgcc gagaagaaca atcttcttgg agtcagtctt ggtcttctta     8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg gaggggacat    8460
acgagatcgt caagggtttg tggccaactg gtaaataaat gatgtcgacg tttaaacagt    8520
gtacgcagat ctactataga ggaacattta aattgccccg gagaagacgg ccaggccgcc    8580
tagatgacaa attcaacaac tcacagctga ctttctgcca ttgccactag ggggggcct    8640 ttttatatgg ccaagccaag ctctccacgt cggttgggct gcacccaaca ataaatgggt    8700
agggttgcac caacaaaggg atgggatggg gggtagaaga tacgaggata acggggctca    8760
atggcacaaa taagaacgaa tactgccatt aagactcgtg atccagcgac tgacaccatt    8820
gcatcatcta agggcctcaa aactacctcg gaactgctgc gctgatctgg acaccacaga    8880
ggttccgagc actttaggtt gcaccaaatg tcccaccagg tgcaggcaga aaacgctgga    8940
acagcgtgta cagtttgtct taacaaaaag tgagggcgct gaggtcgagc agggtggtgt    9000
gacttgttat agcctttaga gctgcgaaag cgcgtatgga tttggctcat caggccagat    9060
tgagggtctg tggacacatg tcatgttagt gtacttcaat cgcccctgg atatagcccc     9120 gacaataggc cgtggcctca ttttttgcc ttccgcacat ttccattgct cgatacccac     9180
accttgcttc tcctgcactt gccaacctta atactggttt acattgacca acatcttaca    9240 agcgggggc ttgtctaggg tatatataaa cagtggctct cccaatcggt tgccagtctc     9300
ttttttcctt tctttcccca cagattcgaa atctaaacta cacatcacag aattccgagc    9360
cgtgagtatc cacgcaaaga tcagtgtcga gacgacgcgt tttgtgtaat gacacaatcc    9420
gaaagtcgct agcaacacac actctctaca caaactaacc cagctctggt ac            9472
```

<210> SEQ ID NO 18
<211> LENGTH: 7879
<212> TYPE: DNA
<213> ORGANISM: Artificial Sequence
<220> FEATURE:
<223> OTHER INFORMATION: plasmid pDMW237

<400> SEQUENCE: 18

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta    180
aacatactgt acatactcat actcgtaccc gggcaacggt tcacttgag tgcagtggct     240 agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
```

```
gaaagaacat gtgagcaaaa ggccagcaaa aggccaggaa ccgtaaaaag gccgcgttgc    660
tggcgttttt ccataggctc cgccccctg acgagcatca caaaaatcga cgctcaagtc     720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttcctttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cggggggctcc   2580 ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg cgatcggtg cgggcctctt cgctattacg   2940
ccagctggcg aaagggggat gtgctgcaag gcgattaagt tgggtaacgc cagggttttc   3000
```

```
ccagtcacga cgttgtaaaa cgacggccag tgaattgtaa tacgactcac tatagggcga    3060
attgggtacc gggcccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat tttttgctta aattcaatcc cccctcgttc agtgtcaact    4080
gtaatggtag gaaattacca tactttttgaa gaagcaaaaa aaatgaaaga aaaaaaaaat    4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg tttttttttg    4320
ttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct ggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
```

```
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgactcag gcgacgacgg aattcctgca gcccatctgc   6060
agaattcagg agagaccggg ttggcggcgt atttgtgtcc caaaaaacag ccccaattgc   6120
cccggagaag acggccaggc cgcctagatg acaaattcaa caactcacag ctgactttct   6180
gccattgcca ctagggggg gcctttttat atggccaagc caagctctcc acgtcggttg   6240
ggctgcaccc aacaataaat gggtagggtt gcaccaacaa agggatggga tgggggtag    6300 aagatacgag gataacgggg ctcaatggca caaataagaa cgaatactgc cattaagact   6360
cgtgatccag cgactgacac cattgcatca tctaagggcc tcaaaactac ctcggaactg   6420
ctgcgctgat ctggacacca cagaggttcc gagcacttta ggttgcacca aatgtcccac   6480
caggtgcagg cagaaaacgc tggaacagcg tgtacagttt gtcttaacaa aaagtgaggg   6540
cgctgaggtc gagcagggtg gtgtgacttg ttatagcctt tagagctgcg aaagcgcgta   6600
tggatttggc tcatcaggcc agattgaggg tctgtggaca catgtcatgt tagtgtactt   6660
caatcgcccc ctggatatag ccccgacaat aggccgtggc ctcatttttt tgccttccgc   6720
acatttccat tgctcggtac ccacaccttg cttctcctgc acttgccaac cttaatactg   6780
gtttacattg accaacatct tacaagcggg gggcttgtct agggtatata taaacagtgg   6840
ctctcccaat cggttgccag tctcttttt cctttctttc cccacagatt cgaaatctaa    6900
actacacatc acacaatgcc tgttactgac gtccttaagc gaaagtccgg tgtcatcgtc   6960
ggcgacgatg tccgagccgt gagtatccac gacaagatca gtgtcgagac gacgcgtttt   7020
gtgtaatgac acaatccgaa agtcgctagc aacacacact ctctacacaa actaacccag   7080
ctctccatgg ctctggccaa cgacgctggc gagcgaatct gggctgccgt caccgatccc   7140
gaaatcctca ttggcacctt ctcctacctg ctcctgaagc ctctcctgcg aaactctggt   7200
ctcgtggacg agaagaaagg agcctaccga acctccatga tctggtacaa cgtcctcctg   7260
gctctcttct ctgccctgtc cttctacgtg actgccaccg ctctcggctg ggactacggt   7320
actggagcct ggctgcgaag acagaccggt gatactcccc agcctctctt tcagtgtccc   7380
tctcctgtct gggactccaa gctgttcacc tggactgcca aggccttcta ctattctaag   7440
tacgtggagt acctcgacac cgcttggctg gtcctcaagg gcaagcgagt gtcctttctg   7500
caggccttcc atcactttgg agctccctgg gacgtctacc tcggcattcg actgcacaac   7560
gagggtgtgt ggatcttcat gttctttaac tcgttcattc acaccatcat gtacacctac   7620
tatggactga ctgccgctgg ctacaagttc aaggccaagc ctctgatcac tgccatgcag   7680
atttgccagt tcgtcggtgg cttttctcctg gtctgggact acatcaacgt tccctgcttc   7740
aactctgaca agggcaagct gttctcctgg gctttcaact acgcctacgt cggatctgtc   7800
```

```
tttctcctgt tctgtcactt cttttaccag acaacctgg ccaccaagaa atccgctaag    7860
gctggtaagc agctttagc                                                7879

<210> SEQ ID NO 19
<211> LENGTH: 7783
<212> TYPE: DNA
<213> ORGANISM: Artificial Sequence
<220> FEATURE:
<223> OTHER INFORMATION: plasmid pY115

<400> SEQUENCE: 19
catggctctg gccaacgacg ctggcgagcg aatctgggct gccgtcaccg atcccgaaat      60
cctcattggc accttctcct acctgctcct gaagcctctc ctgcgaaact ctggtctcgt     120
ggacgagaag aaaggagcct accgaacctc catgatctgg tacaacgtcc tcctggctct     180
cttctctgcc ctgtccttct acgtgactgc caccgctctc ggctgggact acggtactgg     240
agcctggctg cgaagacaga ccggtgatac tccccagcct ctctttcagt gtccctctcc     300
tgtctgggac tccaagctgt tcacctggac tgccaaggcc ttctactatt ctaagtacgt     360
ggagtacctc gacaccgctt ggctggtcct caagggcaag cgagtgtcct ttctgcaggc     420
cttccatcac tttggagctc cctgggacgt ctacctcggc attcgactgc acaacgaggg     480
tgtgtggatc ttcatgttct taactcgtt cattcacacc atcatgtaca cctactatgg     540
actgactgcc gctggctaca gttcaaggc caagcctctg atcactgcca tgcagatttg     600
ccagttcgtc ggtggctttc tcctggtctg ggactacatc aacgttccct gcttcaactc     660
tgacaagggc aagctgttct cctgggcttt caactacgcc tacgtcggat ctgtctttct     720
cctgttctgt cacttctttt accaggacaa cctggccacc aagaaatccg ctaaggctgg     780
taagcagctt tagcggccgc aagtgtggat ggggaagtga gtgcccggtt ctgtgtgcac     840
aattggcaat ccaagatgga tggattcaac acagggatat agcgagctac gtggtggtgc     900
gaggatatag caacggatat ttatgtttga cacttgagaa tgtacgatac aagcactgtc     960
caagtacaat actaaacata ctgtacatac tcatactcgt acccgggcaa cggttttcact    1020 tgagtgcagt ggctagtgct cttactcgta cagtgtgcaa tactgcgtat catagtctt     1080 gatgtatatc gtattcattc atgttagttg cgtacgagcc ggaagcataa agtgtaaagc    1140
ctggggtgcc taatgagtga gctaactcac attaattgcg ttgcgctcac tgcccgcttt    1200
ccagtcggga aacctgtcgt gccagctgca ttaatgaatc ggccaacgcg cggggagagg    1260
cggtttgcgt attgggcgct cttccgcttc ctcgctcact gactcgctgc gctcggtcgt    1320
tcggctgcgg cgagcggtat cagctcactc aaaggcggta atacggttat ccacagaatc    1380 agggataac gcaggaaaga acatgtgagc aaaaggccag caaaaggcca ggaaccgtaa    1440
aaaggccgcg ttgctggcgt ttttccatag gctccgcccc cctgacgagc atcacaaaaa    1500
tcgacgctca gtcagaggt ggcgaaaccc gacaggacta taaagatacc aggcgtttcc    1560
ccctggaagc tccctcgtgc gctctcctgt tccgaccctg ccgcttaccg gatacctgtc    1620
cgcctttctc ccttcgggaa gcgtggcgct ttctcatagc tcacgctgta ggtatctcag    1680
ttcggtgtag tcgttcgct ccaagctggg ctgtgtgcac gaaccccccg ttcagcccga    1740
ccgctgcgcc ttatccggta actatcgtct tgagtccaac ccggtaagac acgacttatc    1800
gccactggca gcagccactg gtaacaggat tagcagagcg aggtatgtag gcggtgctac    1860
agagttcttg aagtggtggc ctaactacgg ctacactaga aggacagtat ttggtatctg    1920
cgctctgctg aagccagtta ccttcggaaa aagagttggt agctcttgat ccggcaaaca    1980
```

```
aaccaccgct ggtagcggtg gttttttgt ttgcaagcag cagattacgc gcagaaaaaa    2040
aggatctcaa gaagatcctt tgatcttttc tacggggtct gacgctcagt ggaacgaaaa    2100
ctcacgttaa gggattttgg tcatgagatt atcaaaaagg atcttcacct agatcctttt    2160
aaattaaaaa tgaagtttta aatcaatcta agtatatat gagtaaactt ggtctgacag     2220
ttaccaatgc ttaatcagtg aggcacctat ctcagcgatc tgtctatttc gttcatccat    2280
agttgcctga ctccccgtcg tgtagataac tacgatacgg gagggcttac catctggccc    2340
cagtgctgca atgataccgc gagacccacg ctcaccggct ccagatttat cagcaataaa    2400
ccagccagcc ggaagggccg agcgcagaag tggtcctgca actttatccg cctccatcca    2460
gtctattaat tgttgccggg aagctagagt aagtagttcg ccagttaata gtttgcgcaa    2520
cgttgttgcc attgctacag gcatcgtggt gtcacgctcg tcgtttggta tggcttcatt    2580
cagctccggt tcccaacgat caaggcgagt tacatgatcc cccatgttgt gcaaaaaagc    2640
ggttagctcc ttcggtcctc cgatcgttgt cagaagtaag ttggccgcag tgttatcact    2700
catggttatg gcagcactgc ataattctct tactgtcatg ccatccgtaa gatgcttttc    2760
tgtgactggt gagtactcaa ccaagtcatt ctgagaatag tgtatgcggc gaccgagttg    2820
ctcttgcccg gcgtcaatac gggataatac cgcgccacat agcagaactt taaaagtgct    2880
catcattgga aaacgttctt cggggcgaaa actctcaagg atcttaccgc tgttgagatc    2940
cagttcgatg taacccactc gtgcacccaa ctgatcttca gcatctttta ctttcaccag    3000
cgtttctggg tgagcaaaaa caggaaggca aaatgccgca aaaagggaa taagggcgac    3060 acggaaatgt tgaatactca tactcttcct ttttcaatat tattgaagca tttatcaggg    3120
ttattgtctc atgagcggat acatatttga atgtatttag aaaaataaac aaataggggt    3180
tccgcgcaca tttccccgaa aagtgccacc tgacgcgccc tgtagcggcg cattaagcgc    3240
ggcgggtgtg gtggttacgc gcagcgtgac cgctacactt gccagcgccc tagcgcccgc    3300
tcctttcgct ttcttccctt cctttctcgc cacgttcgcc ggctttcccc gtcaagctct    3360
aaatcggggg ctccctttag ggttccgatt tagtgcttta cggcacctcg accccaaaaa    3420
acttgattag ggtgatggtt cacgtagtgg gccatcgccc tgatagacgg ttttttcgcc    3480
tttgacgttg gagtccacgt tctttaatag tggactcttg ttccaaactg gaacaacact    3540
caaccctatc tcggtctatt cttttgattt ataagggatt ttgccgattt cggcctattg    3600
gttaaaaaat gagctgattt aacaaaaatt taacgcgaat tttaacaaaa tattaacgct    3660
tacaatttcc attcgccatt caggctgcgc aactgttggg aagggcgatc ggtgcgggcc    3720
tcttcgctat tacgccagct ggcgaaaggg ggatgtgctg caaggcgatt aagttgggta    3780
acgccagggt tttcccagtc acgacgttgt aaaacgacgg ccagtgaatt gtaatacgac    3840
tcactatagg gcgaattggg taccgggccc ccctcgagg tcgatggtgt cgataagctt    3900
gatatcgaat tcatgtcaca caaaccgatc ttcgcctcaa ggaaacctaa ttctacatcc    3960
gagagactgc cgagatccag tctacactga ttaattttcg ggccaataat ttaaaaaaat    4020
cgtgttatat aatattatat gtattatata tatacatcat gatgatactg acagtcatgt    4080
cccattgcta aatagacaga ctccatctgc cgcctccaac tgatgttctc aatatttaag    4140
gggtcatctc gcattgttta ataataaaca gactccatct accgcctcca aatgatgttc    4200
tcaaaatata ttgtatgaac ttatttttat tacttagtat tattagacaa cttacttgct    4260
ttatgaaaaa cacttcctat ttaggaaaca atttataatg gcagttcgtt catttaacaa    4320
tttatgtaga ataaatgtta taaatgcgta tgggaaatct taaatatgga tagcataaat    4380
```

```
gatatctgca ttgcctaatt cgaaatcaac agcaacgaaa aaaatccctt gtacaacata    4440
aatagtcatc gagaaatatc aactatcaaa gaacagctat tcacacgtta ctattgagat    4500
tattattgga cgagaatcac acactcaact gtctttctct cttctagaaa tacaggtaca    4560
agtatgtact attctcattg ttcatacttc tagtcatttc atcccacata ttccttggat    4620
ttctctccaa tgaatgacat tctatcttgc aaattcaaca attataataa gatataccaa    4680
agtagcggta tagtggcaat caaaaagctt ctctggtgtg cttctcgtat ttattttat     4740 tctaatgatc cattaaaggt atatatttat ttcttgttat ataatccttt tgttattac     4800 atgggctgga tacataaagg tattttgatt taatttttg cttaaattca atcccccctc     4860
gttcagtgtc aactgtaatg gtaggaaatt accatacttt tgaagaagca aaaaaaatga    4920
aagaaaaaaa aaatcgtatt tccaggttag acgttccgca gaatctagaa tgcggtatgc    4980
ggtacattgt tcttcgaacg taaaagttgc gctccctgag atattgtaca ttttgcttt     5040 tacaagtaca agtacatcgt acaactatgt actactgtta tgcatccac aacagtttgt     5100 tttgttttt tttgtttttt tttttctaa tgattcatta ccgctatgta tacctacttg      5160
tacttgtagt aagccgggtt attggcgttc aattaatcat agacttatga atctgcacgg    5220
tgtgcgctgc gagttacttt tagcttatgc atgctacttg ggtgtaatat tgggatctgt    5280
tcggaaatca acgatgctc aatcgatttc gacagtaatt aattaagtca tacacaagtc     5340
agctttcttc gagcctcata taagtataag tagttcaacg tattagcact gtacccagca    5400
tctccgtatc gagaaacaca acaacatgcc ccattggaca gatcatgcgg atacacaggt    5460
tgtgcagtat catacatact cgatcagaca ggtcgtctga ccatcataca agctgaacaa    5520
gcgctccata cttgcacgct ctctatatac acagttaaat tacatatcca tagtctaacc    5580
tctaacagtt aatcttctgg taagcctccc agccagcctt ctggtatcgc ttggcctcct    5640
caataggatc tcggttctgg ccgtacagac ctcggccgac aattatgata tccgttccgg    5700
tagacatgac atcctcaaca gttcggtact gctgtccgag agcgtctccc ttgtcgtcaa    5760
gacccacccc gggggtcaga ataagccagt cctcagagtc gcccttaggt cggttctggg    5820
caatgaagcc aaccacaaac tcggggtcgg atcgggcaag ctcaatggtc tgcttggagt    5880
actcgccagt ggccagagag cccttgcaag acagctcggc cagcatgagc agacctctgg    5940
ccagcttctc gttgggagag gggactagga actccttgta ctgggagttc tcgtagtcag    6000
agacgtcctc cttcttctgt tcagagacag tttcctcggc accagctcgc aggccagcaa    6060
tgattccggt tccgggtaca ccgtgggcgt tggtgatatc ggaccactcg gcgattcggt    6120
gacaccggta ctggtgcttg acagtgttgc caatatctgc gaactttctg tcctcgaaca    6180
ggaagaaacc gtgcttaaga gcaagttcct tgaggggag cacagtgccg gcgtaggtga     6240
agtcgtcaat gatgtcgata tgggttttga tcatgcacac ataaggtccg accttatcgg    6300
caagctcaat gagctccttg gtggtggtaa catccagaga agcacacagg ttggttttct    6360
tggctgccac gagcttgagc actcgagcgg caaaggcgga cttgtggacg ttagctcgag    6420
cttcgtagga gggcattttg gtggtgaaga ggagactgaa ataaatttag tctgcagaac    6480
tttttatcgg aaccttatct ggggcagtga agtatatgtt atggtaatag ttacgagtta    6540
gttgaactta tagatagact ggactatacg gctatcggtc caaattagaa agaacgtcaa    6600
tggctctctg ggcgtcgcct ttgccgacaa aaatgtgatc atgatgaaag ccagcaatga    6660
cgttgcagct gatattgttg tcggccaacc gcgccgaaaa cgcagctgtc agacccacag    6720
cctccaacga agaatgtatc gtcaaagtga tccaagcaca ctcatagttg gagtcgtact    6780
```

```
ccaaaggcgg caatgacgag tcagacagat actcgtcgac gtttaaacag tgtacgcaga    6840
tctactatag aggaacattt aaattgcccc ggagaagacg gccaggccgc ctagatgaca    6900
aattcaacaa ctcacagctg actttctgcc attgccacta ggggggggcc tttttatatg    6960
gccaagccaa gctctccacg tcggttgggc tgcacccaac aataaatggg tagggttgca    7020
ccaacaaagg gatgggatgg ggggtagaag atacgaggat aacggggctc aatggcacaa    7080
ataagaacga atactgccat taagactcgt gatccagcga ctgacaccat tgcatcatct    7140
aagggcctca aaactacctc ggaactgctg cgctgatctg gacaccacag aggttccgag    7200
cactttaggt tgcaccaaat gtcccaccag gtgcaggcag aaaacgctgg aacagcgtgt    7260
acagtttgtc ttaacaaaaa gtgagggcgc tgaggtcgag cagggtggtg tgacttgtta    7320
tagcctttag agctgcgaaa gcgcgtatgg atttggctca tcaggccaga ttgagggtct    7380
gtggacacat gtcatgttag tgtacttcaa tcgcccoctg gatatagccc cgacaatagg    7440
ccgtggcctc attttttgc cttccgcaca tttccattgc tcgatacocca caccttgctt    7500 ctcctgcact tgccaacctt aatactggtt tacattgacc aacatcttac aagcgggggg    7560
cttgtctagg gtatatataa acagtggctc tcccaatcgg ttgccagtct cttttttcct    7620
ttctttcccc acagattcga aatctaaact acacatcaca gaattccgag ccgtgagtat    7680
ccacgacaag atcagtgtcg agacgacgcg ttttgtgtaa tgcacaatc cgaaagtcgc    7740 tagcaacaca cactctctac acaaactaac ccagctctgg tac                     7783

<210> SEQ ID NO 20
<211> LENGTH: 19
<212> TYPE: DNA
<213> ORGANISM: Artificial Sequence
<220> FEATURE:
<223> OTHER INFORMATION: primer oYFBA1

<400> SEQUENCE: 20
acgcagatct actatagag                                                 19

<210> SEQ ID NO 21
<211> LENGTH: 27
<212> TYPE: DNA
<213> ORGANISM: Artificial Sequence
<220> FEATURE:
<223> OTHER INFORMATION: primer oYFBA1-6

<400> SEQUENCE: 21
agcggccgct ggtaccagag ctgggtt                                        27

<210> SEQ ID NO 22
<211> LENGTH: 6992
<212> TYPE: DNA
<213> ORGANISM: Artificial Sequence
<220> FEATURE:
<223> OTHER INFORMATION: plasmid pY158

<400> SEQUENCE: 22
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc ggcaacggtt tcacttgagt gcagtggcta     240
gtgctcttac tcgtacagtg tgcaatactg cgtatcatag tctttgatgt atatcgtatt     300
cattcatgtt agttgcgtac gagccggaag cataaagtgt aaagcctggg gtgcctaatg     360
```

```
agtgagctaa ctcacattaa ttgcgttgcg ctcactgccc gctttccagt cgggaaacct   420
gtcgtgccag ctgcattaat gaatcggcca acgcgcgggg agaggcggtt tgcgtattgg   480
gcgctcttcc gcttcctcgc tcactgactc gctgcgctcg gtcgttcggc tgcggcgagc   540
ggtatcagct cactcaaagg cggtaatacg gttatccaca gaatcagggg ataacgcagg   600
aaagaacatg tgagcaaaag gccagcaaaa ggccaggaac cgtaaaaagg ccgcgttgct   660
ggcgtttttc cataggctcc gcccccctga cgagcatcac aaaaatcgac gctcaagtca   720
gaggtggcga aacccgacag gactataaag ataccaggcg tttccccctg gaagctccct   780
cgtgcgctct cctgttccga ccctgccgct taccggatac ctgtccgcct ttctcccttc   840
gggaagcgtg gcgctttctc atagctcacg ctgtaggtat ctcagttcgg tgtaggtcgt   900
tcgctccaag ctgggctgtg tgcacgaacc ccccgttcag cccgaccgct gcgccttatc   960
cggtaactat cgtcttgagt ccaacccggt aagacacgac ttatcgccac tggcagcagc  1020
cactggtaac aggattagca gagcgaggta tgtaggcggt gctacagagt tcttgaagtg  1080
gtggcctaac tacggctaca ctagaaggac agtatttggt atctgcgctc tgctgaagcc  1140
agttaccttc ggaaaaagag ttggtagctc ttgatccggc aaacaaacca ccgctggtag  1200
cggtggtttt tttgtttgca agcagcagat tacgcgcaga aaaaaggat ctcaagaaga  1260 tcctttgatc ttttctacgg ggtctgacgc tcagtggaac gaaaactcac gttaagggat  1320
tttggtcatg agattatcaa aaaggatctt cacctagatc cttttaaatt aaaaatgaag  1380
ttttaaatca atctaaagta tatatgagta aacttggtct gacagttacc aatgcttaat  1440
cagtgaggca cctatctcag cgatctgtct atttcgttca tccatagttg cctgactccc  1500
cgtcgtgtag ataactacga tacgggaggg cttaccatct ggccccagtg ctgcaatgat  1560
accgcgagac ccacgctcac cggctccaga tttatcagca ataaaccagc cagccggaag  1620
ggccgagcgc agaagtggtc ctgcaacttt atccgcctcc atccagtcta ttaattgttg  1680
ccgggaagct agagtaagta gttcgccagt taatagtttg cgcaacgttg ttgccattgc  1740
tacaggcatc gtggtgtcac gctcgtcgtt tggtatggct tcattcagct ccggttccca  1800
acgatcaagg cgagttacat gatcccccat gttgtgcaaa aaagcggtta gctccttcgg  1860
tcctccgatc gttgtcagaa gtaagttggc cgcagtgtta tcactcatgg ttatggcagc  1920
actgcataat tctcttactg tcatgccatc cgtaagatgc ttttctgtga ctggtgagta  1980
ctcaaccaag tcattctgag aatagtgtat gcggcgaccg agttgctctt gcccggcgtc  2040
aatacgggat aataccgcgc cacatagcag aactttaaaa gtgctcatca ttggaaaacg  2100
ttcttcgggg cgaaaactct caaggatctt accgctgttg agatccagtt cgatgtaacc  2160
cactcgtgca cccaactgat cttcagcatc ttttactttc accagcgttt ctgggtgagc  2220
aaaaacagga aggcaaaatg ccgcaaaaaa gggaataagg gcgacacgga aatgttgaat  2280
actcatactc ttcctttttc aatattattg aagcatttat cagggttatt gtctcatgag  2340
cggatacata tttgaatgta tttagaaaaa taaacaaata ggggttccgc gcacatttcc  2400
ccgaaaagtg ccacctgacg cgccctgtag cggcgcatta agcgcggcgg gtgtggtggt  2460
tacgcgcagc gtgaccgcta cacttgccag cgccctagcg cccgctcctt tcgctttctt  2520
cccttccttt ctcgccacgt tcgccggctt tccccgtcaa gctctaaatc ggggctccc  2580 tttagggttc cgatttagtg ctttacggca cctcgacccc aaaaaacttg attagggtga  2640
tggttcacgt agtgggccat cgccctgata gacggttttt cgccctttga cgttggagtc  2700
cacgttcttt aatagtggac tcttgttcca aactggaaca acactcaacc ctatctcggt  2760
```

```
ctattcttttt gatttataag ggattttgcc gatttcggcc tattggttaa aaaatgagct    2820
gatttaacaa aaatttaacg cgaattttaa caaaatatta acgcttacaa tttccattcg    2880
ccattcaggc tgcgcaactg ttgggaaggg cgatcggtgc gggcctcttc gctattacgc    2940
cagctggcga aggggggatg tgctgcaagg cgattaagtt gggtaacgcc agggttttcc    3000
cagtcacgac gttgtaaaac gacggccagt gaattgtaat acgactcact atagggcgaa    3060
ttgggtaccg ggccccccct cgaggtcgat ggtgtcgata agcttgatat cgaattcatg    3120
tcacacaaac cgatcttcgc ctcaaggaaa cctaattcta catccgagag actgccgaga    3180
tccagtctac actgattaat tttcgggcca ataatttaaa aaaatcgtgt tatataatat    3240
tatatgtatt atatatatac atcatgatga tactgacagt catgtcccat tgctaaatag    3300
acagactcca tctgccgcct ccaactgatg ttctcaatat ttaaggggtc atctcgcatt    3360
gtttaataat aaacagactc catctaccgc ctccaaatga tgttctcaaa atatattgta    3420
tgaacttatt tttattactt agtattatta gacaacttac ttgctttatg aaaaacactt    3480
cctatttagg aaacaattta taatggcagt tcgttcattt aacaatttat gtagaataaa    3540
tgttataaat gcgtatggga atcttaaat atggatagca taaatgatat ctgcattgcc    3600
taattcgaaa tcaacagcaa cgaaaaaaat cccttgtaca acataaatag tcatcgagaa    3660
atatcaacta tcaaagaaca gctattcaca cgttactatt gagattatta ttggacgaga    3720
atcacacact caactgtctt tctctcttct agaaatacag gtacaagtat gtactattct    3780
cattgttcat acttctagtc atttcatccc acatattcct tggatttctc tccaatgaat    3840
gacattctat cttgcaaatt caacaattat aataagatat accaaagtag cggtatagtg    3900
gcaatcaaaa agcttctctg gtgtgcttct cgtatttatt tttattctaa tgatccatta    3960
aaggtatata tttatttctt gttatataat cctttttgttt attacatggg ctggatacat    4020
aaaggtattt tgatttaatt ttttgcttaa attcaatccc ccctcgttca gtgtcaactg    4080
taatggtagg aaattaccat acttttgaag aagcaaaaaa aatgaaagaa aaaaaaaatc    4140
gtatttccag gttagacgtt ccgcagaatc tagaatgcgg tatgcggtac attgttcttc    4200
gaacgtaaaa gttgcgctcc ctgagatatt gtacattttt gcttttacaa gtacaagtac    4260
atcgtacaac tatgtactac tgttgatgca tccacaacag tttgtttttgt ttttttttgt    4320 tttttttttt tctaatgatt cattaccgct atgtatacct acttgtactt gtagtaagcc    4380
gggttattgg cgttcaatta atcatagact tatgaatctg cacggtgtgc gctgcgagtt    4440
acttttagct tatgcatgct acttgggtgt aatattggga tctgttcgga aatcaacgga    4500
tgctcaatcg atttcgacag taattaatta agtcatacac aagtcagctt tcttcgagcc    4560
tcatataagt ataagtagtt caacgtatta gcactgtacc cagcatctcc gtatcgagaa    4620
acacaacaac atgccccatt ggacagatca tgcggataca caggttgtgc agtatcatac    4680
atactcgatc agacaggtcg tctgaccatc atacaagctg aacaagcgct ccatacttgc    4740
acgctctcta tatacacagt taaattacat atccatagtc taacctctaa cagttaatct    4800
tctggtaagc ctcccagcca gccttctggt atcgcttggc ctcctcaata ggatctcggt    4860
tctggccgta cagacctcgg ccgacaatta tgatatccgt tccggtagac atgcatcct    4920 caacagttcg gtactgctgt ccgagagcgt ctcccttgtc gtcaagaccc accccggggg    4980
tcagaataag ccagtcctca gagtcgccct taggtcggtt ctgggcaatg aagccaacca    5040
caaactcggg gtcggatcgg gcaagctcaa tggtctgctt ggagtactcg ccagtggcca    5100
gagagccctt gcaagacagc tcggccagca tgagcagacc tctgccagc ttctcgttgg    5160
```

```
gagaggggac taggaactcc ttgtactggg agttctcgta gtcagagacg tcctccttct    5220
tctgttcaga gacagtttcc tcggcaccag ctcgcaggcc agcaatgatt ccggttccgg    5280
gtacaccgtg ggcgttggtg atatcggacc actcggcgat tcggtgacac cggtactggt    5340
gcttgacagt gttgccaata tctgcgaact ttctgtcctc gaacaggaag aaaccgtgct    5400
taagagcaag ttccttgagg gggagcacag tgccggcgta ggtgaagtcg tcaatgatgt    5460
cgatatgggt tttgatcatg cacacataag gtccgacctt atcggcaagc tcaatgagct    5520
ccttggtggt ggtaacatcc agagaagcac acaggttggt tttcttggct gccacgagct    5580
tgagcactcg agcggcaaag gcggacttgt ggacgttagc tcgagcttcg taggagggca    5640
ttttggtggt gaagaggaga ctgaaataaa tttagtctgc agaacttttt atcggaacct    5700
tatctggggc agtgaagtat atgttatggt aatagttacg agttagttga acttatagat    5760
agactggact atacggctat cggtccaaat tagaaagaac gtcaatggct ctctgggcgt    5820
cgcctttgcc gacaaaaatg tgatcatgat gaaagccagc aatgacgttg cagctgatat    5880
tgttgtcggc caaccgcgcc gaaaacgcag ctgtcagacc cacagcctcc aacgaagaat    5940
gtatcgtcaa agtgatccaa gcacactcat agttggagtc gtactccaaa ggcggcaatg    6000
acgagtcaga cagatactcg tcgacgttta acagtgtac gcagatctac tatagaggaa    6060
catttaaatt gccccggaga agacggccag gccgcctaga tgacaaattc aacaactcac    6120
agctgacttt ctgccattgc cactaggggg gggccttttt atatggccaa gccaagctct    6180
ccacgtcggt tgggctgcac ccaacaataa atgggtaggg ttgcaccaac aaagggatgg    6240
gatggggggt agaagatacg aggataacgg ggctcaatgg cacaaataag aacgaatact    6300
gccattaaga ctcgtgatcc agcgactgac accattgcat catctaaggg cctcaaaact    6360
acctcggaac tgctgcgctg atctggacac cacagaggtt ccgagcactt taggttgcac    6420
caaatgtccc accaggtgca ggcagaaaac gctggaacag cgtgtacagt ttgtcttagc    6480
aaaaagtgaa ggcgctgagg tcgagcaggg tggtgtgact tgttatagcc tttagagctg    6540
cgaaagcgcg tatggatttg gctcatcagg ccagattgag ggtctgtgga cacatgtcat    6600
gttagtgtac ttcaatcgcc ccctggatat agccccgaca ataggccgtg gcctcatttt    6660
tttgccttcc gcacatttcc attgctcgat acccacacct tgcttctcct gcacttgcca    6720
accttaatac tggtttacat tgaccaacat cttacaagcg gggggcttgt ctagggtata    6780
tataaacagt ggctctccca atcggttgcc agtctctttt ttcctttctt tccccacaga    6840
ttcgaaatct aaactacaca tcacagaatt ccgagccgtg agtatccacg acaagatcag    6900
tgtcgagacg acgcgttttg tgtaatgaca caatccgaaa gtcgctagca acacacactc    6960
tctacacaaa ctaacccagc tctggtacca gc                                  6992
```

<210> SEQ ID NO 23
<211> LENGTH: 8707
<212> TYPE: DNA
<213> ORGANISM: Artificial Sequence
<220> FEATURE:
<223> OTHER INFORMATION: plasmid pY159

<400> SEQUENCE: 23

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc ggcaacggtt tcacttgagt gcagtggcta     240
```

```
gtgctcttac tcgtacagtg tgcaatactg cgtatcatag tctttgatgt atatcgtatt    300
cattcatgtt agttgcgtac gagccggaag cataaagtgt aaagcctggg gtgcctaatg    360
agtgagctaa ctcacattaa ttgcgttgcg ctcactgccc gctttccagt cgggaaacct    420
gtcgtgccag ctgcattaat gaatcggcca acgcgcgggg agaggcggtt tgcgtattgg    480
gcgctcttcc gcttcctcgc tcactgactc gctgcgctcg gtcgttcggc tgcggcgagc    540
ggtatcagct cactcaaagg cggtaatacg gttatccaca gaatcagggg ataacgcagg    600
aaagaacatg tgagcaaaag gccagcaaaa ggccaggaac cgtaaaaagg ccgcgttgct    660
ggcgttttc cataggctcc gcccccctga cgagcatcac aaaaatcgac gctcaagtca    720
gaggtggcga acccgacag gactataaag ataccaggcg tttccccctg aagctccct    780
cgtgcgctct cctgttccga ccctgccgct taccggatac ctgtccgcct ttctcccttc    840
gggaagcgtg cgctttctc atagctcacg ctgtaggtat ctcagttcgg tgtaggtcgt    900
tcgctccaag ctgggctgtg tgcacgaacc ccccgttcag cccgaccgct gcgccttatc    960
cggtaactat cgtcttgagt ccaacccggt aagacacgac ttatcgccac tggcagcagc   1020
cactggtaac aggattagca gagcgaggta tgtaggcggt gctacagagt tcttgaagtg   1080
gtggcctaac tacggctaca ctagaaggac agtatttggt atctgcgctc tgctgaagcc   1140
agttaccttc ggaaaaagag ttggtagctc ttgatccggc aaacaaacca ccgctggtag   1200
cggtggtttt tttgtttgca agcagcagat tacgcgcaga aaaaaggat ctcaagaaga   1260
tcctttgatc ttttctacgg ggtctgacgc tcagtggaac gaaaactcac gttaagggat   1320
tttggtcatg agattatcaa aaaggatctt cacctagatc cttttaaatt aaaaatgaag   1380
ttttaaatca atctaaagta tatatgagta aacttggtct gacagttacc aatgcttaat   1440
cagtgaggca cctatctcag cgatctgtct atttcgttca tccatagttg cctgactccc   1500
cgtcgtgtag ataactacga tacgggaggg cttaccatct ggccccagtg ctgcaatgat   1560
accgcgagac ccacgctcac cggctccaga tttatcagca ataaaccagc cagccggaag   1620
ggccgagcgc agaagtggtc ctgcaacttt atccgcctcc atccagtcta ttaattgttg   1680
ccgggaagct agagtaagta gttcgccagt taatagtttg cgcaacgttg ttgccattgc   1740
tacaggcatc gtggtgtcac gctcgtcgtt tggtatggct tcattcagct ccggttccca   1800
acgatcaagg cgagttacat gatccccat gttgtgcaaa aaagcggtta gctccttcgg   1860
tcctccgatc gttgtcagaa gtaagttggc cgcagtgtta tcactcatgg ttatggcagc   1920
actgcataat tctcttactg tcatgccatc cgtaagatgc ttttctgtga ctggtgagta   1980
ctcaaccaag tcattctgag aatagtgtat gcggcgaccg agttgctctt gcccggcgtc   2040
aatacgggat aataccgcgc cacatagcag aactttaaaa gtgctcatca ttggaaaacg   2100
ttcttcgggg cgaaaactct caaggatctt accgctgttg agatccagtt cgatgtaacc   2160
cactcgtgca cccaactgat cttcagcatc ttttactttc accagcgttt ctgggtgagc   2220
aaaaacagga aggcaaaatg ccgcaaaaaa gggaataagg gcgacacgga aatgttgaat   2280
actcatactc ttcctttttc aatattattg aagcatttat cagggttatt gtctcatgag   2340
cggatacata tttgaatgta tttagaaaaa taaacaaata ggggttccgc gcacatttcc   2400
ccgaaaagtg ccacctgacg cgccctgtag cggcgcatta agcgcggcgg gtgtggtggt   2460
tacgcgcagc gtgaccgcta cacttgccag cgccctagcg cccgctcctt tcgctttctt   2520
cccttccttt ctcgccacgt tcgccggctt tccccgtcaa gctctaaatc ggggctccc    2580
tttagggttc cgatttagtg ctttacggca cctcgacccc aaaaaacttg attagggtga   2640
```

```
tggttcacgt agtgggccat cgccctgata gacggttttt cgcccttga cgttggagtc    2700 cacgttcttt aatagtggac tcttgttcca aactggaaca acactcaacc ctatctcggt    2760
ctattctttt gatttataag ggattttgcc gatttcggcc tattggttaa aaaatgagct    2820
gatttaacaa aaatttaacg cgaattttaa caaaatatta acgcttacaa tttccattcg    2880
ccattcaggc tgcgcaactg ttgggaaggg cgatcggtgc gggcctcttc gctattacgc    2940
cagctggcga aggggggatg tgctgcaagg cgattaagtt gggtaacgcc agggttttcc    3000
cagtcacgac gttgtaaaac gacggccagt gaattgtaat acgactcact ataggcgaa    3060 ttgggtaccg ggccccccct cgaggtcgat ggtgtcgata agcttgatat cgaattcatg    3120
tcacacaaac cgatcttcgc ctcaaggaaa cctaattcta catccgagag actgccgaga    3180
tccagtctac actgattaat tttcgggcca ataatttaaa aaaatcgtgt tatataatat    3240
tatatgtatt atatatatac atcatgatga tactgacagt catgtcccat tgctaaatag    3300
acagactcca tctgccgcct ccaactgatg ttctcaatat ttaaggggtc atctcgcatt    3360
gtttaataat aaacagactc catctaccgc ctccaaatga tgttctcaaa atatattgta    3420
tgaacttatt tttattactt agtattatta gacaacttac ttgctttatg aaaaacactt    3480
cctatttagg aaacaattta taatggcagt tcgttcattt aacaatttat gtagaataaa    3540
tgttataaat gcgtatggga atcttaaat atggatagca taaatgatat ctgcattgcc    3600
taattcgaaa tcaacagcaa cgaaaaaaat cccttgtaca acataaatag tcatcgagaa    3660
atatcaacta tcaaagaaca gctattcaca cgttactatt gagattatta ttggacgaga    3720
atcacacact caactgtctt tctctcttct agaaatacag gtacaagtat gtactattct    3780
cattgttcat acttctagtc atttcatccc acatattcct tggatttctc tccaatgaat    3840
gacattctat cttgcaaatt caacaattat aataagatat accaaagtag cggtatagtg    3900
gcaatcaaaa agcttctctg gtgtgcttct cgtatttatt tttattctaa tgatccatta    3960
aaggtatata tttatttctt gttatataat ccttttgttt attacatggg ctggatacat    4020
aaaggtattt tgatttaatt ttttgcttaa attcaatccc ccctcgttca gtgtcaactg    4080
taatggtagg aaattaccat acttttgaag aagcaaaaaa aatgaaagaa aaaaaaatc    4140 gtatttccag gttagacgtt ccgcagaatc tagaatgcgg tatgcggtac attgttcttc    4200
gaacgtaaaa gttgcgctcc ctgagatatt gtacattttt gcttttacaa gtacaagtac    4260
atcgtacaac tatgtactac tgttgatgca tccacaacag tttgttttgt ttttttttgt    4320 ttttttttt tctaatgatt cattaccgct atgtatacct acttgtactt gtagtaagcc    4380
gggttattgg cgttcaatta atcatagact tatgaatctg cacggtgtgc gctgcgagtt    4440
acttttagct tatgcatgct acttgggtgt aatattggga tctgttcgga aatcaacgga    4500
tgctcaatcg atttcgacag taattaatta agtcatacac aagtcagctt tcttcgagcc    4560
tcatataagt ataagtagtt caacgtatta gcactgtacc cagcatctcc gtatcgagaa    4620
acacaacaac atgccccatt ggacagatca tgcggataca caggttgtgc agtatcatac    4680
atactcgatc agacaggtcg tctgaccatc atacaagctg aacaagcgct ccatacttgc    4740
acgctctcta tatacacagt taaattacat atccatagtc taacctctaa cagttaatct    4800
tctggtaagc ctcccagcca gccttctggt atcgcttggc ctcctcaata ggatctcggt    4860
tctggccgta cagacctcgg ccgacaatta tgatatccgt tccggtagac atgacatcct    4920
caacagttcg gtactgctgt ccgagagcgt ctcccttgtc gtcaagaccc accccggggg    4980
tcagaataag ccagtcctca gagtcgccct taggtcggtt ctgggcaatg aagccaacca    5040
```

```
caaactcggg gtcggatcgg gcaagctcaa tggtctgctt ggagtactcg ccagtggcca    5100
gagagccctt gcaagacagc tcggccagca tgagcagacc tctggccagc ttctcgttgg    5160
gagagsggac taggaactcc ttgtactggg agttctcgta gtcagagacg tcctccttct    5220
tctgttcaga gacagtttcc tcggcaccag ctcgcaggcc agcaatgatt ccggttccgg    5280
gtacaccgtg ggcgttggtg atatcggacc actcggcgat tcggtgacac cggtactggt    5340
gcttgacagt gttgccaata tctgcgaact ttctgtcctc gaacaggaag aaaccgtgct    5400
taagagcaag ttccttgagg gggagcacag tgccggcgta ggtgaagtcg tcaatgatgt    5460
cgatatgggt tttgatcatg cacacataag gtccgacctt atcggcaagc tcaatgagct    5520
ccttggtggt ggtaacatcc agagaagcac acaggttggt tttcttggct gccacgagct    5580
tgagcactcg agcggcaaag gcggacttgt ggacgttagc tcgagcttcg taggagggca    5640
ttttggtggt gaagaggaga ctgaaataaa tttagtctgc agaacttttt atcggaacct    5700
tatctggggc agtgaagtat atgttatggt aatagttacg agttagttga acttatagat    5760
agactggact atacggctat cggtccaaat tagaaagaac gtcaatggct ctctgggcgt    5820
cgcctttgcc gacaaaaatg tgatcatgat gaaagccagc aatgacgttg cagctgatat    5880
tgttgtcggc caaccgcgcc gaaaacgcag ctgtcagacc cacagcctcc aacgaagaat    5940
gtatcgtcaa agtgatccaa gcacactcat agttggagtc gtactccaaa ggcggcaatg    6000
acgagtcaga cagatactcg tcgacgttta acagtgtac gcagatctac tatagaggaa    6060
catttaaatt gccccggaga agacggccag gccgcctaga tgacaaattc aacaactcac    6120
agctgacttt ctgccattgc cactaggggg gggccttttt atatggccaa gccaagctct    6180
ccacgtcggt tgggctgcac ccaacaataa atgggtaggg ttgcaccaac aaagggatgg    6240 gatgggggt agaagatacg aggataacgg ggctcaatgg cacaaataag aacgaatact    6300
gccattaaga ctcgtgatcc agcgactgac accattgcat catctaaggg cctcaaaact    6360
acctcggaac tgctgcgctg atctggacac cacagaggtt ccgagcactt taggttgcac    6420
caaatgtccc accaggtgca ggcagaaaac gctggaacag cgtgtacagt ttgtcttagc    6480
aaaaagtgaa ggcgctgagg tcgagcaggg tggtgtgact tgttatagcc tttagagctg    6540
cgaaagcgcg tatggatttg gctcatcagg ccagattgag ggtctgtgga cacatgtcat    6600
gttagtgtac ttcaatcgcc ccctggatat agccccgaca ataggccgtg gcctcatttt    6660
tttgccttcc gcacatttcc attgctcgat acccacacct tgcttctcct gcacttgcca    6720
accttaatac tggtttacat tgaccaacat cttacaagcg ggggcttgt ctagggtata    6780 tataaacagt ggctctccca atcggttgcc agtctctttt ttcctttctt tccccacaga    6840
ttcgaaatct aaactacaca tcacagaatt ccgagccgtg agtatccacg acaagatcag    6900
tgtcgagacg acgcgttttg tgtaatgaca caatccgaaa gtcgctagca acacacactc    6960
tctacacaaa ctaacccagc tctggtacca gcggccatca caagtttgta caaaaaagct    7020
gaacgagaaa cgtaaaatga tataaatatc aatatattaa attagatttt gcataaaaaa    7080
cagactacat aatactgtaa aacacaacat atccagtcat attggcggcc gcattaggca    7140
ccccaggctt tacactttat gcttccggct cgtataatgt gtggattttg agttaggatc    7200
cgtcgagatt ttcaggagct aaggaagcta aatggagaa aaaatcact ggatatacca    7260 ccgttgatat atcccaatgg catcgtaaag aacattttga ggcatttcag tcagttgctc    7320
aatgtaccta taaccagacc gttcagctgg atattacggc ctttttaaag accgtaaaga    7380
aaaataagca caagttttat ccggccttta ttcacattct tgcccgcctg atgaatgctc    7440
```

```
atccggaatt ccgtatggca atgaaagacg gtgagctggt gatatgggat agtgttcacc    7500
cttgttacac cgttttccat gagcaaactg aaacgttttc atcgctctgg agtgaatacc    7560
acgacgattt ccggcagttt ctacacatat attcgcaaga tgtggcgtgt tacggtgaaa    7620
acctggccta tttccctaaa gggtttattg agaatatgtt tttcgtctca gccaatccct    7680
gggtgagttt caccagtttt gatttaaacg tggccaatat ggacaacttc ttcgcccccg    7740
ttttcaccat gggcaaatat tatacgcaag gcgacaaggt gctgatgccg ctggcgattc    7800
aggttcatca tgccgtttgt gatggcttcc atgtcggcag aatgcttaat gaattacaac    7860
agtactgcga tgagtggcag ggcggggcgt aaacgcgtgg atccggctta ctaaaagcca    7920
gataacagta tgcgtatttg cgcgctgatt tttgcggtat aagaatatat actgatatgt    7980 atcccgaag tatgtcaaaa agaggtatgc tatgaagcag cgtattacag tgacagttga    8040
cagcgacagc tatcagttgc tcaaggcata tgatgtca atatctccgg tctggtaagc    8100
acaaccatgc agaatgaagc ccgtcgtctg cgtgccgaac gctggaaagc ggaaaatcag    8160
gaagggatgg ctgaggtcgc ccggtttatt gaaatgaacg gctcttttgc tgacgagaac    8220
aggggctggt gaaatgcagt ttaaggttta cacctataaa agagagagcc gttatcgtct    8280
gtttgtggat gtacagagtg atattattga cacgcccggg cgacggatgg tgatccccct    8340
ggccagtgca cgtctgctgt cagataaagt ctcccgtgaa ctttaccccgg tggtgcatat    8400 cggggatgaa agctggcgca tgatgaccac cgatatggcc agtgtgccgg tctccgttat    8460
cggggaagaa gtggctgatc tcagccaccg cgaaaatgac atcaaaaacg ccattaacct    8520
gatgttctgg ggaatataaa tgtcaggctc ccttatacac agccagtctg caggtcgacc    8580
atagtgactg gatatgttgt gttttacagc attatgtagt ctgttttta tgcaaaatct    8640 aatttaatat attgatattt atatcatttt acgtttctcg ttcagctttc ttgtacaaag    8700
tggtgat                                                             8707

<210> SEQ ID NO 24
<211> LENGTH: 8219
<212> TYPE: DNA
<213> ORGANISM: Artificial Sequence
<220> FEATURE:
<223> OTHER INFORMATION: plasmid pY173
<220> FEATURE:
<221> NAME/KEY: misc_feature
<222> LOCATION: (8170)..(8209)
<223> OTHER INFORMATION: n is a, c, g, or t

<400> SEQUENCE: 24
cttgtacaaa gtggtgatgg ccgcaagtgt ggatggggaa gtgagtgccc ggttctgtgt      60
gcacaattgg caatccaaga tggatggatt caacacaggg atatagcgag ctacgtggtg     120
gtgcgaggat atagcaacgg atatttatgt ttgacacttg agaatgtacg atacaagcac     180
tgtccaagta caatactaaa catactgtac atactcatac tcgtacccgg caacggtttc     240
acttgagtgc agtggctagt gctcttactc gtacagtgtg caatactgcg tatcatagtc     300
tttgatgtat atcgtattca ttcatgttag ttgcgtacga gccggaagca taaagtgtaa     360
agcctggggt gcctaatgag tgagctaact cacattaatt gcgttgcgct cactgcccgc     420
tttccagtcg ggaaacctgt cgtgccagct gcattaatga atcggccaac gcgcggggag     480
aggcggtttg cgtattgggc gctcttccgc ttcctcgctc actgactcgc tgcgctcggt     540
cgttcggctg cggcgagcgg tatcagctca ctcaaaggcg gtaatacggt tatccacaga     600
atcaggggat aacgcaggaa agaacatgtg agcaaaaggc cagcaaaagg ccaggaaccg     660
```

```
taaaaaggcc gcgttgctgg cgttttccca taggctccgc cccctgacg agcatcacaa    720 aaatcgacgc tcaagtcaga ggtggcgaaa cccgacagga ctataaagat accaggcgtt   780
tccccctgga agctccctcg tgcgctctcc tgttccgacc ctgccgctta ccggatacct   840
gtccgccttt ctcccttcgg gaagcgtggc gctttctcat agctcacgct gtaggtatct   900
cagttcggtg taggtcgttc gctccaagct gggctgtgtg cacgaacccc ccgttcagcc   960
cgaccgctgc gccttatccg gtaactatcg tcttgagtcc aacccggtaa gacacgactt  1020
atcgccactg gcagcagcca ctggtaacag gattagcaga gcgaggtatg taggcggtgc  1080
tacagagttc ttgaagtggt ggcctaacta cggctacact agaaggacag tatttggtat  1140
ctgcgctctg ctgaagccag ttaccttcgg aaaagagtt ggtagctctt gatccggcaa   1200
acaaaccacc gctggtagcg gtggtttttt tgtttgcaag cagcagatta cgcgcagaaa  1260
aaaaggatct caagaagatc ctttgatctt ttctacgggg tctgacgctc agtggaacga  1320
aaactcacgt taagggattt tggtcatgag attatcaaaa aggatcttca cctagatcct  1380
tttaaattaa aaatgaagtt ttaaatcaat ctaaagtata tatgagtaaa cttggtctga  1440
cagttaccaa tgcttaatca gtgaggcacc tatctcagcg atctgtctat ttcgttcatc  1500
catagttgcc tgactccccg tcgtgtagat aactacgata cgggagggct taccatctgg  1560
ccccagtgct gcaatgatac cgcgagaccc acgctcaccg gctccagatt tatcagcaat  1620
aaaccagcca gccggaaggg ccgagcgcag aagtggtcct gcaactttat ccgcctccat  1680
ccagtctatt aattgttgcc gggaagctag agtaagtagt tcgccagtta atagtttgcg  1740
caacgttgtt gccattgcta caggcatcgt ggtgtcacgc tcgtcgtttg gtatggcttc  1800
attcagctcc ggttcccaac gatcaaggcg agttacatga tcccccatgt tgtgcaaaaa  1860
agcggttagc tccttcggtc ctccgatcgt tgtcagaagt aagttggccg cagtgttatc  1920
actcatggtt atggcagcac tgcataattc tcttactgtc atgccatccg taagatgctt  1980
ttctgtgact ggtgagtact caaccaagtc attctgagaa tagtgtatgc ggcgaccgag  2040
ttgctcttgc ccggcgtcaa tacgggataa taccgcgcca catagcagaa ctttaaaagt  2100
gctcatcatt ggaaaacgtt cttcggggcg aaaactctca aggatcttac cgctgttgag  2160
atccagttcg atgtaaccca ctcgtgcacc caactgatct tcagcatctt ttactttcac  2220
cagcgtttct gggtgagcaa aaacaggaag gcaaaatgcc gcaaaaaagg gaataagggc  2280
gacacggaaa tgttgaatac tcatactctt cctttttcaa tattattgaa gcatttatca  2340
gggttattgt ctcatgagcg gatacatatt tgaatgtatt tagaaaaata aacaaatagg  2400
ggttccgcgc acatttcccc gaaaagtgcc acctgacgcg ccctgtagcg cgcattaag   2460 cgcggcgggt gtggtggtta cgcgcagcgt gaccgctaca cttgccagcg ccctagcgcc  2520
cgctcctttc gctttcttcc cttcctttct cgccacgttc gccggctttc cccgtcaagc  2580
tctaaatcgg gggctccctt tagggttccg atttagtgct ttacggcacc tcgaccccaa  2640
aaaacttgat tagggtgatg gttcacgtag tgggccatcg ccctgataga cggttttcg   2700 ccctttgacg ttggagtcca cgttctttaa tagtggactc ttgttccaaa ctggaacaac  2760
actcaaccct atctcggtct attctttga tttataaggg attttgccga tttcggccta   2820
ttggttaaaa aatgagctga tttaacaaaa atttaacgcg aattttaaca aaatattaac  2880
gcttacaatt ccattcgcc attcaggctg cgcaactgtt gggaagggcg atcggtgcgg   2940
gcctcttcgc tattacgcca gctggcgaaa ggggatgtg ctgcaaggcg attaagttgg    3000
gtaacgccag ggttttccca gtcacgacgt tgtaaaacga cggccagtga attgtaatac  3060
```

```
gactcactat agggcgaatt gggtaccggg ccccccctcg aggtcgatgg tgtcgataag    3120
cttgatatcg aattcatgtc acacaaaccg atcttcgcct caaggaaacc taattctaca    3180
tccgagagac tgccgagatc cagtctacac tgattaattt tcgggccaat aatttaaaaa    3240
aatcgtgtta tataatatta tatgtattat atatatacat catgatgata ctgacagtca    3300
tgtcccattg ctaaatagac agactccatc tgccgcctcc aactgatgtt ctcaatattt    3360 aagggtcat ctcgcattgt ttaataataa acagactcca tctaccgcct ccaaatgatg    3420
ttctcaaaat atattgtatg aacttatttt tattacttag tattattaga caacttactt    3480
gctttatgaa aaacacttcc tatttaggaa acaatttata atggcagttc gttcatttaa    3540
caatttatgt agaataaatg ttataaatgc gtatgggaaa tcttaaatat ggatagcata    3600
aatgatatct gcattgccta attcgaaatc aacagcaacg aaaaaaatcc cttgtacaac    3660
ataaatagtc atcgagaaat atcaactatc aagaacagc tattcacacg ttactattga    3720
gattattatt ggacgagaat cacacactca actgtctttc tctcttctag aaatacaggt    3780
acaagtatgt actattctca ttgttcatac ttctagtcat ttcatcccac atattccttg    3840
gatttctctc caatgaatga cattctatct tgcaaattca acaattataa taagatatac    3900
caaagtagcg gtatagtggc aatcaaaaag cttctctggt gtgcttctcg tatttatttt    3960
tattctaatg atccattaaa ggtatatatt tatttcttgt tatataatcc ttttgtttat    4020
tacatgggct ggatacataa aggtatttg atttaatttt ttgcttaaat tcaatccccc    4080
ctcgttcagt gtcaactgta atggtaggaa attaccatac ttttgaagaa gcaaaaaaaa    4140
tgaaagaaaa aaaaaatcgt atttccaggt tagacgttcc gcagaatcta gaatgcggta    4200
tgcggtacat tgttcttcga acgtaaaagt tgcgctccct gagatattgt acattttgc    4260 ttttacaagt acaagtacat cgtacaacta tgtactactg ttgatgcatc cacaacagtt    4320
tgttttgttt ttttttgttt ttttttttc taatgattca ttaccgctat gtataccta    4380 ttgtacttgt agtaagccgg gttattggcg ttcaattaat catagactta tgaatctgca    4440
cggtgtgcgc tgcgagttac ttttagctta tgcatgctac ttgggtgtaa tattgggatc    4500
tgttcggaaa tcaacggatg ctcaatcgat ttcgacagta attaattaag tcatacacaa    4560
gtcagctttc ttcgagcctc atataagtat aagtagttca acgtattagc actgtaccca    4620
gcatctccgt atcgagaaac acaacaacat gccccattgg acagatcatg cggatacaca    4680
ggttgtgcag tatcatacat actcgatcag acaggtcgtc tgaccatcat acaagctgaa    4740
caagcgctcc atacttgcac gctctctata tacacagtta aattacatat ccatagtcta    4800
acctctaaca gttaatcttc tggtaagcct cccagccagc cttctggtat cgcttggcct    4860
cctcaatagg atctcggttc tggccgtaca gacctcggcc gacaattatg atatccgttc    4920
cggtagacat gacatcctca acagttcggt actgctgtcc gagagcgtct cccttgtcgt    4980
caagacccac cccggggtc agaataagcc agtcctcaga gtcgcccta ggtcggttct    5040 gggcaatgaa gccaaccaca aactcggggt cggatcgggc aagctcaatg gtctgcttgg    5100
agtactcgcc agtggccaga gagcccttgc aagacagctc ggccagcatg agcagacctc    5160
tggccagctt ctcgttggga gaggggacta ggaactcctt gtactgggag ttctcgtagt    5220
cagagacgtc ctccttcttc tgttcagaga cagtttcctc ggcaccagct cgcaggccag    5280
caatgattcc ggttccgggt acaccgtggg cgttggtgat atcggaccac tcggcgattc    5340
ggtgacaccg gtactggtgc ttgacagtgt tgccaatatc tgcgaacttt ctgtcctcga    5400
acaggaagaa accgtgctta agagcaagtt ccttgagggg gagcacagtg ccggcgtagg    5460
```

```
tgaagtcgtc aatgatgtcg atatgggttt tgatcatgca cacataaggt ccgaccttat   5520
cggcaagctc aatgagctcc ttggtggtgg taacatccag agaagcacac aggttggttt   5580
tcttggctgc cacagagcttg agcactcgag cggcaaaggc ggacttgtgg acgttagctc  5640
gagcttcgta ggagggcatt tggtggtga agaggagact gaaataaatt tagtctgcag    5700
aactttttat cggaacctta tctggggcag tgaagtatat gttatggtaa tagttacgag   5760
ttagttgaac ttatagatag actggactat acggctatcg gtccaaatta gaaagaacgt   5820
caatggctct ctgggcgtcg cctttgccga caaaaatgtg atcatgatga aagccagcaa   5880
tgacgttgca gctgatattg ttgtcggcca accgcgccga aaacgcagct gtcagaccca   5940
cagcctccaa cgaagaatgt atcgtcaaag tgatccaagc acactcatag ttggagtcgt   6000
actccaaagg cggcaatgac gagtcagaca gatactcgtc gacgtttaaa cagtgtacgc   6060
agatctacta tagaggaaca tttaaattgc cccggagaag acggccaggc cgcctagatg   6120
acaaattcaa caactcacag ctgactttct gccattgcca ctagggggg gccttttat    6180 atggccaagc caagctctcc acgtcggttg ggctgcaccc aacaataaat gggtagggtt   6240
gcaccaacaa agggatggga tgggggtag aagatacgag gataacgggg ctcaatggca    6300
caaataagaa cgaatactgc cattaagact cgtgatccag cgactgacac cattgcatca   6360
tctaagggcc tcaaaactac ctcggaactg ctgcgctgat ctggacacca cagaggttcc   6420
gagcacttta ggttgcacca aatgtcccac caggtgcagg cagaaaacgc tggaacagcg   6480
tgtacagttt gtcttagcaa aaagtgaagg cgctgaggtc gagcagggtg gtgtgacttg   6540
ttatagcctt tagagctgcg aaagcgcgta tggatttggc tcatcaggcc agattgaggg   6600
tctgtggaca catgtcatgt tagtgtactt caatcgcccc ctggatatag ccccgacaat   6660
aggccgtggc ctcattttt tgccttccgc acatttccat tgctcgatac ccacaccttg    6720
cttctcctgc acttgccaac cttaatactg gtttacattg accaacatct acaagcggg    6780 gggcttgtct agggtatata taaacagtgg ctctcccaat cggttgccag tctcttttt    6840 cctttctttc cccacagatt cgaaatctaa actacacatc acagaattcc gagccgtgag   6900
tatccacgac aagatcagtg tcgagacgac gcgttttgtg taatgacaca atccgaaagt   6960
cgctagcaac acacactctc tacacaaact aacccagctc tggtaccagc ggccatcaca   7020
agtttgtaca aaaaagttgg tttttttcgg tctaaaatgg aagcagccaa agaattggtt   7080
tccatcgtcc aagaggagct ccccaaggtg gactatgccc agctttggca ggatgccagc   7140
agctgtgagg tcctttacct ctcggtggca ttcgtggcga tcaagttcat gctgcgccca   7200
ctggacctga agcgccaggc caccttgaag aagctgttca cagcatacaa cttcctcatg   7260
tcgatctatt cctttggctc cttcctggcc atggcctatg ccctatcagt aactggcatc   7320
ctctccggcg actgtgagac ggcgttcaac aacgatgtgt tcaggatcac aactcagctg   7380
ttctacctca gcaagttcgt agagtacatc gactccttct accttcccct tatggacaag   7440
ccactgtcgt tccttcagtt cttccatcat ttgggggccc ccattgacat gtggctattc   7500
tacaaatacc gcaacgaagg agtctggatc tttgtcctgt tgaatgggtt cattcactgg   7560
atcatgtacg gttactattg gacgcggctc atcaagctga acttccccat gcccaagaac   7620
ctgatcacct ccatgcagat catccagttc aatgtcgggt tctacatcgt ctggaagtac   7680
cgcaatgtgc catgctaccg ccaggatggg atgcgcatgt ttgcctggat cttcaactac   7740
tggtatgtcg ggacggtctt gctgctgttc ctcaactttt acgtgcagac gtacatccgg   7800
aagccgagga agaaccgagg gaagaaggag taggccacat ggcgcctgcg ctggaggaaa   7860
```

```
cggtacgctc ggatggtgca ctgcacttgc actccgccgt ttctagcctc ccctcgctct    7920
aaccactgcg gcatgcctgc ttgaggcgtg acgttgcctc gtatgataca gtttacaccc    7980
ttcccacagc ccacggagct ggtgactgtt tccagcgtct gcagatcatt gatctggtgc    8040
aatgtgcaca gaccaagccc ctctaacgtc ttgcggtgta ccgctcgaca ctcactgcaa    8100
gagacagatg gctgagcatg ttatagcccc ttacattcta cccttcgtcc caacctgacc    8160
gtcacattcn nnnnnnnnn nnnnnnnnnn nnnnnnnnnn nnnnnnnnna cccaacttt     8219
```

<210> SEQ ID NO 25
<211> LENGTH: 8235
<212> TYPE: DNA
<213> ORGANISM: Artificial Sequence
<220> FEATURE:
<223> OTHER INFORMATION: plasmid pY174
<220> FEATURE:
<221> NAME/KEY: misc_feature
<222> LOCATION: (8186)..(8225)
<223> OTHER INFORMATION: n is a, c, g, or t

<400> SEQUENCE: 25

```
cttgtacaaa gtggtgatgg ccgcaagtgt ggatggggaa gtgagtgccc ggttctgtgt      60
gcacaattgg caatccaaga tggatggatt caacacaggg atatagcgag ctacgtggtg     120
gtgcgaggat atagcaacgg atatttatgt ttgacacttg agaatgtacg atacaagcac     180
tgtccaagta caatactaaa catactgtac atactcatac tcgtacccgg caacggtttc     240
acttgagtgc agtggctagt gctcttactc gtacagtgtg caatactgcg tatcatagtc     300
tttgatgtat atcgtattca ttcatgttag ttgcgtacga gccggaagca taaagtgtaa     360
agcctggggt gcctaatgag tgagctaact cacattaatt gcgttgcgct cactgcccgc     420
tttccagtcg ggaaacctgt cgtgccagct gcattaatga atcggccaac gcgcggggag     480
aggcggtttg cgtattgggc gctcttccgc ttcctcgctc actgactcgc tgcgctcggt     540
cgttcggctg cggcgagcgg tatcagctca ctcaaaggcg gtaatacggt tatccacaga     600
atcaggggat aacgcaggaa agaacatgtg agcaaaaggc cagcaaaagg ccaggaaccg     660
taaaaaggcc gcgttgctgg cgtttttcca taggctccgc cccctgacg agcatcacaa      720 aaatcgacgc tcaagtcaga ggtggcgaaa cccgacagga ctataaagat accaggcgtt     780
tccccctgga agctccctcg tgcgctctcc tgttccgacc ctgccgctta ccggatacct     840
gtccgccttt ctcccttcgg gaagcgtggc gctttctcat agctcacgct gtaggtatct     900
cagttcggtg taggtcgttc gctccaagct gggctgtgtg cacgaacccc ccgttcagcc     960
cgaccgctgc gccttatccg gtaactatcg tcttgagtcc aacccggtaa gacacgactt    1020
atcgccactg gcagcagcca ctggtaacag gattagcaga gcgaggtatg taggcggtgc    1080
tacagagttc ttgaagtggt ggcctaacta cggctacact agaaggacag tatttggtat    1140
ctgcgctctg ctgaagccag ttaccttcgg aaaaagagtt ggtagctctt gatccggcaa    1200
acaaaccacc gctggtagcg gtggtttttt tgtttgcaag cagcagatta cgcgcagaaa    1260
aaaaggatct caagaagatc ctttgatctt ttctacgggg tctgacgctc agtggaacga    1320
aaactcacgt taagggattt tggtcatgag attatcaaaa aggatcttca cctagatcct    1380
tttaaattaa aaatgaagtt ttaaatcaat ctaaagtata tatgagtaaa cttggtctga    1440
cagttaccaa tgcttaatca gtgaggcacc tatctcagcg atctgtctat ttcgttcatc    1500
catagttgcc tgactccccg tcgtgtagat aactacgata cgggagggct taccatctgg    1560
ccccagtgct gcaatgatac cgcgagaccc acgctcaccg gctccagatt tatcagcaat    1620
```

```
aaaccagcca gccggaaggg ccgagcgcag aagtggtcct gcaactttat ccgcctccat    1680
ccagtctatt aattgttgcc gggaagctag agtaagtagt tcgccagtta atagtttgcg    1740
caacgttgtt gccattgcta caggcatcgt ggtgtcacgc tcgtcgtttg gtatggcttc    1800
attcagctcc ggttcccaac gatcaaggcg agttacatga tcccccatgt tgtgcaaaaa    1860
agcggttagc tccttcggtc ctccgatcgt tgtcagaagt aagttggccg cagtgttatc    1920
actcatggtt atggcagcac tgcataattc tcttactgtc atgccatccg taagatgctt    1980
ttctgtgact ggtgagtact caaccaagtc attctgagaa tagtgtatgc ggcgaccgag    2040
ttgctcttgc ccggcgtcaa tacgggataa taccgcgcca catagcagaa ctttaaaagt    2100
gctcatcatt ggaaaacgtt cttcggggcg aaaactctca aggatcttac cgctgttgag    2160
atccagttcg atgtaaccca ctcgtgcacc caactgatct tcagcatctt ttactttcac    2220
cagcgtttct gggtgagcaa aaacaggaag gcaaaatgcc gcaaaaaagg gaataagggc    2280
gacacggaaa tgttgaatac tcatactctt ccttttcaa tattattgaa gcatttatca    2340
gggttattgt ctcatgagcg gatacatatt tgaatgtatt tagaaaaata aacaaatagg    2400
ggttccgcgc acatttcccc gaaaagtgcc acctgacgcg ccctgtagcg gcgcattaag    2460
cgcggcgggt gtggtggtta cgcgcagcgt gaccgctaca cttgccagcg ccctagcgcc    2520
cgctcctttc gctttcttcc cttcctttct cgccacgttc gccggctttc cccgtcaagc    2580
tctaaatcgg gggctccctt tagggttccg atttagtgct ttacggcacc tcgaccccaa    2640
aaaacttgat tagggtgatg gttcacgtag tgggccatcg ccctgataga cggttttcg     2700 cccttgacg ttggagtcca cgttctttaa tagtggactc ttgttccaaa ctggaacaac    2760
actcaaccct atctcggtct attctttga tttataaggg attttgccga tttcggccta    2820
ttggttaaaa aatgagctga tttaacaaaa atttaacgcg aattttaaca aaatattaac    2880
gcttacaatt tccattcgcc attcaggctg cgcaactgtt gggaagggcg atcggtgcgg    2940
gcctcttcgc tattacgcca gctggcgaaa ggggatgtg ctgcaaggcg attaagttgg     3000
gtaacgccag ggttttccca gtcacgacgt tgtaaaacga cggccagtga attgtaatac    3060
gactcactat agggcgaatt gggtaccggg cccccctcg aggtcgatgg tgtcgataag     3120
cttgatatcg aattcatgtc acacaaaccg atcttcgcct caaggaaacc taattctaca    3180
tccgagagac tgccgagatc cagtctacac tgattaattt tcgggccaat aatttaaaaa    3240
aatcgtgtta tataatatta tatgtattat atatatacat catgatgata ctgacagtca    3300
tgtcccattg ctaaatagac agactccatc tgccgcctcc aactgatgtt ctcaatattt    3360 aagggggtcat ctcgcattgt ttaataataa acagactcca tctaccgcct ccaaatgatg    3420
ttctcaaaat atattgtatg aacttatttt tattacttag tattattaga caacttactt    3480
gctttatgaa aaacacttcc tatttaggaa acaatttata atggcagttc gttcatttaa    3540
caatttatgt agaataaatg ttataaatgc gtatgggaaa tcttaaatat ggatagcata    3600
aatgatatct gcattgccta attcgaaatc aacagcaacg aaaaaaatcc cttgtacaac    3660
ataaatagtc atcgagaaat atcaactatc aaagaacagc tattcacacg ttactattga    3720
gattattatt ggacgagaat cacacactca actgtctttc tctcttctag aaatacaggt    3780
acaagtatgt actattctca ttgttcatac ttctagtcat ttcatccac atattccttg      3840 gatttctctc caatgaatga cattctatct tgcaaattca acaattataa taagatatac    3900
caaagtagcg gtatagtggc aatcaaaaag cttctctggt gtgcttctcg tatttatttt    3960
tattctaatg atccattaaa ggtatatatt tatttcttgt tatataatcc ttttgtttat    4020
```

```
tacatgggct ggatacataa aggtattttg atttaattttt ttgcttaaat tcaatccccc    4080
ctcgttcagt gtcaactgta atggtaggaa attaccatac ttttgaagaa gcaaaaaaaa    4140
tgaaagaaaa aaaaaatcgt atttccaggt tagacgttcc gcagaatcta gaatgcggta    4200
tgcggtacat tgttcttcga acgtaaaagt tgcgctccct gagatattgt acattttgc     4260 ttttacaagt acaagtacat cgtacaacta tgtactactg ttgatgcatc cacaacagtt    4320
tgttttgttt tttttgttt ttttttttc taatgattca ttaccgctat gtatacctac      4380
ttgtacttgt agtaagccgg gttattggcg ttcaattaat catagactta tgaatctgca    4440
cggtgtgcgc tgcgagttac ttttagctta tgcatgctac ttgggtgtaa tattgggatc    4500
tgttcggaaa tcaacggatg ctcaatcgat ttcgacagta attaattaag tcatacacaa    4560
gtcagctttc ttcgagcctc atataagtat aagtagttca acgtattagc actgtaccca    4620
gcatctccgt atcgagaaac acaacaacat gccccattgg acagatcatg cggatacaca    4680
ggttgtgcag tatcatacat actcgatcag acaggtcgtc tgaccatcat acaagctgaa    4740
caagcgctcc atacttgcac gctctctata tacacagtta aattacatat ccatagtcta    4800
acctctaaca gttaatcttc tggtaagcct cccagccagc cttctggtat cgcttggcct    4860
cctcaatagg atctcggttc tggccgtaca gacctcggcc gacaattatg atatccgttc    4920
cggtagacat gacatcctca acagttcggt actgctgtcc gagagcgtct cccttgtcgt    4980
caagacccac cccggggggtc agaataagcc agtcctcaga gtcgcccttta ggtcggttct   5040 gggcaatgaa gccaaccaca aactcggggt cggatcgggc aagctcaatg gtctgcttgg    5100
agtactcgcc agtggccaga gagcccttgc aagacagctc ggccagcatg agcagacctc    5160
tggccagctt ctcgttggga gaggggacta ggaactcctt gtactgggag ttctcgtagt    5220
cagagacgtc ctccttcttc tgttcagaga cagtttcctc ggcaccagct cgcaggccag    5280
caatgattcc ggttccgggt acaccgtggg cgttggtgat atcggaccac tcggcgattc    5340
ggtgacaccg gtactggtgc ttgacagtgt tgccaatatc tgcgaacttt ctgtcctcga    5400
acaggaagaa accgtgctta agagcaagtt ccttgagggg gagcacagtg ccggcgtagg    5460
tgaagtcgtc aatgatgtcg atatgggttt tgatcatgca cacataaggt ccgaccttat    5520
cggcaagctc aatgagctcc ttggtggtgg taacatccag agaagcacac aggttggttt    5580
tcttggctgc cacgagcttg agcactcgag cggcaaaggc ggacttgtgg acgttagctc    5640
gagcttcgta ggagggcatt ttggtggtga agaggagact gaaataaatt tagtctgcag    5700
aactttttat cggaacctta tctggggcag tgaagtatat gttatggtaa tagttacgag    5760
ttagttgaac ttatagatag actggactat acggctatcg gtccaaatta gaaagaacgt    5820
caatggctct ctgggcgtcg cctttgccga caaaaatgtg atcatgatga aagccagcaa    5880
tgacgttgca gctgatattg ttgtcggcca accgcgccga aaacgcagct gtcagaccca    5940
cagcctccaa cgaagaatgt atcgtcaaag tgatccaagc acactcatag ttggagtcgt    6000
actccaaagg cggcaatgac gagtcagaca gatactcgtc gacgtttaaa cagtgtacgc    6060
agatctacta tagaggaaca tttaaattgc cccggagaag acggcaggc cgcctagatg      6120 acaaattcaa caactcacag ctgactttct gccattgcca ctaggggggg gccttttat      6180 atggccaagc caagctctcc acgtcggttg ggctgcaccc aacaataaat gggtagggtt    6240
gcaccaacaa agggatggga tggggggtag aagatacgag gataacgggg ctcaatggca    6300
caaataagaa cgaatactgc cattaagact cgtgatccag cgactgacac cattgcatca    6360
tctaagggcc tcaaaactac ctcggaactg ctgcgctgat ctggacacca cagaggttcc    6420
```

```
gagcacttta ggttgcacca aatgtcccac caggtgcagg cagaaaacgc tggaacagcg    6480
tgtacagttt gtcttagcaa aaagtgaagg cgctgaggtc gagcagggtg gtgtgacttg    6540
ttatagcctt tagagctgcg aaagcgcgta tggatttggc tcatcaggcc agattgaggg    6600
tctgtggaca catgtcatgt tagtgtactt caatcgcccc ctggatatag ccccgacaat    6660
aggccgtggc ctcattttt tgccttccgc acatttccat tgctcgatac ccacaccttg    6720
cttctcctgc acttgccaac cttaatactg gtttacattg accaacatct tacaagcggg    6780
gggcttgtct agggtatata taaacagtgg ctctcccaat cggttgccag tctctttttt    6840
cctttctttc cccacagatt cgaaatctaa actacacatc acagaattcc gagccgtgag    6900
tatccacgac aagatcagtg tcgagacgac gcgttttgtg taatgacaca atccgaaagt    6960
cgctagcaac acacactctc tacacaaact aacccagctc tggtaccagc ggccatcaca    7020
agtttgtaca aaaagttgg attttttttc ggtctaaaat ggaagcagcc aaagaattgg    7080
tttccatcgt ccaagaggag ctccccaagg tggactatgc ccagctttgg caggacgcca    7140
gcagctgtga ggtcctttac ctctcggtgg cattcgtggc gatcaagttc atgctgcgcc    7200
cactggacct gaagcgccag gccaccttga agaagctgtt cacagcatac aacttcctca    7260
tgtcgatcta ttcctttggc tccttcctgg ccatggccta tgccctatca gtaactggca    7320
tcctctccgg cgactgtgag acagcgttca acaacgatgt gttcaggatc acaactcagc    7380
tgttctacct cagcaagttc gtagagtaca tcgactcctt ctaccttccc cttatggaca    7440
agccactgtc gttccttcag ttcttccatc atttgggggc tcccattgac atgtggctat    7500
tctacaaata ccgcaacgaa ggagtctgga tctttgtcct gttgaatggg ttcattcact    7560
ggatcatgta cggttactac tggacgcggc tcatcaagct gaacttcccc atgcccaaga    7620
acctgatcac ctccatgcag atcatccagt tcaatgtcgg gttctacatc gtctggaagt    7680
accgcaatgt gccatgctac cgccaggatg ggatgcgcat gtttgcctgg atcttcaact    7740
actggtacgt cgggacggtc ttgctgctgt tcctcaactt ttacgtgcag acgtacatcc    7800
ggaagccgag gaagaaccaa gggaagaagg agtaggccac atggcgcctg cgctggagga    7860
aacggtacgc tcggatggtg cactgcactt gcactccgcc gcttctagcc tcccctcgct    7920
ctaacctctg cgacatgcct gcttgaggcg tgacgttgcc tcgtgcgata cagtttacac    7980
ccttcccatg gcccacggag caggtgactg tctccagcgt ctgcaattct gatcattggt    8040
ctggtgcaat gtgcgcagac caagcccctc taacgtcttg cggtgtaccg ctcgacactc    8100
actgcacgag acagatggct gagcatgtta tagcccctga cattctaccc ttcgtcctta    8160
cctgaccgtc acattcatgc ttaccnnnnn nnnnnnnnnn nnnnnnnnnn nnnnnnnnnn    8220
nnnnnaccca acttt                                                    8235
```

<210> SEQ ID NO 26
<211> LENGTH: 774
<212> TYPE: DNA
<213> ORGANISM: Euglena anabaena
<220> FEATURE:
<221> NAME/KEY: CDS
<222> LOCATION: (1)..(774)
<223> OTHER INFORMATION: delta-9 elongase (codon-optimized for
      expression in Yarrowia lipolytica)

<400> SEQUENCE: 26

```
atg gag gct gcc aag gag ctg gtc tcc atc gtc cag gag gaa ctt ccc        48
Met Glu Ala Ala Lys Glu Leu Val Ser Ile Val Gln Glu Glu Leu Pro
1               5                   10                  15
```

| | | |
|---|---|---|
| aag gtg gac tac gcc cag ctc tgg cag gac gcc tcc tct tgc gag gtt | 96 | |
| Lys Val Asp Tyr Ala Gln Leu Trp Gln Asp Ala Ser Ser Cys Glu Val | | |
| 20 25 30 | | |
| ctg tac ctc tcg gtc gct ttc gtg gcc atc aag ttc atg ctt cga cct | 144 | |
| Leu Tyr Leu Ser Val Ala Phe Val Ala Ile Lys Phe Met Leu Arg Pro | | |
| 35 40 45 | | |
| ctg gac ctc aag cga caa gcc acc ctc aaa aag ctg ttc acc gca tac | 192 | |
| Leu Asp Leu Lys Arg Gln Ala Thr Leu Lys Lys Leu Phe Thr Ala Tyr | | |
| 50 55 60 | | |
| aac ttt ctc atg tcc atc tac tcg ttc ggc tcc ttc ctg gcg atg gcc | 240 | |
| Asn Phe Leu Met Ser Ile Tyr Ser Phe Gly Ser Phe Leu Ala Met Ala | | |
| 65 70 75 80 | | |
| tac gct ctc tct gtc act ggt att ctt tcc ggc gat tgt gag act gcc | 288 | |
| Tyr Ala Leu Ser Val Thr Gly Ile Leu Ser Gly Asp Cys Glu Thr Ala | | |
| 85 90 95 | | |
| ttc aac aat gac gtg ttc cga atc acc act cag ctg ttc tac ctc agc | 336 | |
| Phe Asn Asn Asp Val Phe Arg Ile Thr Thr Gln Leu Phe Tyr Leu Ser | | |
| 100 105 110 | | |
| aag ttc gtc gag tac atc gac tcc ttc tac ctt ccc ctc atg gac aag | 384 | |
| Lys Phe Val Glu Tyr Ile Asp Ser Phe Tyr Leu Pro Leu Met Asp Lys | | |
| 115 120 125 | | |
| ccc ttg tcg ttt ctg cag ttc ttt cac cat ctc gga gct ccc atc gac | 432 | |
| Pro Leu Ser Phe Leu Gln Phe Phe His His Leu Gly Ala Pro Ile Asp | | |
| 130 135 140 | | |
| atg tgg ctg ttc tac aag tat cga aac gaa ggc gtc tgg atc ttt gtt | 480 | |
| Met Trp Leu Phe Tyr Lys Tyr Arg Asn Glu Gly Val Trp Ile Phe Val | | |
| 145 150 155 160 | | |
| ctg ctc aac ggc ttc att cac tgg atc atg tac ggt tac tat tgg acg | 528 | |
| Leu Leu Asn Gly Phe Ile His Trp Ile Met Tyr Gly Tyr Tyr Trp Thr | | |
| 165 170 175 | | |
| cga ctc atc aag ctg aac ttc cct atg ccc aag aac ctc att acc tcc | 576 | |
| Arg Leu Ile Lys Leu Asn Phe Pro Met Pro Lys Asn Leu Ile Thr Ser | | |
| 180 185 190 | | |
| atg caa att atc cag ttc aac gtc gga ttc tac atc gtc tgg aag tac | 624 | |
| Met Gln Ile Ile Gln Phe Asn Val Gly Phe Tyr Ile Val Trp Lys Tyr | | |
| 195 200 205 | | |
| cga aac gtg ccc tgc tac cgg cag gac ggt atg cga atg ttt gcc tgg | 672 | |
| Arg Asn Val Pro Cys Tyr Arg Gln Asp Gly Met Arg Met Phe Ala Trp | | |
| 210 215 220 | | |
| atc ttc aac tac tgg tat gtc ggc acg gtg ctg ctt ctg ttc ctc aac | 720 | |
| Ile Phe Asn Tyr Trp Tyr Val Gly Thr Val Leu Leu Leu Phe Leu Asn | | |
| 225 230 235 240 | | |
| ttc tac gtc cag acc tac att cgg aag cct cga aag aac cga ggc aaa | 768 | |
| Phe Tyr Val Gln Thr Tyr Ile Arg Lys Pro Arg Lys Asn Arg Gly Lys | | |
| 245 250 255 | | |
| aag gag | 774 | |
| Lys Glu | | |

<210> SEQ ID NO 27
<211> LENGTH: 258
<212> TYPE: PRT
<213> ORGANISM: Euglena anabaena

<400> SEQUENCE: 27

Met Glu Ala Ala Lys Glu Leu Val Ser Ile Val Gln Glu Glu Leu Pro
1               5                   10                  15

Lys Val Asp Tyr Ala Gln Leu Trp Gln Asp Ala Ser Ser Cys Glu Val
                20                  25                  30

Leu Tyr Leu Ser Val Ala Phe Val Ala Ile Lys Phe Met Leu Arg Pro
            35                  40                  45

```
Leu Asp Leu Lys Arg Gln Ala Thr Leu Lys Lys Leu Phe Thr Ala Tyr
 50                  55                  60

Asn Phe Leu Met Ser Ile Tyr Ser Phe Gly Ser Phe Leu Ala Met Ala
 65                  70                  75                  80

Tyr Ala Leu Ser Val Thr Gly Ile Leu Ser Gly Asp Cys Glu Thr Ala
                 85                  90                  95

Phe Asn Asn Asp Val Phe Arg Ile Thr Thr Gln Leu Phe Tyr Leu Ser
                100                 105                 110

Lys Phe Val Glu Tyr Ile Asp Ser Phe Tyr Leu Pro Leu Met Asp Lys
            115                 120                 125

Pro Leu Ser Phe Leu Gln Phe Phe His His Leu Gly Ala Pro Ile Asp
        130                 135                 140

Met Trp Leu Phe Tyr Lys Tyr Arg Asn Glu Gly Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Asn Phe Pro Met Pro Lys Asn Leu Ile Thr Ser
                180                 185                 190

Met Gln Ile Ile Gln Phe Asn Val Gly Phe Tyr Ile Val Trp Lys Tyr
            195                 200                 205

Arg Asn Val Pro Cys Tyr Arg Gln Asp Gly Met Arg Met Phe Ala Trp
        210                 215                 220

Ile Phe Asn Tyr Trp Tyr Val Gly Thr Val Leu Leu Leu Phe Leu Asn
225                 230                 235                 240

Phe Tyr Val Gln Thr Tyr Ile Arg Lys Pro Arg Lys Asn Arg Gly Lys
                245                 250                 255

Lys Glu

<210> SEQ ID NO 28
<211> LENGTH: 3497
<212> TYPE: DNA
<213> ORGANISM: Artificial Sequence
<220> FEATURE:
<223> OTHER INFORMATION: Plasmid pEaD9ES

<400> SEQUENCE: 28
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgagctcggt acctcgcgaa   420
tgcatctaga tccatggagg ctgccaagga gctggtctcc atcgtccagg aggaacttcc   480
caaggtggac tacgcccagc tctggcagga cgcctcctct tgcgaggttc tgtacctctc   540
ggtcgctttc gtggccatca gttcatgct tcgacctctg acctcaagc acaagccac   600 cctcaaaaag ctgttcaccg catacaactt tctcatgtcc atctactcgt tcggctcctt   660
cctggcgatg gcctacgctc tctctgtcac tggtattctt ccggcgatt gtgagactgc   720 cttcaacaat gacgtgttcc gaatcaccac tcagctgttc tacctcagca agttcgtcga   780
gtacatcgac tccttctacc ttcccctcat ggacaagccc ttgtcgtttc tgcagttctt   840
tcaccatctc ggagctccca tcgacatgtg gctgttctac aagtatcgaa acgaaggcgt   900
```

-continued

```
ctggatcttt gttctgctca acggcttcat tcactggatc atgtacggtt actattggac      960
gcgactcatc aagctgaact tccctatgcc caagaacctc attacctcca tgcaaattat     1020
ccagttcaac gtcggattct acatcgtctg gaagtaccga aacgtgccct gctaccggca     1080
ggacggtatg cgaatgtttg cctggatctt caactactgg tatgtcggca cggtgctgct     1140
tctgttcctc aacttctacg tccagaccta cattcggaag cctcgaaaga accgaggcaa     1200
aaaggagtaa gcggccgcat cggatcccgg gcccgtcgac tgcagaggcc tgcatgcaag     1260
cttggcgtaa tcatggtcat agctgttttc ctgtgtgaaat tgttatccgc tcacaattcc     1320
acacaacata cgagccggaa gcataaagtg taaagcctgg ggtgcctaat gagtgagcta     1380
actcacatta attgcgttgc gctcactgcc cgctttccag tcgggaaacc tgtcgtgcca     1440
gctgcattaa tgaatcggcc aacgcgcggg gagaggcggt ttgcgtattg ggcgctcttc     1500
cgcttcctcg ctcactgact cgctgcgctc ggtcgttcgg ctgcggcgag cggtatcagc     1560
tcactcaaag gcggtaatac ggttatccac agaatcaggg gataacgcag gaaagaacat     1620
gtgagcaaaa ggccagcaaa aggccaggaa ccgtaaaaag gccgcgttgc tggcgttttt     1680
ccataggctc cgcccccctg acgagcatca caaaaatcga cgctcaagtc agaggtggcg     1740
aaacccgaca ggactataaa gataccaggc gtttccccct ggaagctccc tcgtgcgctc     1800
tcctgttccg accctgccgc ttaccggata cctgtccgcc tttctccctt cgggaagcgt     1860
ggcgctttct catagctcac gctgtaggta tctcagttcg gtgtaggtcg ttcgctccaa     1920
gctgggctgt gtgcacgaac cccccgttca gcccgaccgc tgcgccttat ccggtaacta     1980
tcgtcttgag tccaacccgg taagacacga cttatcgcca ctggcagcag ccactggtaa     2040
caggattagc agagcgaggt atgtaggcgg tgctacagag ttcttgaagt ggtggcctaa     2100
ctacggctac actagaagaa cagtatttgg tatctgcgct ctgctgaagc cagttacctt     2160
cggaaaaaga gttggtagct cttgatccgg caaacaaacc accgctggta gcggtggttt     2220
ttttgtttgc aagcagcaga ttacgcgcag aaaaaaagga tctcaagaag atcctttgat     2280
cttttctacg gggtctgacg ctcagtggaa cgaaaactca cgttaaggga ttttggtcat     2340
gagattatca aaaaggatct tcacctagat ccttttaaat taaaaatgaa gttttaaatc     2400
aatctaaagt atatatgagt aaacttggtc tgacagttac caatgcttaa tcagtgaggc     2460
acctatctca gcgatctgtc tatttcgttc atccatagtt gcctgactcc ccgtcgtgta     2520
gataactacg atacgggagg gcttaccatc tggccccagt gctgcaatga taccgcgaga     2580
cccacgctca ccggctccag atttatcagc aataaaccag ccagccggaa gggccgagcg     2640
cagaagtggt cctgcaactt tatccgcctc catccagtct attaattgtt gccgggaagc     2700
tagagtaagt agttcgccag ttaatagttt gcgcaacgtt gttgccattg ctacaggcat     2760
cgtggtgtca cgctcgtcgt ttggtatggc ttcattcagc tccggttccc aacgatcaag     2820
gcgagttaca tgatccccca tgttgtgcaa aaaagcggtt agctccttcg gtcctccgat     2880
cgttgtcaga agtaagttgg ccgcagtgtt atcactcatg gttatggcag cactgcataa     2940
ttctcttact gtcatgccat ccgtaagatg cttttctgtg actggtgagt actcaaccaa     3000
gtcattctga atagtgtata cgcggcgacc gagttgctct tgcccggcgt caatacggga     3060
taataccgcg ccacatagca gaactttaaa agtgctcatc attggaaaac gttcttcggg     3120
gcgaaaactc tcaaggatct taccgctgtt gagatccagt tcgatgtaac ccactcgtgc     3180
acccaactga tcttcagcat cttttacttt caccagcgtt tctgggtgag caaaaacagg     3240
aaggcaaaat gccgcaaaaa agggaataag ggcgacacgg aaatgttgaa tactcatact     3300
```

| | |
|---|---|
| cttcctttt caatattatt gaagcattta tcagggttat tgtctcatga gcggatacat | 3360 |
| atttgaatgt atttagaaaa ataaacaaat aggggttccg cgcacatttc cccgaaaagt | 3420 |
| gccacctgac gtctaagaaa ccattattat catgacatta acctataaaa ataggcgtat | 3480 |
| cacgaggccc tttcgtc | 3497 |

<210> SEQ ID NO 29
<211> LENGTH: 7769
<212> TYPE: DNA
<213> ORGANISM: Artificial Sequence
<220> FEATURE:
<223> OTHER INFORMATION: Plasmid pZUFmEaD9ES

<400> SEQUENCE: 29

| | |
|---|---|
| ggccgcaagt gtggatgggg aagtgagtgc ccggttctgt gtgcacaatt ggcaatccaa | 60 |
| gatggatgga ttcaacacag ggatatagcg agctacgtgg tggtgcgagg atatagcaac | 120 |
| ggatatttat gtttgacact tgagaatgta cgatacaagc actgtccaag tacaatacta | 180 |
| aacatactgt acatactcat actcgtaccc gggcaacggt ttcacttgag tgcagtggct | 240 |
| agtgctctta ctcgtacagt gtgcaatact gcgtatcata gtctttgatg tatatcgtat | 300 |
| tcattcatgt tagttgcgta cgagccggaa gcataaagtg taaagcctgg ggtgcctaat | 360 |
| gagtgagcta actcacatta attgcgttgc gctcactgcc cgctttccag tcgggaaacc | 420 |
| tgtcgtgcca gctgcattaa tgaatcggcc aacgcgcggg gagaggcggt ttgcgtattg | 480 |
| ggcgctcttc cgcttcctcg ctcactgact cgctgcgctc ggtcgttcgg ctgcggcgag | 540 |
| cggtatcagc tcactcaaag gcggtaatac ggttatccac agaatcaggg gataacgcag | 600 |
| gaaagaacat gtgagcaaaa ggccagcaaa aggccaggaa ccgtaaaaag gccgcgttgc | 660 |
| tggcgttttt ccataggctc cgcccccctg acgagcatca caaaaatcga cgctcaagtc | 720 |
| agaggtggcg aaacccgaca ggactataaa gataccaggc gtttccccct ggaagctccc | 780 |
| tcgtgcgctc tcctgttccg accctgccgc ttaccggata cctgtccgcc tttctccctt | 840 |
| cgggaagcgt ggcgctttct catagctcac gctgtaggta tctcagttcg gtgtaggtcg | 900 |
| ttcgctccaa gctgggctgt gtgcacgaac ccccgttca gcccgaccgc tgcgccttat | 960 |
| ccggtaacta tcgtcttgag tccaacccgg taagacacga cttatcgcca ctggcagcag | 1020 |
| ccactggtaa caggattagc agagcgaggt atgtaggcgg tgctacagag ttcttgaagt | 1080 |
| ggtggcctaa ctacggctac actagaagga cagtatttgg tatctgcgct ctgctgaagc | 1140 |
| cagttacctt cggaaaaaga gttggtagct cttgatccgg caaacaaacc accgctggta | 1200 |
| gcggtggttt ttttgtttgc aagcagcaga ttacgcgcag aaaaaaagga tctcaagaag | 1260 |
| atcctttgat cttttctacg gggtctgacg ctcagtggaa cgaaaactca cgttaaggga | 1320 |
| ttttggtcat gagattatca aaaaggatct cacctagat ccttttaaat taaaaatgaa | 1380 |
| gttttaaatc aatctaaagt atatatgagt aaacttggtc tgacagttac caatgcttaa | 1440 |
| tcagtgaggc acctatctca gcgatctgtc tatttcgttc atccatagtt gcctgactcc | 1500 |
| ccgtcgtgta gataactacg atacgggagg gcttaccatc tggccccagt gctgcaatga | 1560 |
| taccgcgaga cccacgctca ccggctccag atttatcagc aataaaccag ccagccggaa | 1620 |
| gggccgagcg cagaagtggt cctgcaactt tatccgcctc catccagtct attaattgtt | 1680 |
| gccgggaagc tagagtaagt agttcgccag ttaatagttt cgcaacgtt gttgccattg | 1740 |
| ctacaggcat cgtggtgtca cgctcgtcgt ttggtatggc ttcattcagc tccgttccc | 1800 |
| aacgatcaag gcgagttaca tgatccccca tgttgtgcaa aaaagcggtt agctccttcg | 1860 |

```
gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga gaatagtgta tgcggcgacc gagttgctct tgcccggcgt    2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttccttttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgccctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca gctctaaat cggggggctcc    2580 ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt aatagtggga ctcttgttcc aaactggaac aacactcaac cctatctcgg    2760
tctattcttt tgatttataa gggattttgc cgatttcggc ctattggtta aaaaatgagc    2820
tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaagggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaagggt catctcgcat    3360 tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg ctggataca     4020 taaaggtatt ttgatttaat ttttgctta aattcaatcc ccctcgttc agtgtcaact      4080 gtaatggtag gaaattacca tacttttgaa gaagcaaaaa aaatgaaaga aaaaaaaaat    4140
cgtatttcca ggttagacgt tccgcagaat ctagaatgcg gtatgcgta cattgttctt     4200 cgaacgtaaa agttgcgctc cctgagatat tgtacatttt tgcttttaca agtacaagta    4260
```

```
catcgtacaa ctatgtacta ctgttgatgc atccacaaca gtttgttttg ttttttttg      4320 ttttttttt  ttctaatgat tcattaccgc tatgtatacc tacttgtact tgtagtaagc      4380
cgggttattg gcgttcaatt aatcatagac ttatgaatct gcacggtgtg cgctgcgagt      4440
tacttttagc ttatgcatgc tacttgggtg taatattggg atctgttcgg aaatcaacgg      4500
atgctcaatc gatttcgaca gtaattaatt aagtcataca caagtcagct ttcttcgagc      4560
ctcatataag tataagtagt tcaacgtatt agcactgtac ccagcatctc cgtatcgaga      4620
aacacaacaa catgccccat tggacagatc atgcggatac acaggttgtg cagtatcata      4680
catactcgat cagacaggtc gtctgaccat catacaagct gaacaagcgc tccatacttg      4740
cacgctctct atatacacag ttaaattaca tatccatagt ctaacctcta acagttaatc      4800
ttctggtaag cctcccagcc agccttctgg tatcgcttgg cctcctcaat aggatctcgg      4860
ttctggccgt acagacctcg gccgacaatt atgatatccg ttccggtaga catgacatcc      4920
tcaacagttc ggtactgctg tccgagagcg tctcccttgt cgtcaagacc caccccgggg      4980
gtcagaataa gccagtcctc agagtcgccc ttaggtcggt tctgggcaat gaagccaacc      5040
acaaactcgg ggtcggatcg ggcaagctca atggtctgct tggagtactc gccagtggcc      5100
agagagccct tgcaagacag ctcggccagc atgagcagac ctctggccag cttctcgttg      5160
ggagagggga ctaggaactc cttgtactgg gagttctcgt agtcagagac gtcctccttc      5220
ttctgttcag agacagtttc ctcggcacca gctcgcaggc cagcaatgat tccggttccg      5280
ggtacaccgt gggcgttggt gatatcggac cactcggcga ttcggtgaca ccggtactgg      5340
tgcttgacag tgttgccaat atctgcgaac tttctgtcct cgaacaggaa gaaaccgtgc      5400
ttaagagcaa gttccttgag ggggagcaca gtgccggcgt aggtgaagtc gtcaatgatg      5460
tcgatatggg ttttgatcat gcacacataa ggtccgacct tatcggcaag ctcaatgagc      5520
tccttggtgg tggtaacatc cagagaagca cacaggttgg ttttcttggc tgccacgagc      5580
ttgagcactc gagcggcaaa ggcggacttg tggacgttag ctcgagcttc gtaggagggc      5640
attttggtgt tgaagaggag actgaaataa atttagtctg cagaactttt tatcggaacc      5700
ttatctgggg cagtgaagta tatgttatgg taatagttac gagttagttg aacttataga      5760
tagactggac tatacggcta tcggtccaaa ttagaaagaa cgtcaatggc tctctgggcg      5820
tcgcctttgc cgacaaaaat gtgatcatga tgaaagccag caatgacgtt gcagctgata      5880
ttgttgtcgg ccaaccgcgc cgaaaacgca gctgtcagac ccacagcctc caacgaagaa      5940
tgtatcgtca aagtgatcca agcacactca tagttggagt cgtactccaa aggcggcaat      6000
gacgagtcag acagatactc gtcgacgttt aaacagtgta cgcagatcta ctatagagga      6060
acatttaaat tgccccggag aagacggcca ggccgcctag atgacaaatt caacaactca      6120
cagctgactt tctgccattg ccactagggg ggggccttt tatatggcca agccaagctc      6180
tccacgtcgg ttgggctgca cccaacaata aatgggtagg gttgcaccaa caagggatg      6240 ggatgggggg tagaagatac gaggataacg gggctcaatg gcacaaataa gaacgaatac      6300
tgccattaag actcgtgatc cagcgactga caccattgca tcatctaagg gcctcaaaac      6360
tacctcggaa ctgctgcgct gatctggaca ccacagaggt tccgagcact ttaggttgca      6420
ccaaatgtcc caccaggtgc aggcagaaaa cgctggaaca gcgtgtacag tttgtcttaa      6480
caaaaagtga gggcgctgag gtcgagcagg gtggtgtgac ttgttatagc ctttagagct      6540
gcgaaagcgc gtatggattt ggctcatcag gccagattga gggtctgtgg acacatgtca      6600
tgttagtgta cttcaatcgc cccctggata tagccccgac aataggccgt ggcctcattt      6660
```

```
ttttgccttc cgcacatttc cattgctcga tacccacacc ttgcttctcc tgcacttgcc    6720
aaccttaata ctggtttaca ttgaccaaca tcttacaagc gggggcttg tctagggtat     6780 atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atggaggctg ccaaggagct ggtctccatc    7020
gtccaggagg aacttcccaa ggtggactac gcccagctct ggcaggacgc ctcctcttgc    7080
gaggttctgt acctctcggt cgctttcgtg gccatcaagt tcatgcttcg acctctggac    7140
ctcaagcgac aagccaccct caaaaagctg ttcaccgcat acaactttct catgtccatc    7200
tactcgttcg gctccttcct ggcgatggcc tacgctctct ctgtcactgg tattctttcc    7260
ggcgattgtg agactgcctt caacaatgac gtgttccgaa tcaccactca gctgttctac    7320
ctcagcaagt tcgtcgagta catcgactcc ttctaccttc ccctcatgga caagcccttg    7380
tcgtttctgc agttctttca ccatctcgga gctcccatcg acatgtggct gttctacaag    7440
tatcgaaacg aaggcgtctg gatctttgtt ctgctcaacg gcttcattca ctggatcatg    7500
tacggttact attggacgcg actcatcaag ctgaacttcc ctatgcccaa gaacctcatt    7560
acctccatgc aaattatcca gttcaacgtc ggattctaca tcgtctggaa gtaccgaaac    7620
gtgccctgct accggcagga cggtatgcga atgtttgcct ggatcttcaa ctactggtat    7680
gtcggcacgg tgctgcttct gttcctcaac ttctacgtcc agacctacat tcggaagcct    7740
cgaaagaacc gaggcaaaaa ggagtaagc                                     7769
```